(12) United States Patent
Miyake et al.

(10) Patent No.: US 8,507,453 B2
(45) Date of Patent: *Aug. 13, 2013

(54) ANTI-PENICILLIN RESISTANT PNEUMOCOCCI AGENT AND NOVEL 16-MEMBERED MACROLIDE DERIVATIVE

(75) Inventors: Toshiaki Miyake, Kanagawa (JP); Yoshiaki Takahashi, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 72 days.

This patent is subject to a terminal disclaimer.

(21) Appl. No.: 13/241,967

(22) Filed: Sep. 23, 2011

(65) Prior Publication Data

US 2012/0015896 A1    Jan. 19, 2012

Related U.S. Application Data

(63) Continuation of application No. 11/795,851, filed as application No. PCT/JP2006/301014 on Jan. 24, 2006, now Pat. No. 8,053,418.

(30) Foreign Application Priority Data

Jan. 24, 2005 (JP) ................................ 2005-015931

(51) Int. Cl.
   *A61K 31/70* (2006.01)
   *C07H 17/08* (2006.01)

(52) U.S. Cl.
   USPC ............................................ 514/30; 536/7.1

(58) Field of Classification Search
   USPC ............................................ 536/7.1; 514/30
   See application file for complete search history.

(56) References Cited

U.S. PATENT DOCUMENTS

| 4,459,290 A | 7/1984 | Kirst et al. |
| 4,490,524 A | 12/1984 | Fujiwara et al. |
| 4,515,941 A | 5/1985 | Fujiwara et al. |
| 5,096,888 A | 3/1992 | Umezawa et al. |
| 5,716,939 A | 2/1998 | Lundy et al. |
| 6,514,946 B1 | 2/2003 | Miyake et al. |

FOREIGN PATENT DOCUMENTS

| JP | 57-005000 | 1/1982 |
| JP | 58-015997 | 1/1983 |
| JP | 58-140097 | 8/1983 |
| JP | 58-174398 | 10/1983 |
| JP | 59-31795 | 2/1984 |
| JP | 59-122498 | 7/1984 |
| JP | 60-034985 | 2/1985 |
| JP | 61-050993 | 3/1986 |
| JP | 02-275894 | 11/1990 |

OTHER PUBLICATIONS

Ubukata, Kimiko et al., "In vitro activities of new ketolide, telithromycin, and eight other macrolide antibiotics against *Streptococcus pneumoniae* having mefA and ermB genes that mediate macrolide resistance," Journal of Infection and Chemotherapy, Sep. 2003, vol. 9, No. 3, p. 221-226.

"Penicillin-resistant Pneumococcus (PRSP)—including macrolide resistance," The Journal of the Japanese Society of Clinical Cytology, 2001, vol. 59, No. 4, pp. 681-686.

"Synthesis of 3,4'-Dideoxymycaminosyl Tylonolide, A Novel Type of Macrolide Derivative," The Journal of Antibiotics, vol. 45, No. 1, p. 144-146, Jan. 1992.

"In Vitro Activity of MC-352, a New 16-Membered Macrolide," Antimicrobial Agents and Chemotherapy, vol. 36, No. 8, p. 1699-1702, Aug. 1992.

Tanaka, A., et al., "Syntheses of Derivatives of 4'-Deoxymycaminosyl Tylonolide and Mycaminosyl Tylonolide Modified at C-23" The Journal of Antibiotics, vol. 34, No. 10, pp. 1377-1380.

Tanaka, A., et al., "Syntheses of 23-Dialkylamino Derivatives of Mycaminosyl Tylonolide and 4'-Deoxymycaminosyl Tylonolide Effective Against Gram-Negative Bacteria," The Journal of Antibiotics, Jan. 1982, vol. 35, No. 1, pp. 113-116.

Kirst, H.A. et al., "In Vitro and In Vivo Evaluation of C-20- and C-23-Modified Derivatives of Tylosin Against Veterinary Pathogens," The Journal of Antibiotics, Jul. 1988, vol. 41, No. 7, pp. 938-948.

*Primary Examiner* — Elli Peselev
(74) *Attorney, Agent, or Firm* — Carmody & Torrance LLP

(57) ABSTRACT

A novel compound that has antimicrobial activity against penicillin-resistant *Streptococcus pneumoniae*, and an anti-penicillin resistant pneumococci agent that includes the compound as an active ingredient are provided. Thus, an anti-penicillin resistant pneumococci agent is provided that includes as an active ingredient a compound represented by the following formula (I) or a pharmacologically acceptable salt thereof, or hydrates thereof:

formula (I)

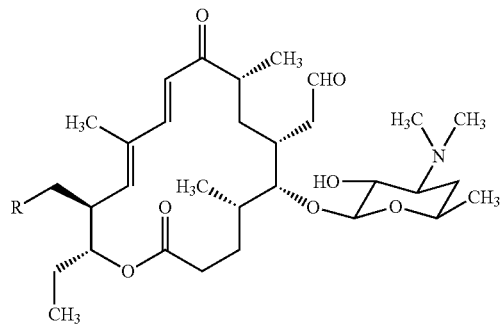

wherein, in the formula (I), R represents any one of a halogen atom, an azido group, Ra-Wa-, Rb-Wb-, Rc-Wc-, and RdRd'N—.

4 Claims, No Drawings

ANTI-PENICILLIN RESISTANT PNEUMOCOCCI AGENT AND NOVEL 16-MEMBERED MACROLIDE DERIVATIVE

CROSS REFERENCE TO RELATED APPLICATIONS

This application is a continuation of U.S. application Ser. No. 11/795,851 filed Feb. 15, 2008, now U.S. Pat. No. 8,053,418, which was the National Stage of International Application No. PCT/JP2006/301014, filed Jan. 24, 2006, which claims priority to Japanese Patent Application No. 2005-015931, filed Jan. 24, 2005, the subject matter which is hereby incorporated by reference.

TECHNICAL FIELD

The present invention relates to 16-membered macrolide antibiotics, more specifically, to 3,4'-dideoxymycaminosyltylonolide derivatives and anti-penicillin resistant pneumococci agents that comprise them as an active ingredient.

BACKGROUND ART

*Streptococcus pneumoniae* are pathogens that cause various diseases including respiratory tract infections such as pneumonia and bronchitis, sinusitis, otitis media, and meningitis. Among the diseases caused by the infection with the *Streptococcus pneumoniae*, pneumonia is a disease with a high death rate in elderly people aged 65 or older, following cancer, heart disease and cerebral stroke, and is a big issue. In addition, since *Streptococcus pneumoniae* that have become resistant to antibiotics such as penicillin are increasing, the number of cases where the treatment of the disorder due to the infection with the *Streptococcus pneumoniae* is difficult has been increased. Especially; penicillin-resistant strains have increased from late 1980s around the world, and it is said that if low susceptible strains are included, currently the penicillin-resistant strains occupy approximately half of clinical isolates.

Currently, in order to treat pneumococcal infection, surgical treatments and antimicrobial agents are used in combination in the case of patients with otitis media or sinusitis. For the treatment of patients with severe infection such as pneumonia, meningitis, and postoperative wound infection, it is essential to administer antimicrobial agents which are expected to be effective against certain pathogens. Typically, carbapenem antibiotics or penicillin antibiotics that serve as the antimicrobial agent are administered in high doses, but in severe cases, carbapenem antibiotics and glycopeptide antibiotics are used in combination.

Thus, although there is a concern that the use of carbapenem antibiotics or glycopeptide antibiotics may increase resistant bacteria, carbapenem antibiotics and glycopeptide antibiotics are still used because they are useful as a therapeutic agent for penicillin-resistant pneumococcal infection.

The number of bacteria resistant to antibiotics has increased on the front lines of health care. Under such circumstances, there is a need for novel antibiotics that have antimicrobial activity against penicillin-resistant bacteria and that can be clearly distinguished structurally. For example, it is known that 3,4'-dideoxymycaminosyltylonolide has an excellent antimicrobial effect against general Gram-positive bacteria and Gram-negative bacteria (See Non-Patent Literatures 1 and 2, Patent Literature 1). However, antimicrobial activity against penicillin-resistant *Streptococcus pneumoniae* (hereinafter, may be briefly referred to as "PRSP") is not described in the above-mentioned Literatures. Since generally, macrolide antibiotics can be used reliably in medical care, it is desirable to search for novel anti-PRSP agents from macrolide antibiotics and thus to obtain novel anti-PRSP agents.

Patent Literature 1: Japanese Patent Application Laid-Open OP-A) No. 02-275894
Non-Patent Literature 1: The Journal of Antibiotics, Vol. 45, No. 1, pp. 144-146, 1992
Non-Patent Literature 2: Antimicrobial Agents and Chemotherapy, Vol. 36, No. 8, pp. 1699-1702, 1992

DISCLOSURE OF INVENTION

An object of the present invention is to meet the need, to solve conventional problems and to achieve the following objects. Specifically, an object of the present invention is to provide a novel compound having antimicrobial activity against penicillin-resistant *Streptococcus pneumoniae* and an anti-penicillin resistant pneumococci agent that includes the compound as an active ingredient.

As a result of dedicated investigations conducted by the present inventors to settle the above-mentioned problems, they have found the following experiences or discoveries. Specifically, as a result of search for a compound having antimicrobial activity against penicillin-resistant *Streptococcus pneumoniae* from macrolide antibiotics, they have found that among the compounds that belong to 16-membered macrolide antibiotics which are deoxygenated at the 3- and 4'-positions, penicillin-resistant *Streptococcus pneumoniae* are susceptible to 3,4'-dideoxy-23-substituted mycaminosyltylonolide derivatives.

The present invention is based on the above-mentioned experiences or discoveries by the present inventors, and means for solving the above-mentioned problems are as follows. Specifically, <1> An anti-penicillin resistant pneumococci agent including as an active ingredient a compound represented by the following formula (I) or a pharmacologically acceptable salt thereof, or hydrates thereof:

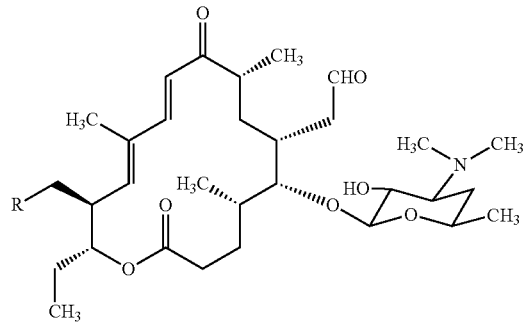

formula (I)

wherein, in the formula (I), R represents any one of a halogen atom, an azido group, Ra-Wa-, Rb-Wb-, Rc-Wc-, and RdRd'N—; the Wa represents one of —CO—O— and —CO—NH—; the Ra represents any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, a 5- to 14-membered ring heteroaralkyl group, a $C_{1-12}$ alkoxy group, an unsaturated $C_{2-12}$ alkoxy group, a $C_{6-14}$ aryloxy group and a 5- to 14-membered ring heteroaryloxy group, which may each have a substituent;

the Wb represents —O—; the Rb represents any one of a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, and a 5- to 14-membered ring heteroaralkyl group, which may each have a substituent; the Wc represents any one of —NH—CO—O—, —NH—CO—NH—, —NH—CS—NH—, and —S—; the Rc represents any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group and a 5- to 14-membered ring heteroaralkyl group, which may each have a substituent; and the Rd and the Rd' may be the same or different and represent any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, a 5- to 14-membered ring heteroaralkyl group, and a 3- to 8-membered ring nonaromatic heterocyclic group which the Rd and the Rd' together form, each of which groups may have a substituent.

<2> The anti-penicillin resistant pneumococci agent according to <1>, wherein, in the formula (I), R represents any one of an azido group, Ra-Wa-, Rb-Wb-, Rc-Wc-, and RdRd'N—; the Wa represents one of —CO—O— and —CO—NH—; the Ra represents any one of a $C_{1-12}$ alkyl group, a $C_{6-14}$ aryl group, a 5- to 14-membered ring heteroaryl group, a $C_{7-16}$ aralkyl group, and a $C_{1-12}$ alkoxy group, which may each have a substituent; the Wb represents —O—; the Rb represents any one of a $C_{1-12}$ alkyl group, an unsaturated $C_{2-12}$ alkyl group, and a $C_{7-16}$ aralkyl group, which may each have a subtituent; the Wc represents any one of —NH—CO—O—, —NH—CO—NH—, and —S—; the Rc represents any one of an unsaturated $C_{2-12}$ alkyl group, a 5- to 14-membered ring heteroaryl group, and a $C_{7-16}$ aralkyl group, which may each have a substituent; and the Rd and the Rd' may be the same or different and represent one of a $C_{1-12}$ alkyl group and a $C_{6-14}$ aryl group, which may each have a substituent.

<3> The anti-penicillin resistant pneumococci agent according to one of <1> and <2>, wherein, in the formula (I), R is one group selected from the groups represented by the following formulae:

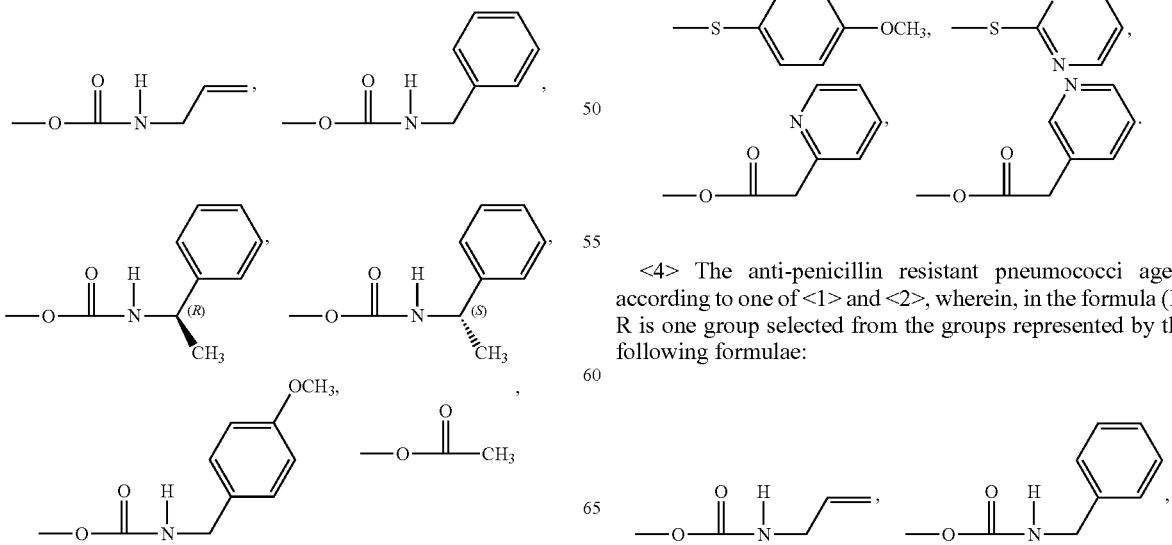

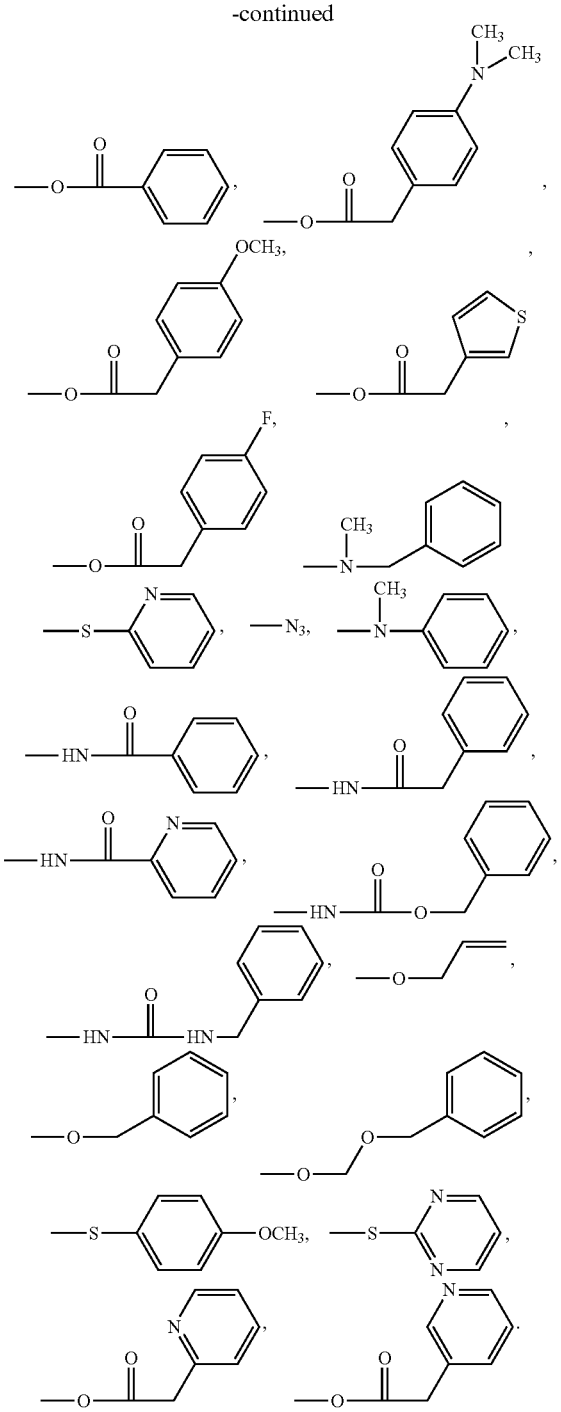

<4> The anti-penicillin resistant pneumococci agent according to one of <1> and <2>, wherein, in the formula (I), R is one group selected from the groups represented by the following formulae:

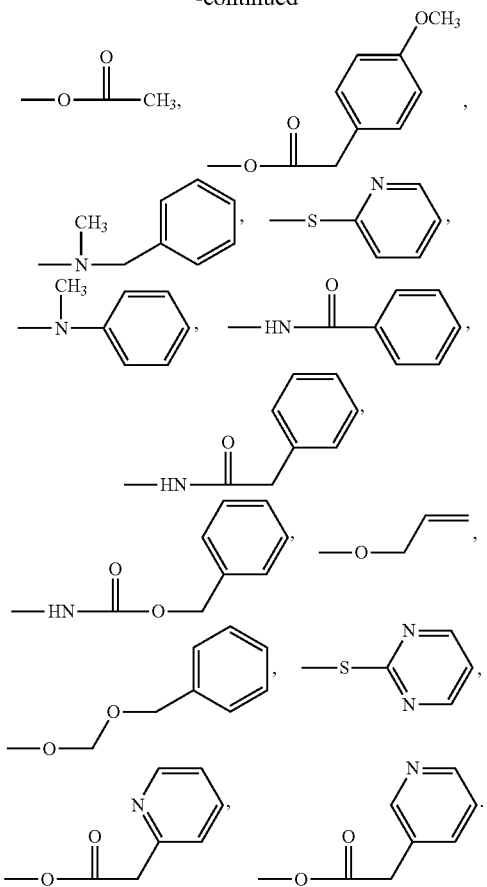

<5> A 16-membered macrolide derivative, which is a compound represented by the following formula (I) or a pharmacologically acceptable salt thereof, or hydrates thereof:

formula (I)

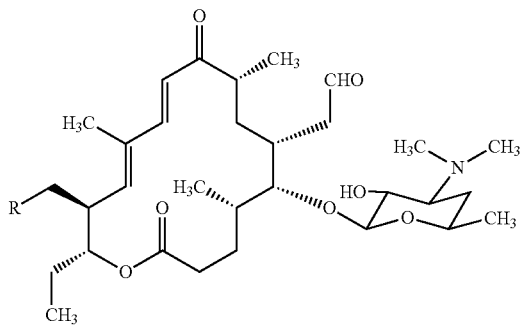

wherein, in the formula (I), R represents any one of an azido group, Rp-Wp-, Rq-Wq-, Rr-Wr-, Rs-Ws-, and Rt-Rt'N—; the Wp represents —CO—O—; the Rp represents any one of a $C_{7-16}$ aralkyl group which has a substituent, a 5- to 14-membered ring heteroaryl group which may have a substituent, and a 5- to 14-membered ring heteroaralkyl group which may have a substituent; the Wq represents —CO—NH—; the Rq represents any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, a 5- to 14-membered ring heteroaralkyl group, a $C_{1-12}$ alkoxy group, an unsaturated $C_{2-12}$ alkoxy group, a $C_{6-14}$ aryloxy group and a 5- to 14-membered ring heteroaryloxy group, which may each have a substituent; the Wr represents —O—; the Rr represents any one of a $C_{1-12}$ alkyl group, an unsaturated $C_{2-12}$ alkyl group, a $C_{6-14}$ aryl group, a 5- to 14-membered ring heteroaryl group, $C_{7-16}$ aralkyl group, and a 5- to 14-membered ring heteroaralkyl group, which may each have a substituent; the Ws represents any one of —NH—CO—O—, —NH—CO—NH—, —NH—CS—NH—, and —S—; the Rs represents any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, and a 5- to 14-membered ring heteroaralkyl group, which may each have a substituent; and the Rt and the Rt' may be the same or different and represent any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, a 5- to 14-membered ring heteroaralkyl group, and a 3- to 8-membered ring nonaromatic heterocyclic group which the Rt and the Rt' together form, each of which groups may have a substituent, however, the Rt and the Rt' do not represent a methyl group simultaneously.

<6> The 16-membered macrolide derivative according to <5>, wherein, in the formula (I), R represents any one of an azido group, Rp-Wp-, Rq-Wq-, Rr-Wr-, Rs-Ws-, and RtRt'N—; the Wp represents —CO—O—; the Rp represents one of a $C_{7-16}$ aralkyl group which has a substituent and a 5- to 14-membered ring heteroaryl group which may have a substituent; the Wq represents —CO—NH—; the Rq represents any one of a $C_{1-12}$ alkyl group, a $C_{6-14}$ aryl group, a 5- to 14-membered ring heteroaryl group, a $C_{7-16}$ aralkyl group, and a $C_{3-12}$ alkoxy group, which may each have a substituent; the Wr represents —O—; the Rr represents any one of a $C_{1-12}$ alkyl group, an unsaturated $C_{2-12}$ alkyl group, and a $C_{7-16}$ aralkyl group, which may each have a substituent; the Ws represents any one of —NH—CO—O—, —NH—CO—NH—, and —S—; the Rs represents any one of a $C_{1-12}$ alkyl group, an unsaturated $C_{2-12}$ alkyl group, a 5- to 14-membered ring heteroaryl group, and a $C_{7-16}$ aralkyl group, which may each have a substituent; and the Rt and the Rt' may be the same or different and represent any one of a $C_{1-12}$ alkyl group, a $C_{6-14}$ aryl group, and a $C_{7-16}$ aralkyl group, which may each have a substituent, however, the Rt and the Rt' do not represent a methyl group simultaneously.

<7> The 16-membered macrolide derivative according to one of <5> and <6>, wherein, in the formula (I), R is one group selected from the groups represented by the following formulae:

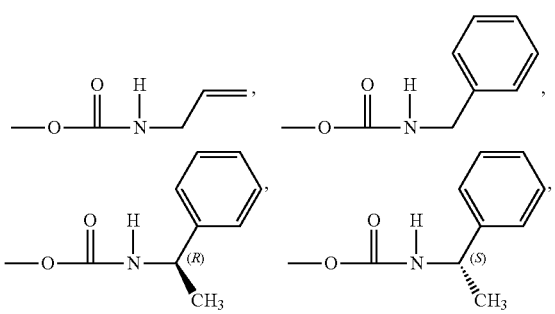

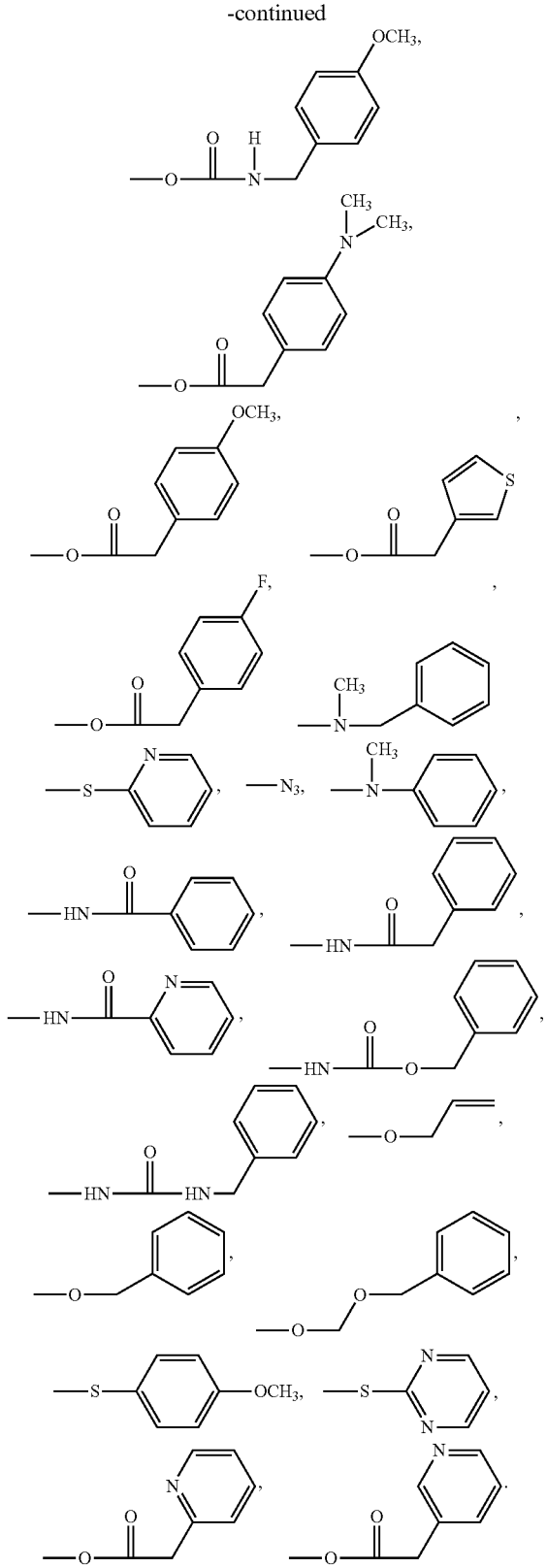
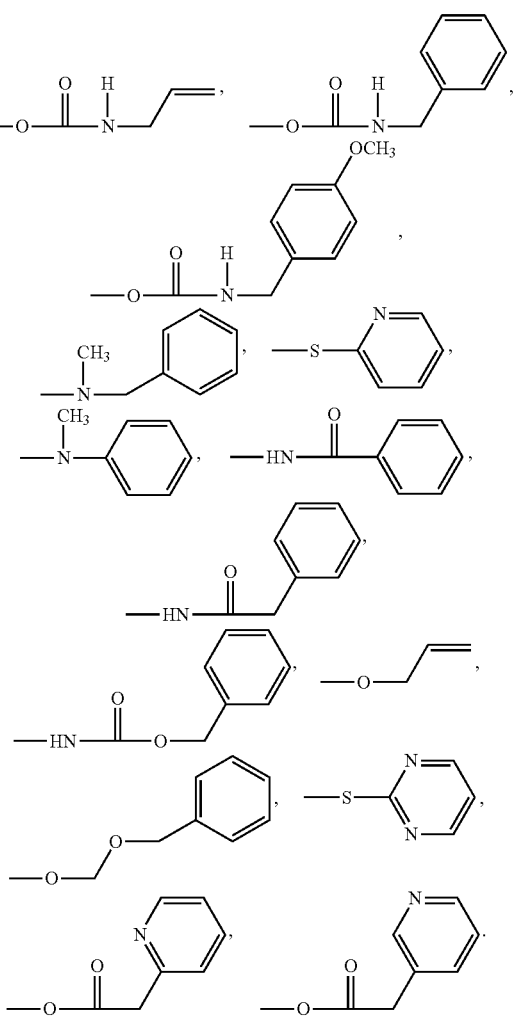

<8> The 16-membered macrolide derivative according to one of <5> and <6>, wherein, in the formula (I), R is one group selected from the groups represented by the following formulae:

The present invention can solve conventional problems and can provide a novel compound having antimicrobial activity against penicillin-resistant *Streptococcus pneumoniae* and an anti-penicillin resistant pneumococci agent that includes the compound as an active ingredient.

BEST MODE FOR CARRYING OUT THE INVENTION (Anti-penicillin Resistant Pneumococci Agent)

The anti-penicillin resistant pneumococci agent of the present invention comprises a 3,4'-dideoxy-23-substituted mycaminosyltylonolide derivative represented by the following formula (I) as an active ingredient and may comprise other components according to necessity.

formula (I)

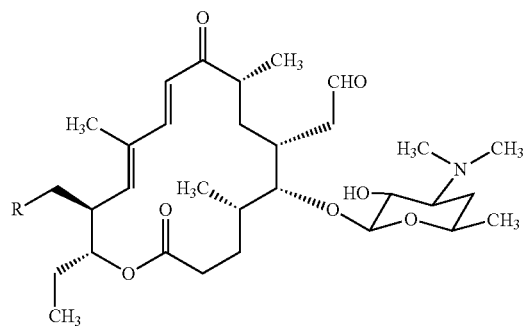

In the formula (I), R represents any one of a halogen atom, an azido group, Ra-Wa-, Rb-Wb-, Rc-Wc-, and RdRd'N—.

The Wa represents one of —CO—O— and —CO—NH—; the Ra represents any one of a hydrogen atom, and $C_{1-12}$ alkyl group, unsaturated $C_{2-12}$ alkyl group, $C_{6-14}$ aryl group, 5- to 14-membered ring heteroaryl group, $C_{7-16}$ aralkyl group, 5- to 14-membered ring heteroaralkyl group, $C_{1-12}$ alkoxy group, unsaturated $C_{2-12}$ alkoxy group, $C_{6-14}$ aryloxy group, and 5- to 14-membered ring heteroaryloxy group, which may each have a substituent; the Wb represents —O—; the Rb represents any one of a $C_{1-12}$ alkyl group, unsaturated $C_{2-12}$ alkyl group, $C_{6-14}$ aryl group, 5- to 14-membered ring heteroaryl group, $C_{7-16}$ aralkyl group, and 5- to 14-membered ring heteroaralkyl group, which may each have a substituent; the Wc represents any one of —NH—CO—O—, —NH—CO—NH—, —NH—CS—NH—, and —S—; the Rc represents any one of a hydrogen atom, and a $C_{1-12}$ alkyl group, unsaturated $C_{2-12}$ alkyl group, $C_{6-14}$ aryl group, 5- to 14-membered ring heteroaryl group, $C_{7-16}$ aralkyl group, and 5- to 14-membered ring heteroaralkyl group, which may each have a substituent; and the Rd and the Rd' may be the same or different and represent any one of a hydrogen atom, and a $C_{1-12}$ alkyl group, unsaturated $C_{2-12}$ alkyl group, $C_{6-14}$ aryl group, 5- to 14-membered ring heteroaryl group, $C_{7-16}$ aralkyl group, 5- to 14-membered ring heteroaralkyl group, and 3- to 8-membered ring nonaromatic heterocyclic group which the Rd and the Rd' together form, each of which groups may have a substituent.

Among these, preferably, the Wa represents one of —CO—O— and —CO—NH—; the Ra represents any one of a $C_{1-12}$ alkyl group, $C_{6-14}$ aryl group, 5- to 14-membered ring heteroaryl group, $C_{7-16}$ aralkyl group, and $C_{1-12}$ alkoxy group, which may each have a substituent; the Wb represents —O—; the Rb represents any one of a $C_{1-12}$ alkyl group, unsaturated $C_{2-12}$ alkyl group, and $C_{7-16}$ aralkyl group, which may each have a substituent; the Wc represents any one of —NH—CO—O—, —NH—CO—NH—, and —S—; the Rc represents any one of an unsaturated $C_{2-12}$ alkyl group, 5- to 14-membered ring heteroaryl group, $C_{7-16}$ aralkyl group, which may each have a substituent; and the Rd and the Rd' may be the same or different and represent one of a $C_{1-12}$ alkyl group and a $C_{6-14}$ aryl group, which may each have a substituent.

<16-Membered Macrolide Derivatives>

The novel 16-membered macrolide derivatives of the present invention are 3,4'-dideoxy-23-substituted mycaminosyltylonolide derivatives represented by the formula (I) or pharmacologically acceptable salts thereof, or hydrates thereof, wherein, in the formula (I), R is any one of an azido group, Rp-Wp-, Rq-Wq-, Rr-Wr-, Rs-Ws-, and RtRt'N—.

The Wp represents —CO—O—; the Rp represents any one of a $C_{7-16}$ aralkyl group that has a substituent, a 5- to 14-membered ring heteroaryl group that may have a substituent, and a 5- to 14-membered ring heteroaralkyl group that may have a substituent; the Wq represents —CO—NH—; the Rq represents any one of a hydrogen atom, and a $C_{1-12}$ alkyl group, unsaturated $C_{2-12}$ alkyl group, $C_{6-14}$ aryl group, 5- to 14-membered ring heteroaryl group, $C_{7-16}$ aralkyl group, 5- to 14-membered ring heteroaralkyl group, $C_{1-12}$ alkoxy group, unsaturated $C_{2-12}$ alkoxy group, $C_{6-14}$ aryloxy group, and 5- to 14-membered ring heteroaryloxy group, which may each have a substituent; the Wr represents —O—; the Rr represents any one of a $C_{1-12}$ alkyl group, unsaturated $C_{2-12}$ alkyl group, $C_{6-14}$ aryl group, 5- to 14-membered ring heteroaryl group, $C_{7-16}$ aralkyl group, and 5- to 14-membered ring heteroaralkyl group, which may each have a substituent; the Ws represents any one of —NH—CO—O—, —NH—CO—NH—, —NH—CS—NH—, and —S—; the Rs represents any one of a hydrogen atom, and a $C_{1-12}$ alkyl group, unsaturated $C_{2-12}$ alkyl group, $C_{6-14}$ aryl group, 5- to 14-membered ring heteroaryl group, $C_{7-16}$ aralkyl group, and 5- to 14-membered ring heteroaralkyl group, which may each have a substituent; and the Rt and the Rt' may be the same or different and represent any one of a hydrogen atom, and a $C_{1-12}$ alkyl group, unsaturated $C_{2-12}$ alkyl group, $C_{6-14}$ aryl group, 5- to 14-membered ring heteroaryl group, $C_{7-16}$ aralkyl group, 5- to 14-membered ring heteroaralkyl group, and 3- to 8-membered ring nonaromatic heterocyclic group which the Rt and the Rt' together form, each of which groups may have a substituent, however, the Rt and the Rt' do not represent a methyl group simultaneously.

Among these, preferably, the Wp represents —CO—O—; the Rp represents one of a $C_{7-16}$ aralkyl group which has a substituent and a 5- to 14-membered ring heteroaryl group which may have a substituent; the Wq represents —CO—NH—; the Rq represents any one of a $C_{1-12}$ alkyl group, $C_{6-14}$ aryl group, 5- to 14-membered ring heteroaryl group, $C_{7-16}$ aralkyl group, and $C_{1-12}$ alkoxy group, which may each have a substituent; the Wr represents —O—; the Rr represents any one of a $C_{1-12}$ alkyl group, unsaturated $C_{2-12}$ alkyl group, and $C_{7-16}$ aralkyl group, which may each have a substituent; the Ws represents any one of —NH—CO—O—, —NH—CO—NH—, and —S—; the Rs represents any one of a $C_{1-12}$ alkyl group, unsaturated $C_{2-12}$ alkyl group, 5- to 14-membered ring heteroaryl group, and $C_{7-16}$ aralkyl group, which may each have a substituent; and the Rt and the Rt' may be the same or different and represent any one of a $C_{1-12}$ alkyl group, $C_{6-14}$ aryl group, and $C_{7-16}$ aralkyl group, which may each have a substituent, however, the Rt and the Rt' do not represent a methyl group simultaneously.

The "halogen atom" includes a fluorine atom, chlorine atom, bromine atom, and iodine atom.

The "$C_{1-12}$ alkyl group" refers to one of a linear or branched alkyl group having 1 to 12 carbon atoms and a cyclic alkyl group having 3 to 10 carbon atoms. Examples of the $C_{1-12}$ alkyl group include a methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, n-heptyl group, n-octyl group, n-nonyl group, n-decyl group, and cyclohexyl group.

Among these, linear or branched alkyl groups having 1 to 6 carbon atoms are preferred. Examples thereof include a methyl group, ethyl group, n-propyl group, iso-propyl group, n-butyl group, iso-butyl group, sec-butyl group, and tert-butyl group.

The "unsaturated $C_{2-12}$ alkyl group" refers to a linear or branched acyclic unsaturated hydrocarbon group having 2 to 12 carbon atoms that has one or more double bonds or triple bonds. Examples of the "unsaturated $C_{2-12}$ alkyl group" include a vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group, 1,6-hexadienyl group, ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group, and 1,6-hexadiynyl group.

Among these, linear or branched alkenyl groups having 2 to 10 carbon atoms, or linear or branched alkynyl groups having 2 to 10 carbon atoms are preferred. Examples thereof include a vinyl group, allyl group, 1-propenyl group, 2-propenyl group, isopropenyl group, ethynyl group, 1-propynyl group, 2-propynyl group, 1-butynyl group, 2-butynyl group, 3-butynyl group, and 3-methyl-1-propynyl group.

The "$C_{6-14}$ aryl group" means an aromatic hydrocarbon cyclic group comprising 6 to 14 carbon atoms and includes a monocyclic group and condensed rings such as a bicyclic group and a tricyclic group.

Examples of the "$C_{6-14}$ aryl group" include a phenyl group, indenyl group, 1-naphthyl group, 2-naphthyl group, azulenyl group, heptalenyl group, indacenyl group, acenaphthenyl group, fluorenyl group, phenalenyl group, phenanthryl group and anthryl group. Among these, a phenyl group, 1-naphthyl group and 2-naphthyl group are preferred.

The "5- to 14-membered ring heteroaryl group" refers to a monocyclic, bicyclic or tricyclic 5-membered to 14-membered aromatic heterocyclic group containing one or more hetero atoms selected from the group consisting of a nitrogen atom, sulfur atom and oxygen atom.

Suitable examples of the 5- to 14-membered ring heteroaryl group include nitrogen-containing aromatic heterocyclic groups such as a pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazinyl group, naphthyridinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbolinyl group, perimidyl group, phenanthrolinyl group, phenazinyl group, imidazopyridinyl group, imidazopyrimidinyl group and pyrazolopyridyl group; sulfur-containing aromatic heterocyclic groups such as a thienyl group and benzothienyl group; oxygen-containing aromatic heterocyclic groups such as a furyl group, pyranyl group, cyclopentapyranyl group, benzofuryl group and isobenzofuryl group; and aromatic heterocyclic groups containing two or more different hetero atoms such as a thiazolyl group, isothiazolyl group, benzothiazolyl group, benzothiadiazolyl group, phenothiazinyl group, isoxazolyl group, furazanyl group, phenoxazinyl group, oxazolyl group, isoxazolyl group, benzoxazolyl group, oxadiazolyl group, pyrazolooxazolyl group, imidazothiazolyl group, thienofuranyl group, furopyrrolyl group and pyridoxazinyl group. Among these, a thienyl group, furyl group, pyridyl group, pyridazinyl group, pyrimidinyl group and pyrazinyl group are more preferable.

The "$C_{7-16}$ aralkyl group" means a group corresponding to the "$C_{1-12}$ alkyl group" of which substitutable moiety is replaced by the "$C_{6-14}$ aryl group". Examples thereof include a benzyl group, phenethyl group, 3-phenylpropyl group, 4-phenylbutyl group, 1-naphthylmethyl group and 2-naphthylmethyl group. Among these, aralkyl groups having 7 to 10 carbon atoms such as a benzyl group and a phenethyl group are preferred.

The "5- to 14-membered ring heteroaralkyl group" means a group corresponding to the "$C_{1-12}$ alkyl group" of which substitutable moiety is replaced by the "5- to 14-membered ring heteroaryl group". Examples thereof include a thienylmethyl group, furylmethyl group, pyridylmethyl group, pyridazinylmethyl group, pyrimidinylmethyl group and pyrazinylmethyl group.

The "$C_{1-12}$ alkoxy group" means a group corresponding to the "$C_{1-12}$ alkyl group" to which end an oxygen atom is bonded. Examples of suitable groups include a methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutyloxy group, 1,3-dimethylbutoxy group, 2-methylpentoxy group, 3-methylpentoxy group, and hexyloxy group.

The "unsaturated $C_{2-12}$ alkoxy group" means a group corresponding to the "unsaturated $C_{2-12}$ alkyl group" to which end an oxygen atom is bonded. Examples of suitable groups include a vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butertyloxy group, 2-butenyloxy group, 3-butenyloxy group, 1-pentenyloxy group, 1-hexenyloxy group, 1,3-hexadiervyloxy group, 1,6-hexadienyloxy group, propargyloxy group and 2-butynyloxy group.

The "$C_{6-14}$ aryloxy group" means a group corresponding to the "$C_{6-14}$ aryl group" to which end an oxygen atom is bonded. Examples thereof include a phenyloxy group, indenyloxy group, 1-naphthyloxy group, 2-naphthyloxy group, azulenyloxy group, heptalenyloxy group, indacenyloxy group, acenaphthenyloxy group, fluorenyloxy group, phenalenyloxy group, phenanthryloxy group, and anthryloxy group.

The "5- to 14-membered ring heteroaryloxy group" means a group corresponding to the "5- to 14-membered ring heteroaryl group" to which end an oxygen atom is bonded. Examples thereof include a pyrrolyloxy group, pyridyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolinyloxy group, isoquinolinyloxy group, quinolizinyloxy group, phthalazinyloxy group, naphthyridinyloxy group, quinoxalinyloxy group, quinazolinyloxy group, cinnolinyloxy group, pteridinyloxy group, imidazotriazinyloxy group, pyrazinopyridazinyloxy group, acridinyloxy group, phenanthridinyloxy group, carbazolyloxy group, carbolinyloxy group, perimidyloxy group, phenanthrolinyloxy group, phenazinyloxy group, imidazopyridinyloxy group, imidazopyrimidinyloxy group, pyrazolopyridinyloxy group, thienyloxy group, benzothienyloxy group, furyloxy group, pyranyloxy group, cyclopentapyranyloxy group, benzofuryloxy group, isobenzofuryloxy group, thiazolyloxy group, isothiazolyloxy group, benzothiazolyloxy group, benzthiadiazolyloxy group, phenothiazinyloxy group, isoxazolyloxy group, furazanyloxy group, phenoxazinyloxy group, oxazolyloxy group, isoxazolyloxy group, benzoxazolyloxy group, oxadiazolyloxy group, pyrazolooxazolyloxy group, imidazothiazolyloxy group, thienofuranyloxy group, furopyrrolyloxy group, and pyridoxazinyloxy group. Among these, a thienyloxy group, furyloxy group, pyridyloxy group, pyrimidinyloxy group and pyrazinyloxy group are preferable.

The "3- to 8-membered ring nonaromatic heterocyclic group" refers to a monocyclic, bicyclic or tricyclic 3- to 8-membered nonaromatic heterocyclic group that contains at least one: nitrogen atom.

In the formula (I), when R represents "RdRd'N—", the "3- to 8-membered ring nitrogen-containing nonaromatic heterocyclic group" is formed of the Rd and the Rd', and a nitrogen atom.

Examples of the "3- to 8-membered ring nitrogen-containing nonaromatic heterocyclic group" include an aziridinyl group, azetidinyl group, pyrrolidinyl group, pyrrolyl group, piperidinyl group, piperazinyl group, imidazolyl group, pyrazolidinyl group, imidazolidinyl group, morpholinyl group, thiomorpholinyl group, imidazolinyl group, oxazolinyl group and quinuclidinyl group.

The "amino group" means a group represented by a formula —$NH_2$.

The substituent of the phrase "may have a substituent" includes one or more groups selected from (1) a halogen atom, (2) a hydroxy group, (3) a thiol group, (4) a nitro group, (5) a nitroso group, (6) a cyano group, (7) a carboxyl group, (8) a hydroxysulfonyl group, (9) an amino group, (10) a $C_{1-12}$ alkyl group (for example, a methyl group, ethyl group, n-propyl group, iso-propyl group, n-butyl group, iso-butyl group, sec-butyl group, and tert-butyl group), (11) an unsaturated $C_{2-12}$ alkyl group (for example, a vinyl group, allyl group, 1-propenyl group, 2-propenyl group, isopropenyl group, ethynyl group, 1-propynyl group, 2-propynyl group, 1-butynyl group, 2-butynyl group, 3-butynyl group, and 3-methyl-1-propynyl group), (12) a $C_{6-14}$ aryl group (for example, a phenyl group, 1-naphthyl group, and 2-naphthyl group), (13) a 5- to 14-membered ring heteroaryl group (for example, a thienyl group, furyl group, pyridyl group, pyridazinyl group, pyrimidinyl group, and pyrazinyl group), (14) a 3- to 14-membered ring nonaromatic heterocyclic group (for example, an aziridinyl group, azetidinyl group, pyrrolidinyl group, pyrrolyl group, piperidinyl group, piperazinyl group, imidazolyl group, pyrazolidinyl group, imidazolidinyl group, morpholinyl group, thiomorpholinyl group, imidazolinyl group, oxazolinyl group, and quinuclidinyl group), (15) a $C_{3-14}$ cycloalkyl group (for example, a cyclopropyl group, cyclobutyl group, cyclopentyl group, cyclohexyl group, cycloheptyl group and cyclooctyl group), (16) a $C_{1-12}$ alkoxy group (for example, a methoxy group, ethoxy group, n-propoxy group, iso-propoxy group, sec-propoxy group, n-butoxy group, iso-butoxy group, sec-butoxy group and tert-butoxy group), (17) a $C_{6-14}$ aryloxy group (for example, a phenyloxy group, 1-naphthyloxy group and 2-naphthyloxy group), (18) a $C_{7-16}$ aralkyloxy group (for example, benzyloxy group, phenethyloxy group, 3-phenylpropyloxy group, 4-phenylbutyloxy group, 1-naphthylmethyloxy group and 2-naphthylmethyloxy group) (19) a 5- to 14-membered ring heteroaralkyloxy group (for example, a thienylmethyloxy group, furylmethyloxy group, pyridylmethyloxy group, pyridazinylmethyloxy group, pyrimidinylmethyloxy group and pyrazinylmethyloxy group), (20) a 5- to 14-membered ring heteroaryloxy group (for example, a thienyloxy group, furyloxy group, pyridyloxy group, pyridazinyloxy group, pyrimidinyloxy group and pyrazinyloxy group) (21) an aliphatic $C_{1-12}$ acyl group (for example, an acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonyl group, iso-crotonoyl group, oleoyl group and linolenoyl group), (22) an aromatic $C_{7-15}$ acyl group (for example, a benzoyl group, 1-naphthoyl group and 2-naphthoyl group), (23) an aliphatic $C_{2-12}$ acyloxy group (for example, acetoxy group, propionyloxy group and acryloxy group), (24) a $C_{2-12}$ alkoxycarbonyl group (for example, a methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group and tert-butoxycarbonyl group), (25) an unsaturated $C_{3-12}$ alkoxycarbonyl group (a vinyloxycarbonyl group, allyloxycarbonyl group, 1-propenyloxycarbonyl group, 2-propenyloxycarbonyl group, isopropenyloxycarbonyl group, propargyloxycarbonyl group and 2-butynyloxycarbonyl group), (26) a $C_{1-12}$ alkylthio group (for example, a methylthio group, ethylthio group, n-propylthio group and iso-propylthio group), (27) a $C_{1-12}$ alkylsulfinyl group (for example, a methylsulfinyl group, ethylsulfinyl group, n-propylsulfinyl group and iso-propylsulfinyl group), (28) a $C_{1-12}$ alkylsulfonyl group (for example, a methylsulfonyl group, ethylsulfonyl group, n-propylsulfonyl group and iso-propylsulfonyl group), (29) a $C_{6-14}$ arylsulfonyl group (for example, a benzenesulfonyl group, 1-naphthalenesulfonyl group and 2-naphthalenesulfonyl group), (30) a $C_{1-12}$ alkylsulfonyloxy group (for example, a methylsulfonyloxy group, ethylsulfonyloxy group, n-propylsulfonyloxy group and iso-propylsulfortyloxy group), (31) a carbamoyl group, (32) a 5- to 14-membered ring heteroarylthio group (for example, a pyridylthio group), (33) a $C_{7-16}$ aralkylthio group (for example, a benzylthio group), (34) an unsaturated $C_{2-12}$ alkoxy group, and the like.

When the group which "may have a substituent" is a $C_{1-12}$ alkyl group, unsaturated $C_{1-12}$ alkyl group, $C_{1-12}$ alkoxy group, or unsaturated $C_{1-12}$ alkoxy group, these groups can have substituents mentioned above other than the (10) $C_{1-12}$ alkyl group and the (11) unsaturated $C_{1-12}$ alkyl group.

In addition, the (9) amino group and the (31) carbamoyl group mentioned as the substituent of the phrase "may have a substituent" may be further substituted with one or two of a $C_{1-12}$ alkyl group, unsaturated $C_{2-12}$ alkyl group or $C_{6-14}$ aryl group.

Among the above-mentioned substituents, (1) a halogen atom, (2) a hydroxy group, (3) a thiol group, (4) a nitro group, (6) a cyano group, (7) a carboxyl group, (8) a hydroxysulfonyl group, (9) an amino group, (10) a $C_{1-12}$ alkyl group, (16) a $C_{1-12}$ alkoxy group, (21) an aliphatic $C_{1-12}$ acyl group, (23) an aliphatic $C_{2-12}$ acyloxy group, (26) a $C_{1-12}$ alkylthio group and (31) a carbamoyl group are more preferable.

<Synthesis Method>

The 16-membered macrolide derivatives, which are an active ingredient of the anti-penicillin resistant pneumococci agent of the present invention, are compounds that have common feature that the hydroxy group at C-23 of 3,4'-dideoxymycaminosyltylonolide represented by the formula (I) is substituted.

These tylonolide derivatives (or compounds) can be synthesized using 3,4'-dideoxymycaminosyltylonolide disclosed in JP-A No. 02-275894 as a starting material by means of a general organic synthetic means.

Production methods of halogen derivatives, azido derivatives, ester derivatives, amide derivatives, ether derivatives, urethane derivatives, urea derivatives, thiourea derivatives, thioether derivatives, and amine derivatives will be described below.

(A) Production Method of Halogen Derivatives

The halogen derivatives can be prepared by protecting previously the 20-formyl group of or both the oxo group at $C_{1-9}$ and the 20-formyl group of 3,4'-dideoxymycaminosyltylonolide as a starting compound with an appropriate protecting group, followed by halogenation of the hydroxy group at C-23, and then removing the protecting group.

Halogenation reaction can be performed, for example, by treating the protected derivative with diethylaminosulfur trifluoride (DAST) or with carbon tetrabromide, bromine, phosphorus tribromide, iodine or carbon tetrachloride in the presence of triphenylphosphine and a base. The base used herein includes general organic bases and inorganic bases such as diisopropylethylamine, dimethylaminopyridine, triethylamine, pyridine, 2,6-lutidine, and sodium hydride. The solvent used in the reaction is not particularly limited, but those that do not easily react with a starting material are desirable. Examples thereof include tetrahydrofuran, dichloromethane and N,N-dimethylformamide. Further, chlorination can be performed, for example by treating the protected derivative with an organic sulfonyl chloride such as 2-nitrobenzenesulfonyl chloride in pyridine. In either reaction, the reaction time is from 10 minutes to 30 hours. The reaction temperature is from −78° C. to a temperature of heating under reflux.

(B) Production Method of Azido Derivatives

The azido derivatives can be prepared by replacing the halogen of the halogen derivatives with an azido group, or can be prepared by replacing the halogen of protected halogen derivatives that can be prepared by the (A) production method of halogen derivatives with an azido group and then by removing the protecting group.

Typically used azidating agents can be utilized for this azidation reaction. Preferable examples of the azidating agent include metal azides such as sodium azide and lithium azide, organosilyl azides such as trimethylsilyl azide, and quaternary ammonium azides such as tetrabutylammonium azide. The solvent used in the reaction is not particularly limited, but those that do not easily react with a starting material are desirable. For example, aprotic polar solvents such as acetonitrile, N,N-dimethylformamide, and dimethylsulfoxide are useful. The reaction time is from 10 minutes to 30 hours. The reaction temperature is from 10° C. to a temperature of heating under reflux.

(C) Production Method of Ester Derivatives

The ester derivatives can be prepared by protecting previously the 20-formyl group of or both the oxo group at C-9 and the 20-formyl group of 3,4'-dideoxymycaminosyltylonolide as a starting compound with an appropriate protecting group, or further protecting the free hydroxy group at C-2' of the protected derivative with an appropriate protecting group; followed by esterification of the hydroxy group at C-23, and then removing the protecting group.

The esterification reaction can be performed, for example by treating the protected derivative with a carboxylic acid anhydride or a carboxylic acid halide in a basic solvent such as pyridine or triethylamine. Further, this esterification reaction can also be to performed by treating the protected derivative with a desired carboxylic acid in the presence of a base and a condensing agent. The base used herein includes general organic bases such as diisopropylethylamine, dimethylaminopyridine, and triethylamine. The condensing agent used herein includes condensing agents typically used for peptide synthesis, such as 1,3-dicyclohexylcarbodiimide, N-ethyl-N'-3-dimethylaminopropylcarbodiimide and N,N-bis(2-oxo-3-oxazolidinyl)phosphinic chloride. In this case, the solvent used in the reaction is not particularly limited, but those that do not easily react with a starting material and a reagent are desirable. Examples thereof include tetrahydrofuran, dichloromethane, and acetonitrile. The reaction time is from 10 minutes to 30 hours. The reaction temperature is from −78° C. to a temperature of heating under reflux.

(D) Production Method of Amide Derivatives

The amide derivatives can be prepared by subjecting the azido derivatives, protected with a protecting group, that can be prepared by the (B) production method of azido derivatives, to reduction reaction, amidating the resulting amino group at C-23, and then removing the protecting group.

The amidation reaction can be performed by treating the protected derivative with a carboxylic acid halide or a carboxylic acid anhydride in alcohol that contains water in the presence of a base. The base used herein includes general organic bases and inorganic bases such as dimethylaminopyridine, triethylamine, sodium bicarbonate, and potassium carbonate. The reaction time is from 10 minutes to 30 hours. The reaction temperature is from 10° C. to 80° C. Further, this amidation reaction can also be performed by treating the protected derivative with a desired carboxylic acid in the presence of a base and a condensing agent, or by treating the protected derivative with an active ester of a desired carboxylic acid in the presence of a base. The base used herein includes general organic bases such as diisopropylethylamine, dimethylaminopyridine, and triethylamine. The condensing agent used herein includes condensing agents typically used for peptide synthesis, such as 1,3-dicyclohexylcarbodiimide, N-ethyl-N'-3-dimethylaminopropylcarbodiimide and N,N-bis(2-oxo-3-oxazolidinyl)phosphinic chloride. The active ester used herein includes active ester agents typically used for peptide synthesis, such as N-hydroxysuccinimide esters, para-nitrophenyl esters, and pentafluorophenyl esters.

In either case, the solvent used in the reaction is not particularly limited, but those that do not easily react with a starting material and a reagent are desirable. Examples thereof include tetrahydrofuran, dichloromethane, acetonitrile, and ethyl acetate. The reaction time is from 10 minutes to 30 hours. The reaction temperature is from −78° C. to a temperature of heating under reflux.

(E) Production Method of Ether Derivatives

The ether derivatives can be prepared by protecting previously the 20-formyl group of or both the oxo group at C-9 and the 20-formyl group of 3,4'-dideoxymycaminosyltylonolide as a starting compound with an appropriate protecting group, or further protecting the free hydroxy group at C-2' of the protected derivative with an appropriate protecting group; followed by etherification of the hydroxy group at C-23, and then removing the protecting group.

The etherification reaction can be performed by treating the protected derivative with a variety of organic halides in the presence of a base. The base used herein includes general organic bases such as diisopropylethylamine, dimethylaminopyridine, and triethylamine. The solvent used in the reaction is not particularly limited, but those that do not easily react with a starting material are desirable. Examples thereof include tetrahydrofuran, dichloromethane, acetonitrile, and N,N-dimethylformamide. The reaction time is from 30 minutes to 72 hours. The reaction temperature is from −78° C. to a temperature of heating under reflux. Further, this etherification reaction can also be performed by treating the protected derivative with an organic halide in a two-phase solution consisting of an organic solvent which is not miscible with water such as dichloromethane or carbon tetrachloride, and an aquous solution of inorganic base such as sodium hydroxide and potassium hydroxide in the presence of a phase transfer catalyst. For the phase transfer catalyst, general organic quaternary ammonium salts and phosphonium salts are used, and for example, tetrabutylammonium iodide is useful. The reaction time is from 10 minutes to 10 hours. The reaction temperature is from −78° C. to a temperature of heating under reflux. Further, this etherification reaction can also be performed by treating the protected derivative with a variety of aromatic alcohols in the presence of triphenylphosphine and azodicarboxylic acid diethyl ester. The solvent used in the reaction is not particularly limited, but those that do not easily react with a starting material are desirable. Examples thereof include tetrahydrofuran and toluene. The reaction time is from 10 minutes to 10 hours. The reaction temperature is from −30° C. to 60° C.

(F) Production Method of Urethane Derivatives

The urethane derivatives can be prepared by protecting previously the 20-formyl group of or both the oxo group at C-9 and the 20-formyl group of 3,4'-dideoxymycaminosyltylonolide as a starting compound with an appropriate protecting group, or further protecting the free hydroxy group at C-2' of the protected derivative with an appropriate protecting group; followed by conversion of the hydroxy group at C-23 to a urethane group, and then removing the protecting group.

The conversion to a urethane group can be performed by treating the protected derivative with a variety of isocyanic acid esters in the presence of a base. The base used herein includes general organic bases such as diisopropylethylamine, dimethylaminopyridine, triethylamine, pyridine, and 2,6-lutidine. The solvent used in the reaction is not particularly limited, but those that do not easily react with a starting material are desirable. Examples thereof include tetrahydrofuran, dichloromethane, acetonitrile, ethyl acetate, and toluene. The reaction time is from 10 minutes to 72 hours. The reaction temperature is from −78° C. to a temperature of heating under reflux.

(G) Production Method of Urea Derivatives

The urea derivatives can be prepared by subjecting the azido derivatives, protected with a protecting group, that can be prepared by the (B) production method of azido derivatives, to reduction reaction, followed by conversion of the resulting amino group at C-23 to a urea group, and then removing the protecting group.

The conversion to a urea group can be performed by treating the protected derivative with a variety of isocyanic esters in the presence of a base. The base used herein includes general organic bases such as diisopropylethylamine, dimethylaminopyridine, and triethylamine. The solvent used in the reaction is not particularly limited, but solvents that do not easily react with a starting material are desirable. Examples thereof include tetrahydrofuran, dichloromethane, acetonitrile, ethyl acetate, and toluene. The reaction time is from 10 minutes to 72 hours. The reaction temperature is from −78° C. to a temperature of heating under reflux.

(H) Production Method of Thiourea Derivatives

The thiourea derivatives can be prepared by subjecting the azido derivatives, protected with a protecting group, that can be prepared by the (B) production method of azido derivatives, to reduction reaction, followed by conversion of the resulting amino group at C-23 to a thiourea group, and then removing the protecting group.

The conversion to a thiourea group can be performed by treating the protected derivative with a variety of isothiocyanic esters in the presence of a base. The base used herein includes general is organic bases such as diisopropylethylamine, dimethylaminopyridine, and triethylamine. The solvent used in the reaction is not particularly limited, but those that do not easily react with a starting material are desirable. Examples thereof include tetrahydrofuran, dichloromethane, acetonitrile, ethyl acetate, and toluene. The reaction time is from 10 minutes to 72 hours. The reaction temperature is from −78° C. to a temperature of heating under reflux.

(I) Production Method of Thioether Derivatives

The thioether derivatives can be prepared by replacing the halogen of protected halogen derivatives that can be prepared by the (A) production method of halogen derivatives with various thioalcohols, and then removing a protecting group. For the halogen derivatives in this case, iodine derivatives are useful.

This thioetherification reaction can be performed by treating the protected halogen derivative with a thioalcohol in the presence of a base. Examples of the base include sodium hydride and alkyllithium. The solvent used in the reaction is not particularly limited, but those that do not easily react with a starting material are desirable; for example, tetrahydrofuran, acetonitrile, and N,N-dimethylformamide are useful. The reaction time is from 10 minutes to 30 hours. The reaction temperature is from −78° C. to a temperature of heating under reflux.

(J) Production Method of Amine Derivatives

The amine derivatives can be prepared by replacing the halogen of protected halogen derivatives that can be prepared by the (A) production method of halogen derivatives with various amines, and then removing a protecting group. For the halogen derivatives in this case, iodine derivatives are useful.

This reaction to give amine derivatives can be performed by treating the protected halogen derivative with a variety of amines in an organic solvent at a temperature ranging from 50° C. to a temperature of heating under reflux. The solvent used in the reaction is not particularly limited, but those that do not easily react with a starting material are desirable. Examples thereof include tetrahydrofuran, acetonitrile, and N,N-dimethylformamide. The reaction time is from 1 hour to 120 hours.

After completion of reaction, the objective substance of each reaction is collected from reaction mixture according to a common procedure. For example, when insoluble matter is present, the objective substance can be obtained by filtering the matter appropriately, followed by distilling off the solvent under reduced pressure. Alternatively, the objective substance can be obtained by diluting the reaction mixture with an organic solvent such as ethyl acetate, washing this with water, drying the organic layer with e.g. anhydrous magnesium sulfate and then distilling off the solvent. If necessary, further purification can be performed by a common procedure, for example column chromatography, thin-layer chromatography, high-performance liquid chromatography or recrystallization.

There are differences in antimicrobial spectrum between is respective derivatives prepared by the production methods of (A) to (J), however, the derivatives have excellent antimicrobial activity against certain penicillin-resistant *Streptococcus pneumoniae* (anti-PRSP activity).

For the derivatives prepared by the production methods of (A) to (J), R in the formula (I) is shown below together with the designated name of the corresponding derivative.

(A) Halogen Derivatives

| (R) | (Designated Name of Derivative) |
|---|---|
| —I | MKT-3001 |
| —Cl | MKT-3007 |

(B) Azido Derivatives
| (R) | (Designated Name of Derivative) |
|---|---|
| —N₃ | MKT-3004 |
(C) Ester Derivatives
| (R) | (Designated Name of Derivative) |
|---|---|
| 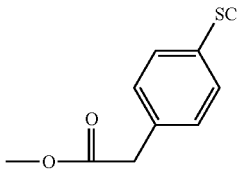 | MKT-2109 |
| 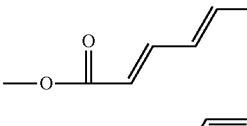 | MKT-2110 |
| 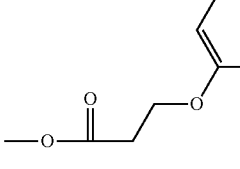 | MKT-2111 |
| 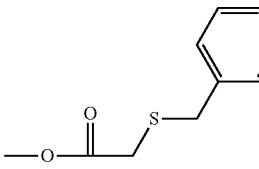 | MKT-2112 |
| 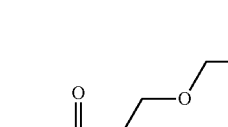 | MKT-2113 |
| 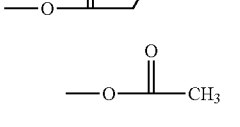 | MKT-2002 |
| 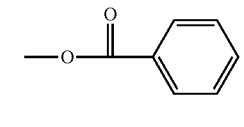 | MKT-2003 |
| 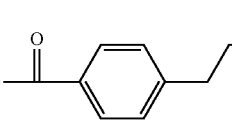 | MKT-2004 |
| 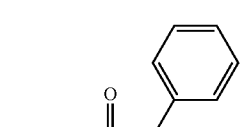 | MKT-2005 |
-continued
| (R) | (Designated Name of Derivative) |
|---|---|
| 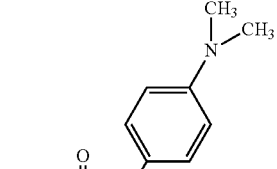 | MKT-2006 |
| 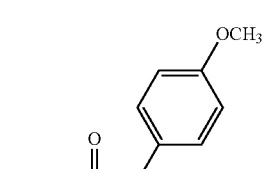 | MKT-2007 |
| 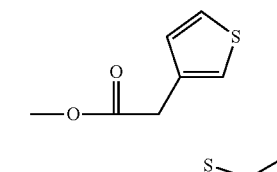 | MKT-2008 |
| 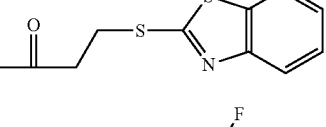 | MKT-2009 |
| 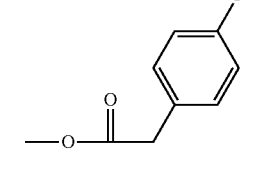 | MKT-2010 |
| 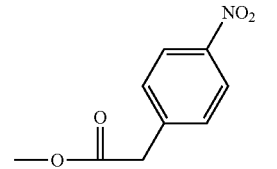 | MKT-2101 |
| 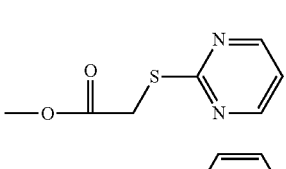 | MKT-2102 |
| 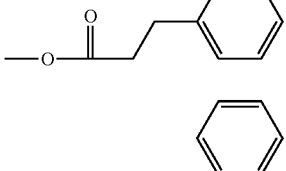 | MKT-2103 |
| 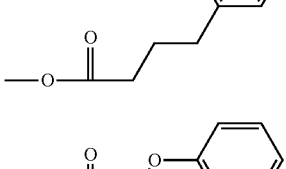 | MKT-2104 |
| 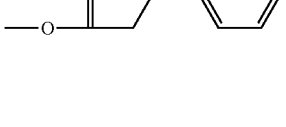 | MKT-2105 |

| (R) | (Designated Name of Derivative) |
|---|---|
| [furan acrylate structure] | MKT-2106 |
| [pyridin-2-yl acetate structure] | MKT-2107 |
| [pyridin-3-yl acetate structure] | MKT-2108 |

(D) Amide Derivatives

| (R) | (Designated Name of Derivative) |
|---|---|
| —HN-C(O)-CH₃ | MKT-3201 |
| —HN-C(O)-phenyl | MKT-3202 |
| —HN-C(O)-CH₂-phenyl | MKT-3203 |
| —HN-C(O)-pyridin-2-yl | MKT-3204 |
| —HN-C(O)-CH=CH-pyridin-3-yl | MKT-3205 |
| —HN-C(O)-O-CH₂-phenyl | MKT-3301 |
| —HN-C(O)-CH₂-C₆H₄-N(CH₃)₂ | MKT-3211 |

| (R) | (Designated Name of Derivative) |
|---|---|
| —HN-C(O)-CH₂-C₆H₄-OCH₃ | MKT-3212 |
| —HN-C(O)-CH₂-C₆H₄-SCH₃ | MKT-3213 |
| —HN-C(O)-CH₂-C₆H₄-F | MKT-3214 |
| —HN-C(O)-CH₂-C₆H₄-NO₂ | MKT-3215 |
| —HN-C(O)-CH₂-pyridin-3-yl | MKT-3216 |

(E) Ether Derivatives

| (R) | (Designated Name of Derivative) |
|---|---|
| —O-CH₂-CH=CH₂ | MKT-3701 |
| —O-CH₂-phenyl | MKT-3702 |
| —O-CH₂-O-CH₂-phenyl | MKT-3703 |
| —O-pyridin-2-yl | MKT-5701 |

| (R) | (Designated Name of Derivative) |
|---|---|
| 3-(N,N-dimethylamino)phenoxy group | MKT-5704 |
| 3-methoxyphenoxy group (phenyl-O-) | MKT-5705 |

(F) Urethane Derivatives

| (R) | (Designated Name of Derivative) |
|---|---|
| —O—C(=O)—NH—CH₂—CH=CH₂ | MKT-1001 |
| —O—C(=O)—NH—CH₂—C₆H₅ | MKT-1002 |
| —O—C(=O)—NH—C₆H₅ | MKT-1003 |
| —O—C(=O)—NH—CH₂CH₂—C₆H₅ | MKT-1004 |
| —O—C(=O)—NH—(4-biphenyl) | MKT-1005 |
| —O—C(=O)—NH—(R)-CH(CH₃)(C₆H₅) | MKT-1006 |
| —O—C(=O)—NH—(4-phenoxyphenyl) | MKT-1007 |
| —O—C(=O)—NH—(4-benzyloxyphenyl) | MKT-1008 |

| (R) | (Designated Name of Derivative) |
|---|---|
| —O—C(=O)—NH—(S)-CH(CH₃)(C₆H₅) | MKT-1009 |
| —O—C(=O)—NH—cyclohexyl | MKT-1010 |
| —O—C(=O)—NH—CH₂—(4-methoxyphenyl) | MKT-1011 |
| —O—C(=O)—NH—(4-(N,N-dimethylamino)phenyl) | MKT-1012 |
| —O—C(=O)—NH—(CH₂)₅—CH₃ | MKT-1013 |
| —O—C(=O)—NH—(3,5-dimethylphenyl) | MKT-1014 |
| —O—C(=O)—NH—(4-propylphenyl) | MKT-1015 |
| —O—C(=O)—NH—(4-propoxyphenyl) | MKT-1016 |
| —O—C(=O)—NH—(4-methylthiophenyl) | MKT-1017 |

(G) Urea Derivatives

| (R) | (Designated Name of Derivative) |
|---|---|
| —HN—C(=O)—NH—CH₂—C₆H₅ | MKT-3401 |

(H) Thiourea Derivatives
| (R) | (Designated Name of Derivative) |
|---|---|
| 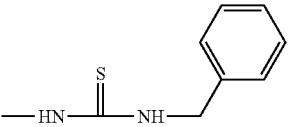 | MKT-3501 |
(I) Thioether Derivatives
| (R) | (Designated Name of Derivative) |
|---|---|
| 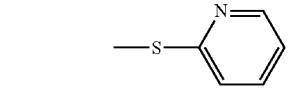 | MKT-3003 |
| 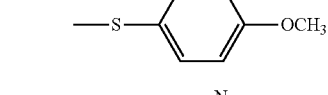 | MKT-3801 |
| 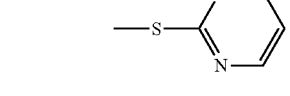 | MKT-3802 |
| 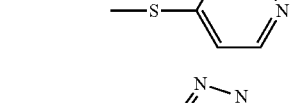 | MKT-5801 |
| 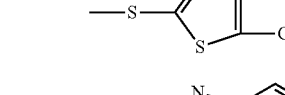 | MKT-5802 |
| 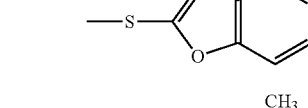 | MKT-5803 |
| 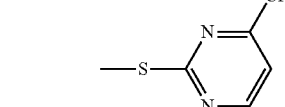 | MKT-5804 |
| 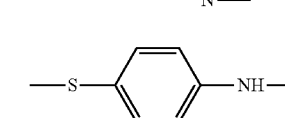 | MKT-5805 |
| 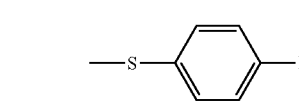 | MKT-5806 |
| 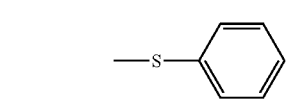 | MKT-5807 |
| 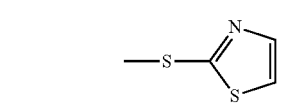 | MKT-5808 |
| 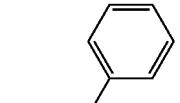 | MKT-5809 |
| 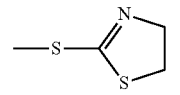 | MKT-5810 |
| 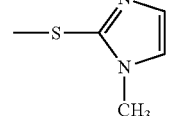 | MKT-5811 |
| 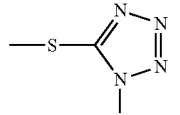 | MKT-5812 |
| 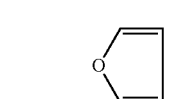 | MKT-5813 |
| 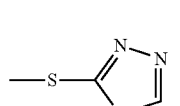 | MKT-5814 |
(J) Amine Derivatives
| (R) | (Designated Name of Derivative) |
|---|---|
| —NH$_2$ | MKT-3005 |
| 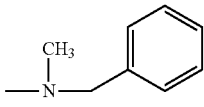 | MKT-3002 |
| 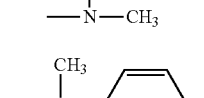 | MKT-3101 |
| 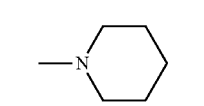 | MKT-3102 |
|  | MKT-6101 |

| (R) | (Designated Name of Derivative) |
|---|---|
| 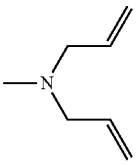 | MKT-6102 |
| 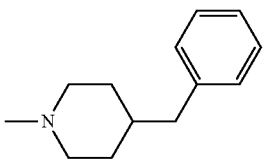 | MKT-6103 |
| 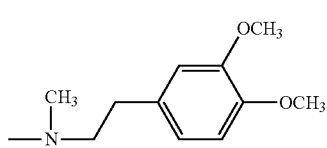 | MKT-6104 |
| 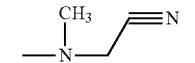 | MKT-6105 |
| 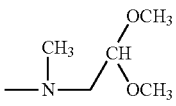 | MKT-6106 |
| 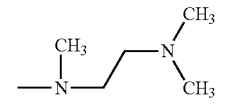 | MKT-6107 |
| 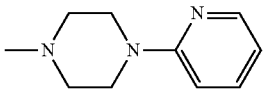 | MKT-6108 |
| 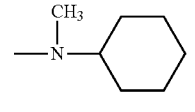 | MKT-6109 |
| 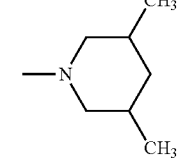 | MKT-6110 |
| 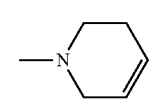 | MKT-6111 |
| 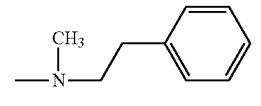 | MKT-6112 |
| 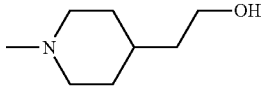 | MKT-6113 |
| 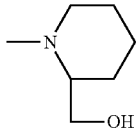 | MKT-6114 |
| 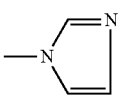 | MKT-6115 |

In particular, among these compounds, preferable compounds as an active ingredient of anti-PRSP agent that have a high anti-PRSP activity are MKT-1001, MKT-1002, MKT-2002, MKT-2007, MKT-3002, MKT-3003, MKT-3102, MKT-3202, MKT-3203, MKT-3301, MKT-3701, MKT-3703, MKT-3802, MKT-2107, and MKT-2108.

The anti-penicillin resistant pneumococci agent of the present invention that contains a 16-membered macrolide derivative as an active ingredient is not particularly limited and may be any dosage form as long as it is appropriate for the intended use. For example, when the agent is used for a human, the agent is prepared into an oral agent, suppository, local external preparation, or injections, but is not limited to these.

In addition, the anti-penicillin resistant pneumococci agent is prepared using a diluent or excipient such as commonly used fillers, extenders, binders, disintegrants, surfactants and lubricants together with the 16-membered macrolide derivative by means of a common procedure.

Examples of the dosage form include tablets, pills, suppositories, injections, ointments, gels, gel creams, liquid medicines, powders, granules, capsules, and syrups.

When the anti-penicillin resistant pneumococci agent is formulated as a tablet, various carriers known in the art can be employed; examples thereof include excipients such as lactose, sucrose, sodium chloride, glucose, urea, starch, calcium carbonate, kaolin, crystalline cellulose, and silicic acid; binders such as water, ethanol, propanol, syrup, liquid glucose, liquid starch, gelatin solution, carboxymethylcellulose, shellac, methylcellulose, potassium phosphate, and polyvinylpyrrolidone; disintegrants such as dried starch, sodium alginate, agar powder, laininaran powder, sodium bicarbonate, calcium carbonate, polyoxyethylene sorbitan fatty acid esters, sodium lauryl sulfate, stearic acid monoglyceride, starch, and lactose; disintegration inhibitors such as sucrose, cacao butter, and hydrogenated oil; absorption promoters such as quaternary ammonium base and sodium lauryl sulfate; humectants such as glycerin and starch; adsorbents such as starch, lactose, kaolin, bentonite, and colloidal silicic acid; and lubricants such as purified talc, stearic acid salts, boric add powder, and polyethylene glycol. If to required, tablets may be further coated with the usual coating materials to make sugar-coated tablets, gelatin film-coated tablets, tablets coated with enteric coatings, tablets coated with films or double-layer tablets or multi-layer tablets, for example.

When the anti-penicillin resistant pneumococci agent is is formulated as a suppository, a base for suppository used is appropriately selected from those known in the art, specifically, lipophilic bases, water-soluble bases, and emulsion bases. Examples of the base for suppository include synthetic greasy bases such as cacao butter, hydrogenated peanut oil, and hydrogenated cocoanut oil, and water-soluble bases such as polyethylene glycols, Tween, and Pluronic.

When the anti-penicillin resistant pneumococci agent is formulated as a liquid medicine, emulsion, or suspension, various diluents known in this field can be employed. Examples thereof include water, aqueous lactic acid solution, ethyl alcohol, propylene glycol, and polyoxyethylene sorbitan fatty acid esters. In this case, adequate amounts of sodium chloride, glucose or glycerin to prepare isotonic solution may be added to a medicinal preparation. Further, the usual solubilizing agents, buffering agents, and soothing agents may be added.

When prepared as injections, liquid medicines, emulsions and suspensions are sterilized and are preferably isotonic to blood.

Typical bases for preparing the liquid medicines and gels include lower alkanols or a combination of water and surfactant, and further include water-soluble polymers. Preferable surfactants that can be used are nonionic surfactants. Specific examples thereof include polyoxyethylene sorbitan acyl esters such as Polysorbate 80, Polysorbate 60, and Polysorbate 20, and silicone/polyether copolymers such as dimethylsiloxane/methyl (POE) siloxane copolymers; polyoxyethylene acyl esters such as polyoxyl stearate 40 and polyoxyethylene lauryl ether; polyoxyethylene alcohol ethers such as lauromacrogol; glyceryl stearates such as glyceryl monostearate and decaglyceryl monolaurate; sorbitan fatty acid esters such as span 60 monostearate; sorbitan acyl esters such as sorbitan sesquioleate; polyoxy hydrogenated castor oils such as HCO-60 and HCO-50; polyoxyethylene propylene glycol monofatty acid esters such as Pluronic F68. These nonionic surfactants may be used alone or in combination of two or more in an appropriate proportion.

The water-soluble polymer compound may be either a naturally occurring or a synthetic polymer compound. Examples thereof include soluble polysaccharides such as acacia gum, xanthan gum, pectin, carrageenan, and sodium alginate; soluble polypeptides such as gelatin; and chitins such as chitin and chitosan. The synthetic polymer compound include polymers prepared by partial chemical modification of naturally occurring polymer compounds, for example, soluble polysaccharides such as sodium carboxymethyl cellulose and hydroxypropyl cellulose. Pure synthetic polymer compounds include polyvinyl alcohol compounds such as polyvinyl alcohol and derivatives thereof, and polyvinyl pyrrolidone compounds such as polyvinylpyrrolidone and derivatives thereof.

When the anti-penicillin resistant pneumococci agent is prepared as an ointment, examples of the base for ointment used include those conventional in the art such as higher fatty acids and their esters, waxes, surfactants, higher alcohols, silicone oils, water, absorption promoters, and humectants.

The active ingredients can be compounded into the anti-penicillin resistant pneumococci agent of the present invention, which is prepared as mentioned above, and the content thereof is adjusted depending on the dosage form.

The amount of the anti-penicillin resistant pneumococci agent to be administered should be determined by a doctor considering its administration route and the state of a patient (symptom, age, etc.). In the case of oral administration to adults, in general, 50 mg to 800 mg of active ingredient can be administered at one time, and once to 3 times per day, and 200 mg to 1000 mg per day.

The anti-penicillin resistant pneumococci agent and novel 16-membered macrolide derivative of the present invention can also be represented as follows.

[1] An anti-penicillin resistant pneumococci agent that comprises as an active ingredient a compound represented by formula (I) or a pharmacologically acceptable salt thereof, or hydrates thereof.

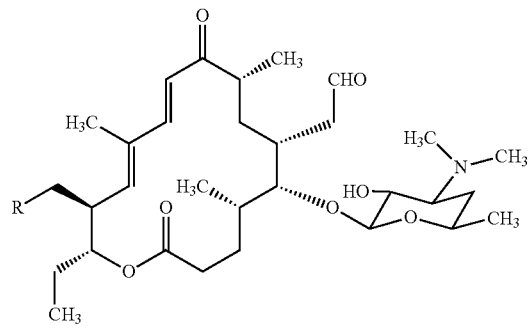

(I)

In the above formula,
R represents:
(1) a halogen atom;
(2) an azido group;
(3) Ra-Wa- (where Wa represents
   a) —CO—O— or
   b) —CO—NH—, and
Ra represents
   a) a hydrogen atom,
   b) a $C_{1-12}$ alkyl group that may have a substituent,
   c) an unsaturated $C_{2-12}$ alkyl group that may have a substituent,
   d) a $C_{6-14}$ aryl group that may have a substituent,
   e) a 5- to 14-membered ring heteroaryl group that may have a substituent,
   f) a $C_{7-16}$ aralkyl group that may have a substituent,
   g) a 5- to 14-membered ring heteroaralkyl group that may have a substituent,
   h) a $C_{1-12}$ alkoxy group that may have a substituent,
   i) an unsaturated $C_{2-12}$ alkoxy group that may have a substituent,
   j) a $C_{6-14}$ aryloxy group that may have a substituent, or
   k) a 5- to 14-membered ring heteroaryloxy group that may have a substituent);
(4) Rb-Wb-(where Wb represents —O—, and
Rb represents
   a) a $C_{1-12}$ alkyl group that may have a substituent,
   b) an unsaturated $C_{2-12}$ alkyl group that may have a substituent,
   c) a $C_{6-14}$ aryl group that may have a substituent,
   d) a 5- to 14-membered ring heteroaryl group that may have a substituent,
   e) a $C_{7-16}$ aralkyl group that may have a substituent, or
   f) a 5- to 14-membered ring heteroaralkyl group that may have a substituent); or
(5) Rc-Wc—(where Wc represents
   a) —NH—CO—O—,
   b) —NH—CO—NH—,
   c) —NH—CS—NH— or
   d) —S—, and
Rc represents
   a) a hydrogen atom,
   b) a $C_{1-12}$ alkyl group that may have a substituent,
   c) an unsaturated $C_{2-12}$ alkyl group that may have a substituent, d) a $C_{6-14}$ aryl group that may have a substituent,
e) a 5- to 14-membered ring heteroaryl group that may have a substituent,
f) a $C_{7-16}$ aralkyl group that may have a substituent, or
g) a 5- to 14-membered ring heteroaralkyl group that may have a substituent); or (6) RdRd'N— (where Rd and Rd' may be the same or different and represent
a) a hydrogen atom
b) a $C_{1-12}$ alkyl group that may have a substituent,
c) an unsaturated $C_{2-12}$ alkyl group that may have a substituent,
d) a $C_{6-14}$ aryl group that may have a substituent,
e) a 5- to 14-membered ring heteroaryl group that may have a substituent,
f) a $C_{7-16}$ aralkyl group that may have a substituent, or
g) a 5- to 14-membered ring heteroaralkyl group that may have a substituent or
h) a 3- to 8-membered ring nonaromatic heterocyclic group that may have a substituent, which nonaromatic heterocyclic group the Rd and the Rd' together form).

[2] An anti-penicillin resistant pneumococci agent that comprises as an active ingredient a compound represented by the formula (I) or a pharmacologically acceptable salt thereof, or hydrates thereof, wherein, in the formula (I), R is:
(1) an azido group;
(2) Ra1-Wa1—(where Wa1 represents
a) —CO—O— or
b) —CO—NH—, and
Ra1 represents
a) a $C_{1-12}$ alkyl group that may have a substituent,
b) a $C_{6-14}$ aryl group that may have a substituent,
c) a 5- to 14-membered ring heteroaryl group that may have a substituent,
d) a $C_{7-16}$ aralkyl group that may have a substituent, or
e) a $C_{1-12}$ alkoxy group that may have a substituent);
(3) Rb1-Wb1-(where Wb1 represents —O—, and Rb1 represents
a) a $C_{1-12}$ alkyl group that may have a substituent,
b) an unsaturated $C_{2-12}$ alkyl group that may have a substituent, or
c) a $C_{7-16}$ aralkyl group that may have a substituent);
(4) Rc1-Wc1-(where Wc1 represents
a) —NH—CO—O—,
b) —NH—CO—NH—, or
c) —S—, and
Rc1 represents
a) an unsaturated $C_{2-12}$ alkyl group that may have a substituent,
b) a 5- to 14-membered ring heteroaryl group that may have a substituent, or
c) a $C_{7-16}$ aralkyl group that may have a substituent); or
(5) Rd1Rd1'N— (where Rd1 and Rd1' may be the same or different and represent
a) a $C_{1-12}$ alkyl group that may have a substituent, or
b) a $C_{6-14}$ aryl group that may have a substituent).

[3] An anti-penicillin resistant pneumococci agent that comprises as an active ingredient the compound according to the [1] or [2] or a pharmacologically acceptable salt thereof, or hydrates thereof, wherein, in the formula (I), R is one group selected from the group consisting of

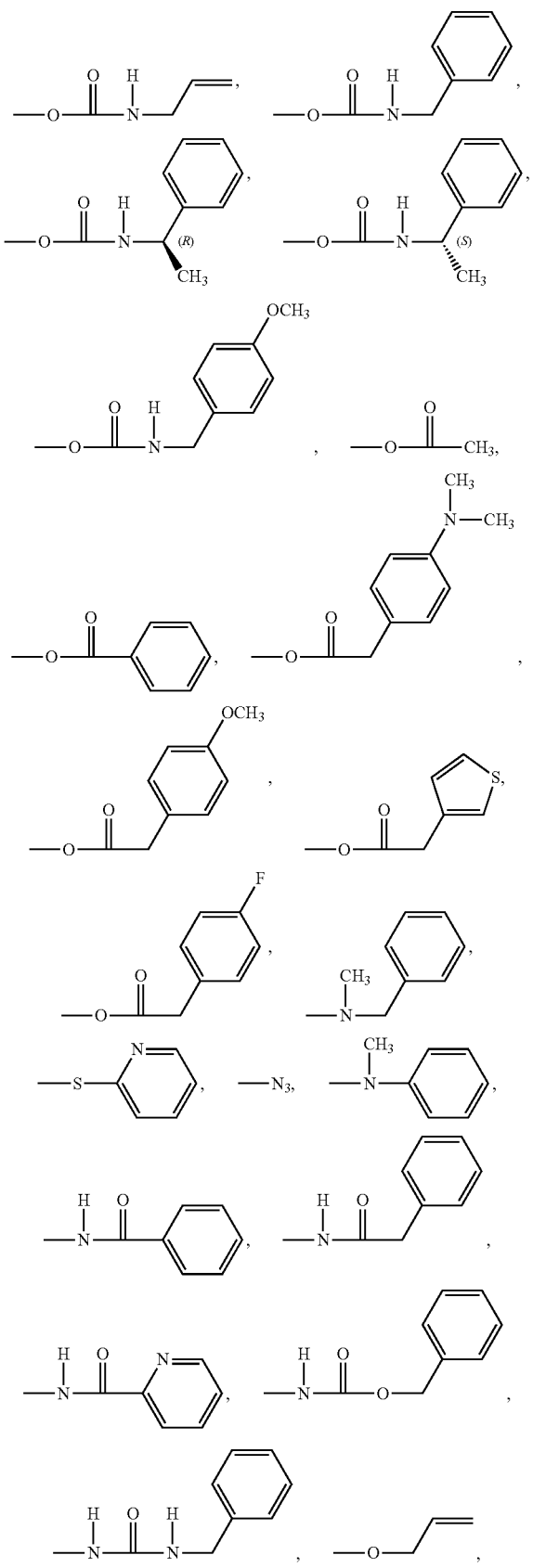

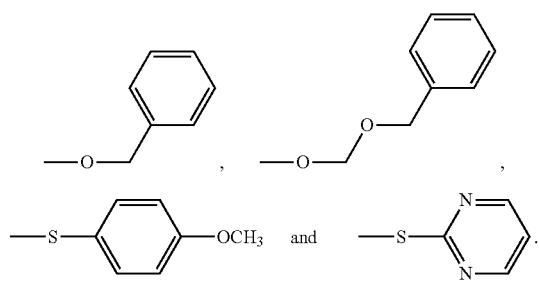

[4] An anti-penicillin resistant pneumococci agent that comprises as an active ingredient the compound according to the [1] or [2] or a pharmacologically acceptable salt thereof, or hydrates thereof, wherein, in the formula (I), R is one group selected from the group consisting of

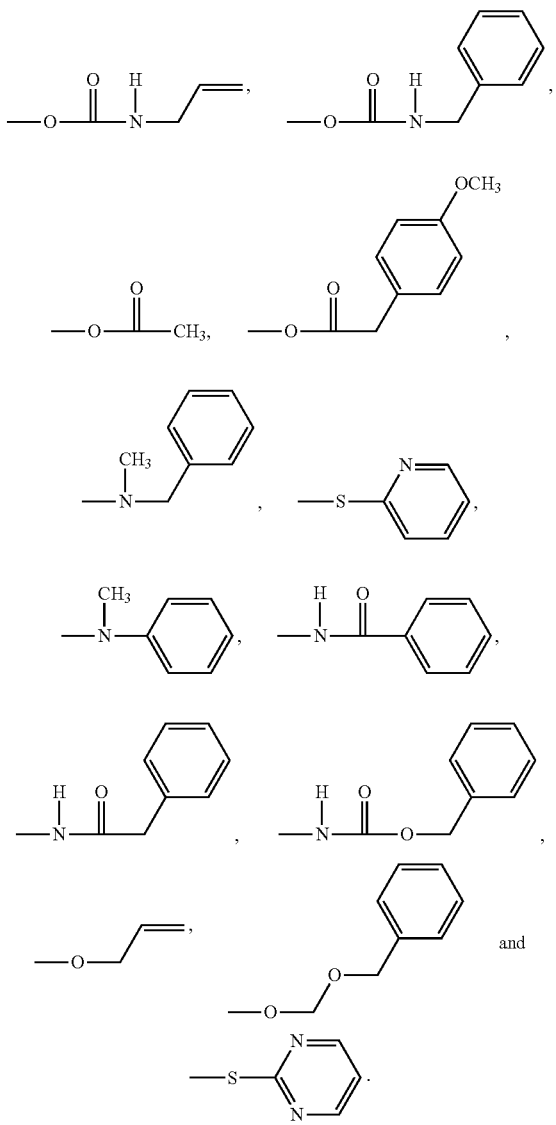

[5] A compound represented by formula (II) or a pharmacologically acceptable salt thereof, or hydrates thereof.

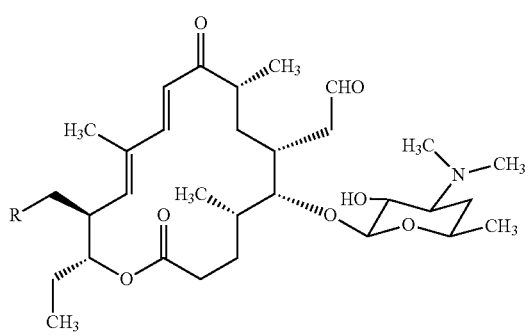

(II)

In the above formula,
R represents:
(1) an azido group;
(2) Rp-Wp— (where Wp represents —CO—O—, and
Rp represents
   a) a $C_{7-16}$ aralkyl group that has a substituent,
   b) a 5- to 14-membered ring heteroaryl group that may have a substituent, or
   c) a 5- to 14-membered ring heteroaralkyl group that may have a substituent);
(3) Rq-Wq— (where Wq represents —CO—NH—, and
Rq represents
   a) a hydrogen atom
   b) a $C_{1-12}$ alkyl group that may have a substituent,
   c) an unsaturated $C_{2-12}$ alkyl group that may have a substituent,
   d) a $C_{6-14}$ aryl group that may have a substituent,
   e) a 5- to 14-membered ring heteroaryl group that may have a substituent,
   f) a $C_{7-16}$ aralkyl group that may have a substituent,
   g) a 5- to 14-membered ring heteroaralkyl group that may have a substituent,
   h) a $C_{1-12}$ alkoxy group that may have a substituent,
   i) an unsaturated $C_{2-12}$ alkoxy group that may have a substituent,
   j) a $C_{6-14}$ aryloxy group that may have a substituent, or
   k) a 5- to 14-membered ring heteroaryloxy that may have a substituent group);
(4) Rr-Wr— (where Wr represents —O—, and
Rr represents
   a) a $C_{1-12}$ alkyl group that may have a substituent,
   b) an unsaturated $C_{2-12}$ alkyl group that may have a substituent,
   c) a $C_{6-14}$ aryl group that may have a substituent,
   d) a 5- to 14-membered ring heteroaryl group that may have a substituent,
   e) a $C_{7-16}$ aralkyl group that may have a substituent, or
   f) a 5- to 14-membered ring heteroaralkyl group that may have a substituent);
(5) Rs-Ws— (where Ws represents
   a) —NH—CO—O—,
   b) —NH—CO—NH—,
   c) —NH—CS—NH— or
   d) —S—, and
Rs represents
   a) a hydrogen atom,
   b) a $C_{1-12}$ alkyl group that may have a substituent,
   c) an unsaturated $C_{2-12}$ alkyl group that may have a substituent,
   d) a $C_{6-14}$ aryl group that may have a substituent, e) a 5- to 14-membered ring heteroaryl group that may have a substituent,
f) a $C_{7-16}$ aralkyl group that may have a substituent, or
g) a 5- to 14-membered ring heteroaralkyl group that may have a substituent); or
(6) RtRt'N-(where Rt and Rt' may be the same or different and represent
   a) a hydrogen atom,
   b) a $C_{1-12}$ alkyl group that may have a substituent,
   c) an unsaturated $C_{2-12}$ alkyl group that may have a substituent,
   d) a $C_{6-14}$ aryl group that may have a substituent,
   e) a 5- to 14-membered ring heteroaryl group that may have a substituent,
   f) a $C_{7-16}$ aralkyl group that may have a substituent,
   g) a 5- to 14-membered ring heteroaralkyl group that may have a substituent, or
   h) a 3- to 8-membered ring nonaromatic heterocyclic group that may have a substituent, which nonaromatic heterocyclic group the Rt and the Rt' together form, however, the Rt and the Rt' do not represent a methyl group simultaneously.).

[6] A compound represented by the formula (II) or a pharmacologically acceptable salt thereof, or hydrates thereof, wherein, in the formula (II), R is:
   (1) an azido group;
   (2) Rp1-Wp1-(where Wp1 represents —CO—O—, and Rp1 represents
      a) a $C_{7-16}$ aralkyl group that has a substituent, or
      b) a 5- to 14-membered ring heteroaryl group that may have a substituent;
   (3) Rq1-Wq1-(where Wq1 represents —CO—NH—, and Rq1 represents
      a) a $C_{1-12}$ alkyl group that may have a substituent,
      b) a $C_{6-14}$ aryl group that may have a substituent,
      c) a 5- to 14-membered ring heteroaryl group that may have a substituent,
      d) a $C_{7-16}$ aralkyl group that may have a substituent, or
      e) a $C_{1-12}$ alkoxy group that may have a substituent);
   (4) Rr1-Wr1-(where Wr1 represents —O—, and Rr1 represents
      a) a $C_{1-12}$ alkyl group that may have a substituent,
      b) an unsaturated $C_{2-12}$ alkyl group that may have a substituent, or
      c) a $C_{7-16}$ aralkyl group that may have a substituent);
   (5) Rs1-Ws1-(where Ws1 represents
      a) —NH—CO—O—,
      b) —NH—CO—NH— or
      c) —S—, and
   Rs1 represents
      a) a $C_{1-12}$ alkyl group that may have a substituent,
      b) an unsaturated $C_{2-12}$ alkyl group that may have a substituent,
      c) a 5- to 14-membered ring heteroaryl group that may have a substituent, or
      d) a $C_{7-16}$ aralkyl group that may have a substituent); or
   (6) Rt1Rt1'N-(where Rt1 and Rt1' may be the same or different and represent
      a) a $C_{1-12}$ alkyl group that may have a substituent,
      b) a $C_{6-14}$ aryl group that may have a substituent, or
      c) a $C_{7-16}$ aralkyl group that may have a substituent, however, Rt1 and
   Rt1' do not represent a methyl group simultaneously.).

[7] A compound according to the [5] and [6] or a pharmacologically acceptable salt or hydrates, thereof, wherein, in the formula (II) R is one group consisting of

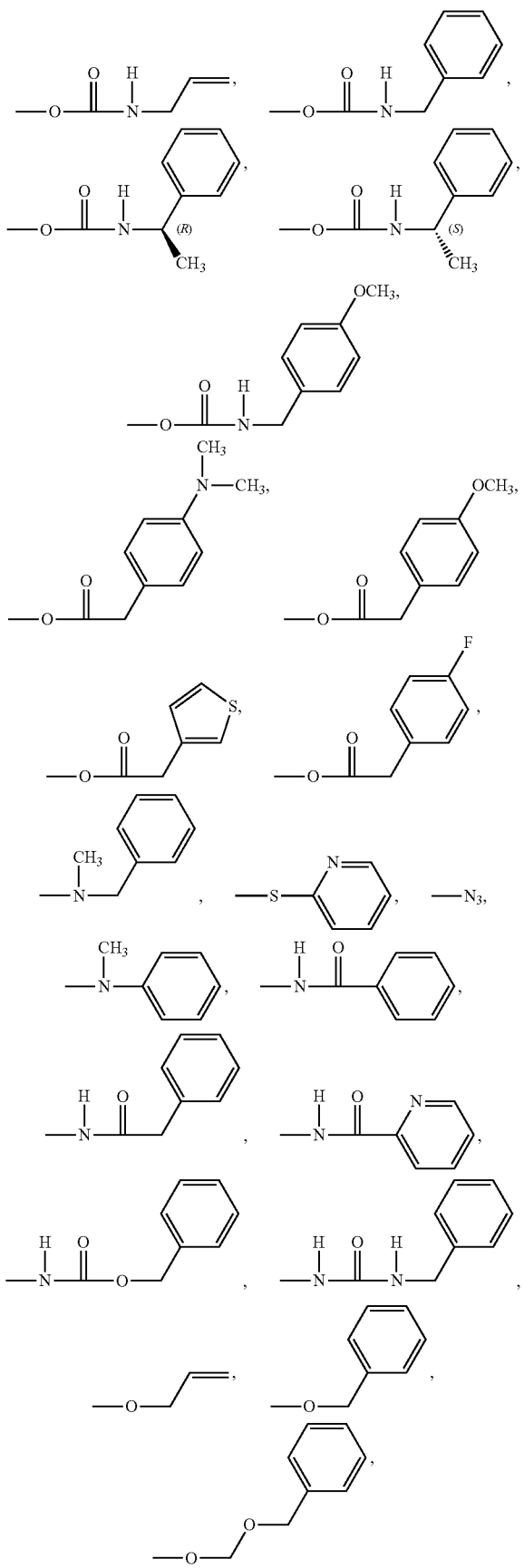

-continued

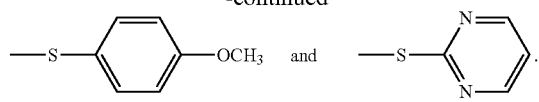

[8] A compound according to the [5] or [6] or a pharmacologically acceptable salt thereof, or hydrates thereof, wherein, in the formula (H), R is one group selected from the group consisting of

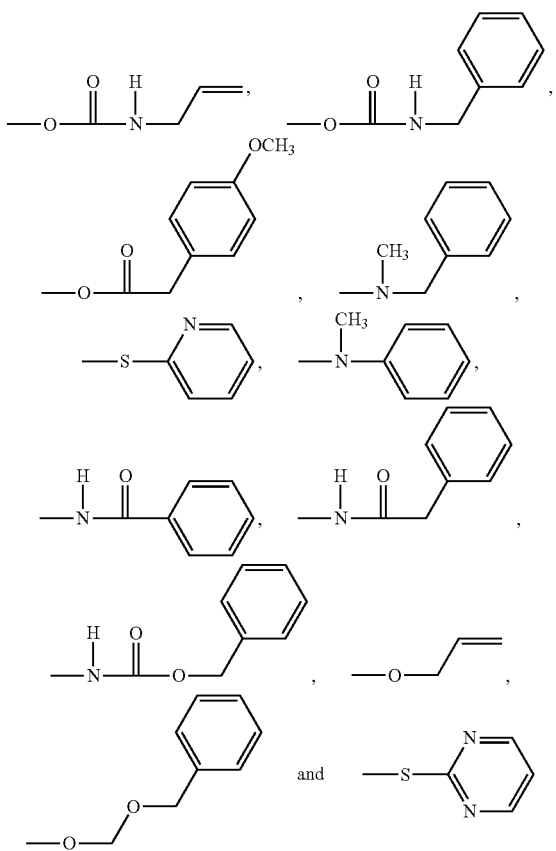

EXAMPLE

Hereinafter, Examples of the present invention will be described, which however shall not be construed as limiting the present invention thereto.

Reference Example 1

Production of 2'-O-acetyl-3,4'-dideoxymycaminosyl-tylonolide Dimethylacetal

Using 3,4'-dideoxymycaminosyltylonolide as a starting compound, a compound (Compound (1) in the following reaction formula) was produced by the method described in Carbohydrate Research 274 (1995) 269-278. 10.0 g of Compound (1) was dissolved in 200 mL of acetonitrile, 2.3 mL of acetic anhydride was added to this solution and allowed to react at room temperature for 2 hours. The reaction solution was concentrated and the syrup obtained was extracted with chloroform. The organic layer was washed with 5% aqueous sodium hydrogen carbonate solution and water, successively, dried with anhydrous sodium sulfate, and then concentrated to give 10.5 g of 2'-O-acetyl-3,4'-dideoxymycaminosyltylonolide dimethylacetal (Compound (2) in the following reaction formula) as a colorless solid. The yield was 98%. Reaction formula is shown below.

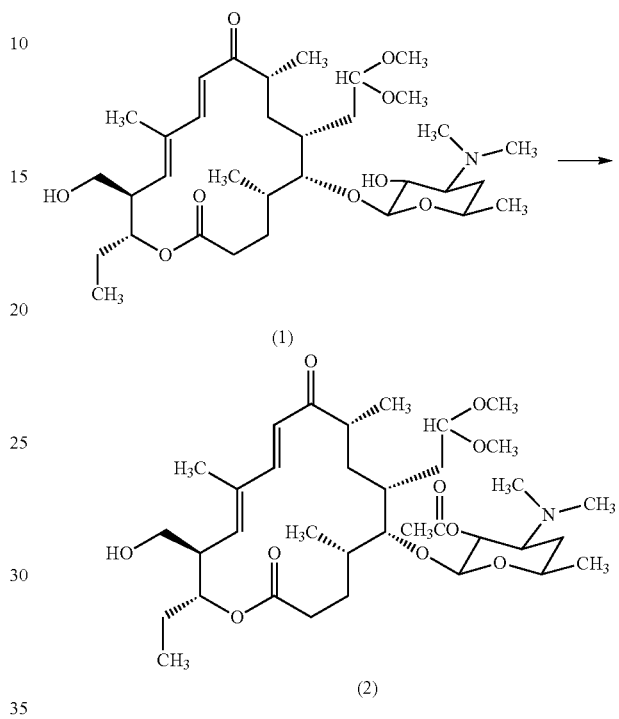

The analytical values of Compound (2) obtained are shown below: $^1$H-NMR (deuteriochloroform): δ 0.92 (3H, d, H-18), 0.94 (3H, t, H-17), 1.20 (3H, d, H-21), 1.24 (3H, d, H-6'), 1.85 (3H, s, H-22), 2.07 (3H, s, MeCOO-2'), 2.26 (6H, s, Me$_2$N), 2.89 (1H, m, H-14), 3.22&3.31 (each 3H, s, MeO-20), 3.48 (1H, m, H-5'), 3.69 (1H, dd, H-23a), 3.74 (1H, dd, H-23b), 4.32 (1H, d, $J_{1',2'}$=7.5 Hz, H-1'), 4.53 (1H, dd, H-20), 4.78 (1H, dd, $J_{2',3'}$=10.5 Hz, H-2'), 4.86 (1H, m, H-15), 5.78 (1H, d, $J_{13,14}$=10.5 Hz, H-13), 6.34 (1H, d, $J_{10,11}$=15.5 Hz, H-10), 7.25 (1H, d, H-11).

Example 1

Production of 23-Urethane Derivatives 300 mg of Compound (2) prepared in Reference Example 1 was dissolved in 6 mL of dichloromethane, to which 0.13 mL of triethylamine, and various isocyanic esters (1.5 molar to 2 molar equivalents for Compound (2)) were added and allowed to react at room temperature. The reaction completed in 1 hour to 72 hours. The reaction solution was concentrated, and the residue obtained was dissolved in 6 mL of methanol and left at rest overnight at room temperature to eliminate the acetyl group. Next, the reaction solution was concentrated and the residue obtained was dissolved in 6 mL of acetonitrile. Then, 6 mL of 1 M hydrochloric acid was added and left at rest for 1 hour to 2 hours at room temperature to remove the acetal group. The reaction solution was concentrated to a small amount and then neutralized by adding 5% aqueous sodium hydrogen carbonate solution. The resulting precipitate was extracted with chloroform, and the organic layer was washed with water, then dried with anhydrous sodium sulfate, and concentrated. The residue obtained was purified by silica gel column chromatography (developed with chloroform: methanol:28% aqueous ammonia=10:1:0.1) to give various 23-urethane derivatives as a colorless solid. Reaction formula is shown below.

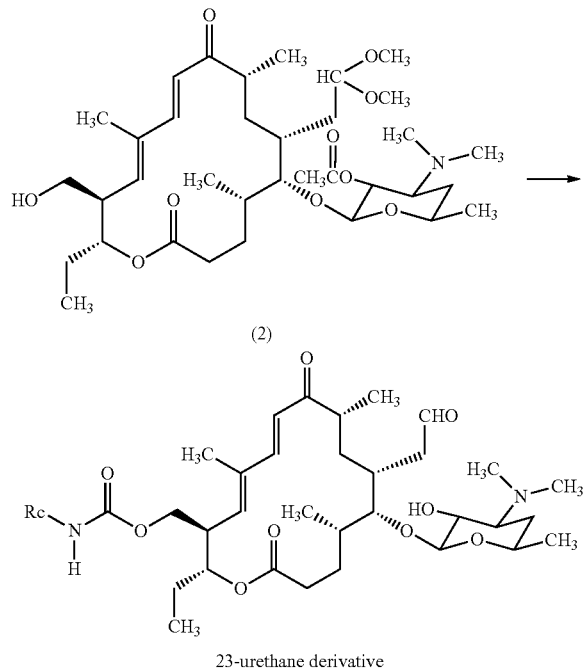

The yield and analytical values of the respective 23-urethane derivatives obtained are shown below.

MKT-1001: yield 228 mg (77%).
$^1$H-NMR (deuteriochloroform): δ 0.94 (3H, t, H-17), 1.05 (3H, d, H-18), 1.82 (3H, s, H-22), 2.26 (6H, s, Me$_2$N), 3.19 (1H, dd, J$_{2',3'}$=10 Hz, H-2'), 4.19 (1H, d, J$_{1',2'}$=7 Hz, H-1'), 4.90 (1H, m, H-15), 5.82 (1H, d, J$_{13,14}$=10.5 Hz, H-13), 6.35 (1H, d, J$_{10,11}$=15.5 Hz, H-10), 7.29 (1H, d, H-11), 9.70 (1H, s, H-20).

MKT-1002: yield 260 mg (81%).
$^1$H-NMR (deuteriochloroform): δ 0.94 (3H, t, H-17), 1.04 (3H, d, H-18), 1.81 (3H, s, H-22), 2.26 (6H, s, Me$_2$N), 3.18 (1H, dd, J$_{2',3'}$=10 Hz, H-2'), 4.12 (1H, dd, H-23a), 4.18 (1H, d, J$_{1',2'}$=7 Hz, H-1'), 4.23 (1H, dd, H-23b), 4.36 (2H, m, PhCH$_2$), 4.89 (1H, m, H-15), 5.08 (1H, br t, PhCH$_2$NH), 5.82 (1H, d, J$_{13,14}$=10.5 Hz, H-13), 6.34 (1H, d, J$_{10,11}$=15.5 Hz, H-10), 9.70 (1H, s, H-20).

MKT-1003: yield 271 mg (86%).
$^1$H-NMR (deuteriochloroform): δ 0.96 (3H, t, H-17), 1.05 (3H, d, H-18), 1.84 (3H, s, H-22), 2.26 (6H, s, Me$_2$N), 3.19 (1H, dd, H-2'), 4.19 (1H, d, H-1'), 4.95 (1H, m, H-15), 5.87 (1H, d, J$_{13,14}$=10.5 Hz, H-13), 6.36 (1H, d, J$_{10,11}$=15.5 Hz, H-10), 6.70 (1H, br s, NH), 9.70 (1H, s, H-20).

MKT-1004: yield 258 mg (79%).
$^1$H-NMR (deuteriochloroform): δ 0.94 (3H, t, H-17), 1.04 (3H, d, H-18), 1.81 (3H, s, H-22), 2.26 (6H, s, Me$_2$N), 4.19 (1H, d, H-1'), 4.75 (1H, br t, NH), 4.87 (1H, m, H-15), 5.80 (1H, d, J$_{13,14}$=10.5 Hz, H-13), 6.34 (1H, d, J$_{10,11}$=15.5 Hz, H-10), 9.70 (1H, s, H-20).

MKT-1005: yield 252 mg (72%).
$^1$H-NMR (deuteriochloroform): δ 0.97 (3H, t, H-17), 1.05 (3H, d, H-18), 1.85 (3H, s, H-22), 2.27 (6H, s, Me$_2$N), 3.19 (1H, dd, H-2'), 4.96 (1H, m, H-15), 5.89 (1H, d, J$_{13,14}$=10.5 Hz, H-13), 6.37 (1H, d, J$_{10,11}$=15.5 Hz, H-10), 6.79 (1H, br s, NH), 9.70 (1H, s, H-20).

MKT-1006: yield 258 mg (79%).
$^1$H-NMR (deuteriochloroform): δ 0.91 (3H, t, H-17), 1.05 (3H, d, H-18), 1.82 (3H, s, H-22), 2.26 (6H, s, Me$_2$N), 3.19 (1H, dd, J$_{2',3'}$=10 Hz, H-2'), 4.05 (1H, dd, H-23a), 4.19 (1H, d, J$_{1,2}$=7 Hz, H-1'), 4.89 (1H, m, H-15), 5.03 (1H, broad, NH), 5.84 (1H, br d, J$_{13,14}$=10 Hz, H-13), 6.34 (1H, d, J$_{10,11}$=15.5 Hz, H-10), 9.70 (1H, s, H-20).

MKT-1007: yield 301 mg (86%).
$^1$H-NMR (deuteriochloroform): δ 0.97 (3H, t, H-17), 1.05 (3H, d, H-18), 1.84 (3H, s, H-22), 2.26 (6H, s, Me$_2$N), 4.19 (1H, d, H-1'), 4.95 (1H, m, H-15), 5.87 (1H, J$_{13,14}$=10.5 Hz, H-13), 6.36 (1H, d, J$_{10,11}$=15.5 Hz, H-10), 6.71 (1H, br s, NH), 9.70 (1H, s, H-20).

MKT-1008: yield 280 mg (78%).
$^1$H-NMR (deuteriochloroform). δ 0.96 (3H, t, H-17), 1.05 (3H, d, H-18), 1.83 (3H, s, H-22), 2.26 (6H, s, Me$_2$N), 4.19 (1H, d, H-1'), 4.93 (1H, m, H-15), 5.04 (2H, s, PhCH$_2$), 5.86 (1H, d, J$_{13,14}$=10.5 Hz, H-13), 6.36 (1H, d, J$_{10,11}$=15.5 Hz, H-10), 6.59 (1H, br s, NH), 9.70 (1H, s, H-20).

MKT-1009: yield 252 mg (77%).
$^1$H-NMR (deuteriochloroform): δ 1.04 (3H, d, H-18), 1.77 (3H, s, H-22), 2.26 (6H, s, Me$_2$N), 3.19 (1H, dd, J$_{2',3'}$=10 Hz, H-2'), 4.07 (1H, broad, H-23a), 4.16 (1H, dd, H-23b), 4.19 (1H, d, J$_{1',2'}$=7 Hz, H-1'), 4.89 (1H, br t, H-15), 5.03 (1H, broad, NH), 5.80 (1H, br d, J$_{13,14}$=9.5 Hz, H-13), 6.33 (1H, d, J$_{10,11}$=15.5 Hz, H-10), 9.70 (1H, s, H-20).

MKT-1010: yield 238 mg (77%).
$^1$H-NMR (deuteriochloroform): δ 0.94 (3H, t, H-17), 1.05 (3H, d, H-18), 1.82 (3H, s, H-22), 2.26 (6H, s, Me$_2$N), 4.19 (1H, d, H-1'), 4.90 (1H, m, H-15), 5.83 (1H, d, J$_{13,14}$=10.5 Hz, H-13), 6.35 (1H, d, J$_{10,11}$=15.5 Hz, H-10), 7.30 (1H, d, H-11), 9.70 (1H, s, H-20).

MKT1011: yield 261 mg (78%).
$^1$H-NMR (deuteriochloroform): δ 0.94 (3H, t, H-17), 1.04 (3H, d, H-18), 1.81 (3H, s, H-22), 2.26 (6H, s, Me$_2$N), 3.18 (1H, dd, J$_{2',3'}$=10 Hz, H-2'), 3.79 (3H, s, MeO—C$_6$H$_4$), 4.11 (1H, dd, H-23a), 4.18 (1H, dd, J$_{2',3'}$=7 Hz, H-1'), 4.22 (1H, dd, H-23b), 4.29 (2H, m, MeO—C$_6$H$_4$—CH$_2$), 4.89 (1H, m, H-15), 4.98 (1H, t, NH—COO), 5.81 (1H, d, J$_{13,14}$=10.5 Hz, H-13), 6.34 (1H, d, J$_{10,11}$=15.5 Hz, H-10), 6.86&7.20 (each 2H, d, aromatic), 7.29 (1H, d, H-11), 9.70 (1H, s, H-20).

MKT-1012: yield 274 mg (82%).
$^1$H-NMR (deuteriochloroform): δ 0.95 (3H, t, H-17), 1.05 (3H, d, H-18), 1.83 (3H, s, H-22), 2.26 (6H, s, Me$_2$N), 2.91 (6H, s, Me$_2$N—C$_6$H$_4$), 4.19 (1H, d, H-1'), 4.93 (1H, m, H-15), 5.88 (1H, br d, H-13), 6.35 (1H, d, J$_{10,11}$=15.5 Hz, H-10), 7.31 (1H, d, H-11), 9.70 (1H, s, H-20).

MKT-1013: yield 231 mg (71%).
$^1$H-NMR (deuteriochloroform): δ 0.94 (3H, t, H-17), 1.05 (3H, d, H-18), 1.82 (3H, s, H-22), 2.26 (6H, s, Me$_2$N), 4.19 (1H, d, H-1'), 4.70 (1H, br t, NH), 4.90 (1H, m, H-15), 5.83 (1H, d, J$_{13,14}$=10.5 Hz, H-13), 6.35 (1H, d, J$_{10,11}$=15.5 Hz, H-10), 7.30 (1H, d, H-11), 9.70 (1H, s, H-20).

MKT-1014: yield 231 mg (72%).
$^1$H-NMR (deuteriochloroform): δ 0.96 (3H, t, H-17), 1.05 (3H, d, H-18), 1.84 (3H, s, H-22), 2.26 (6H, s, Me$_2$N), 2.29 (6H, s, Mex2), 4.19 (1H, d, H-1'), 4.93 (1H, m, H-15), 5.86 (1H, d, J$_{13,14}$=10.5 Hz, H-13), 6.36 (1H, d, J$_{10,11}$=15.5 Hz, H-10), 6.56 (1H, br s, NH), 7.31 (1H, d, H-11), 9.70 (1H, s, H-20).

MKT-1015: yield 237 mg (71%).
$^1$H-NMR (deuteriochloroform): δ 1.05 (3H, d, H-18), 1.84 (3H, s, H-22), 2.26 (6H, s, Me$_2$N), 4.19 (1H, d, H-1'), 4.94

(1H, m, H-15), 5.86 (1H, d, $J_{13,14}$=10.5 Hz, H-13), 6.36 (1H, d, $J_{10,11}$=15.5 Hz, H-10), 6.60 (1H, br s, NH), 9.70 (1H, s, H-20).

MKT-1016: yield 250 mg (73%).

$^1$H-NMR (deuteriochloroform): δ 1.05 (3H, d, H-18), 1.83 (3H, s, H-22), 2.26 (6H, s, Me$_2$N), 3.93 (2H, t), 4.19 (1H, d, H-1'), 4.94 (1H, m, H-15), 5.86 (1H, d, $J_{13,14}$=10.5 Hz, H-13), 6.36 (1H, d, $J_{10,11}$=15.5 Hz, H-10), 6.54 (1H, br s, NH), 9.70 (1H, s, H-20).

MKT-1017: yield 272 mg (83%).

$^1$H-NMR (deuteriochloroform): δ 0.96 (3H, t, H-17), 1.05 (3H, d, H-18), 1.84 (3H, s, H-22), 2.26 (6H, s, Me$_2$N), 2.46 (3H, s, MeS), 4.19 (1H, d, H-1'), 4.94 (1H, m, H-15), 5.86 (1H, d, $J_{13,14}$=10.5 Hz, H-13), 6.36 (1H, d, $J_{10,11}$=15.5 Hz, H-10), 6.65 (1H, br s, NH), 9.70 (1H, s, H-20).

Example 2-1

Production of 23-Ester Derivatives [11]

400 mg of Compound (2) prepared in Reference Example 1 was dissolved in 8 mL of pyridine. To this solution, acetic anhydride (5 molar equivalents for Compound (2)) or benzoyl chloride (1.5 molar equivalents for Compound (2)) was added under cooling with ice and allowed to react for 2 hours at the same temperature. Excess reagent was destroyed by the addition of a small amount of water to the reaction solution. Then, the reaction solution was concentrated and the syrup obtained was extracted with chloroform. The organic layer was washed with aqueous sodium hydrogen carbonate solution and water, successively, dried with anhydrous sodium sulfate, and concentrated. The thus obtained protected 23-ester derivative was dissolved in 8 mL of methanol, heated at 50° C. for 5 hours to selectively eliminate the acetyl group of the hydroxy group at 2' position of sugar. Next, this reaction solution was concentrated, and the residue obtained was dissolved in 8 mL of acetonitrile. To this solution, 2 mL of 0.3 M hydrochloric acid was added and left at rest for 2 hours at room temperature to remove the acetal group. The reaction solution was neutralized by the addition of aqueous sodium hydrogen carbonate solution and then extracted with chloroform. The organic layer was washed with water, dried with anhydrous sodium sulfate, and concentrated. The residue obtained was purified by silica gel column chromatography (developed with chloroform:methanol=10:1) to give 23-ester derivatives as a colorless solid. Reaction formula is shown below.

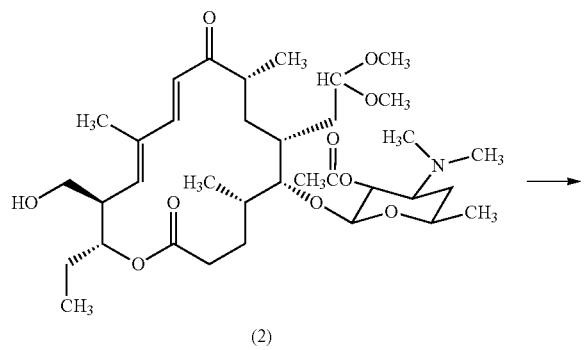

(2)

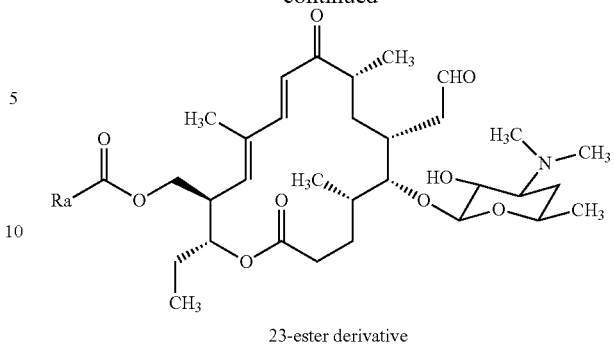

23-ester derivative

The yield and analytical values of the respective 23-ester derivatives obtained are shown below.

MKT-2002: yield 334 mg (90%).

$^1$H-NMR (deuteriochloroform): δ 0.95 (3H, t, H-17), 1.05 (3H, d, H-18), 1.83 (3H, s, H-22), 2.06 (3H, s, MeCO), 2.26 (6H, s, Me$_2$N), 4.19 (1H, d, H-1'), 4.89 (1H, m, H-15), 5.79 (1H, d, $J_{13,14}$=10.5 Hz, H-13), 6.36 (1H, d, $J_{10,11}$=15.5 Hz, H-10), 7.29 (1H, d, H-11), 9.70 (1H, s, H-20).

MKT-2003: yield 354 mg (88%).

$^1$H-NMR (deuteriochloroform): δ 0.97 (3H, t, H-17), 1.05 (3H, d, H-18), 1.86 (3H, s, H-22), 2.27 (6H, s, Me$_2$N), 4.19 (1H, d, H-1'), 5.02 (1H, m, H-15), 5.92 (1H, d, $J_{13,14}$=10.5 Hz, H-13), 6.37 (1H, d, $J_{10,11}$=15.5 Hz, H-10), 9.70 (1H, s, H-20).

Example 2-2

Production of 23-Ester Derivatives [21]

400 mg of Compound (2) prepared in Reference Example 1 was dissolved in 8 mL of acetonitrile, to which various carboxylic acids (2 molar equivalents for Compound (2)), 75 mg of 4-dimethylaminopyridine, and 164 mg of 1,3-dicyclohexylcarbodiimide were added and allowed to react for 1 hour to 4 hours at room temperature. The reaction solution was concentrated, and the residue obtained was dissolved in 8 mL of methanol and left at rest overnight at room temperature to eliminate the acetyl group. Next, this reaction solution was concentrated, and the residue obtained was dissolved in 8 mL of acetonitrile. To this solution, 8 mL of 0.3 M hydrochloric acid was added and left at rest for 1 hour to 2 hours at room temperature to remove the acetal group. The reaction solution was concentrated to a small amount and neutralized by adding 5% aqueous sodium hydrogen carbonate solution. The resulting precipitate was extracted with chloroform, and the organic layer was washed with water, dried with anhydrous sodium sulfate, and concentrated. The residue obtained was purified by silica gel column chromatography (developed with chloroform:methanol=10:1) to give various 23-ester derivatives as a colorless solid.

The yield and analytical values of the respective 23-ester derivatives obtained are shown below.

MKT-2004: yield 398 mg (90%).

$^1$H-NMR (deuteriochloroform): δ 1.05 (3H, d, H-18), 1.85 (3H, s, H-22), 2.28 (6H, s, Me$_2$N), 4.20 (1H, d, H-1'), 5.02 (1H, m, H-15), 5.92 (1H, d, $J_{13,14}$=10.5 Hz, H-13), 6.36 (1H, d, $J_{2',3'}$=15.5 Hz, H-10), 9.70 (1H, s, H-20).

MKT-2005: yield 347 mg (83%).

$^1$H-NMR (deuteriochloroform): δ 0.89 (3H, t, H-17), 1.04 (3H, d, H-18), 1.75 (3H, s, H-22), 2.26 (6H, s, Me$_2$N), 3.19 (1H, dd, $J_{2',3'}$=10 Hz, H-2'), 3.61 (2H, s, PhCH$_2$CO), 4.10 (1H, dd, H-23a), 4.19 (1H, d, $J_{1',2'}$=7 Hz, H-1'), 4.20 (1H, dd, H-23b), 4.85 (1H, m, H-15); 5.70 (1H, d, $J_{13,14}$=10.5 Hz, H-13), 6.33 (1H, d, $J_{10,11}$=15.5 Hz, H-10), 9.71 (1H, s, H-20).

MKT-2006: yield 378 mg (85%).

$^1$H-NMR (deuteriochloroform): δ 0.90 (3H, t, H-17), 1.04 (3H, d, H-18), 1.73 (3H, s, H-22), 2.26 (6H, s, Me$_2$N), 2.91 (6H, s, Me$_2$N—C$_6$H$_4$), 3.18 (1H, dd, $J_{2',3'}$=10 Hz, H-2'), 3.50 (2H, s, Me$_2$N—C$_6$H$_4$—CH$_2$), 4.06 (1H, dd, H-23a), 4.18 (1H, dd, H-23b), 4.19 (1H, d, $J_{1',2'}$=7 Hz, H-1'), 4.85 (1H, m, H-15), 5.71 (1H, d, $J_{13,14}$=10.5 Hz, H-13), 6.32 (1H, d, $J_{10,11}$=15.5 Hz, H-10), 6.67&7.11 (each 2H, d, aromatic), 7.25 (1H, d, H-11), 9.70 (1H, s, H-20).

MKT-2007: yield 355 mg (81%).

$^1$H-NMR (deuteriochloroform): δ 0.90 (3H, t, H-17), 1.04 (3H, d, H-18), 1.74 (3H, s, H-22), 2.26 (6H, s, Me$_2$N), 3.19 (1H, dd, $J_{2',3'}$=10 Hz, H-2'), 3.54 (2H, s, MeO—C$_6$H$_4$—CH$_2$), 3.77 (3H, s, MeO—C$_6$H$_4$—CH$_2$), 4.09 (1H, dd, H-23a), 4.18 (1H, d, $J_{1',2'}$=7 Hz, H-1'), 4.19 (1H, dd, H-23b), 4.84 (1H, m, H-15), 5.71 (1H, d, $J_{13,14}$=10.5 Hz, H-13), 6.33 (1H, d, $J_{10,11}$=15.5 Hz, H-10), 6.84&7.17 (each 2H, d, aromatic), 7.24 (1H, d, H-11), 9.70 (1H, s, H-20).

MKT-2008: yield 383 mg (91%).

$^1$H-NMR (deuteriochloroform). δ 0.91 (3H, t, H-17), 1.04 (3H, d, H-18), 1.77 (3H, s, H-22), 2.26 (6H, s, Me$_2$N), 3.19 (1H, dd, $J_{2',3'}$=10 Hz, H-2'), 3.66 (2H, s, CH$_2$COO), 4.12 (1H, dd, H-23a), 4.19 (1H, d, $J_{1',2'}$=7.5 Hz, H-1'), 4.21 (1H, dd, H-23b), 4.86 (1H, m, H-15), 5.73 (1H, d, $J_{13,14}$=10.5 Hz, H-13), 6.34 (1H, d, $J_{10,11}$=15.5 Hz, H-10), 9.71 (1H, s, H-20).

MKT-2009: yield 385 mg (80%).

$^1$H-NMR (deuteriochloroform): δ 0.94 (3H, t, H-17), 1.04 (3H, d, H-18), 1.82 (3H, s, H-22), 2.26 (6H, s, Me$_2$N), 2.94 (2H, t, CH$_2$), 3.18 (1H, dd, $J_{2',3'}$=10 Hz, H-2'), 3.59 (2H, t, CH$_2$), 4.15 (1H, dd, H-23a), 4.18 (1H, d, $J_{1',2'}$=7 Hz, H-1'), 4.24 (1H, dd, H-23b), 4.87 (1H, m, H-15), 5.76 (1H, d, $J_{13,14}$=10.5 Hz, H-13), 6.34 (1H, d, $J_{10,11}$=15.5 Hz, H-10), 9.69 (1H, s, H-20).

MKT-2010: yield 386 mg (90%).

$^1$H-NMR (deuteriochloroform). δ 0.89 (3H, t, H-17), 1.04 (3H, d, H-18), 1.74 (3H, s, H-22), 2.26 (6H, s, Me$_2$N), 3.19 (1H, dd, $J_{2',3'}$=10 Hz, H-2'), 3.58 (2H, s, F—C$_6$H$_4$—CH$_2$), 4.11 (1H, dd, H-23a), 4.19 (1H, d, $J_{1',2'}$=7.5 Hz, H-1'), 4.20 (1H, dd, H-23b), 4.84 (1H, m, H-15), 5.71 (1H, d, $J_{13,14}$=10.5 Hz, H-13), 6.34 (1H, d, $J_{10,11}$=15.5 Hz, H-10), 9.71 (1H, s, H-20).

Example 2-3

Production of 23-Ester Derivatives [3]

300 mg of Compound (2) prepared in Reference Example 1 was dissolved in 6 mL of acetonitrile, to which various carboxylic acids (1.1 molar to 2 molar equivalents for Compound (2)), 30 mg of 4-dimethylaminopyridine, and 1-ethyl-3-(3-dimethylaminopropyl)carbodiimide hydrochloride (1.5 molar to 2 molar equivalents for Compound (2)) were added and allowed to react for 1 hour to 5 hours at room temperature. Addition of a small amount of water to the reaction solution followed by concentration gave a residue, which was extracted with chloroform. The organic layer was washed with aqueous potassium hydrogen sulfate solution, aqueous sodium hydrogen carbonate solution, and water, successively, dried with anhydrous sodium sulfate, and concentrated. The thus obtained solid was dissolved in 6 mL of a mixed solution of methanol and acetic acid (50:1), heated at 50° C. for 1 hour to 5 hours to eliminate the acetyl group. Next, this reaction solution was concentrated, and the residue obtained was purified by silica gel column chromatography (developed with chloroform:methanol=10:1) to give protected form of 23-esters with a dimethylacetal. The solid obtained was dissolved in 2 mL to 3 mL of a mixed solution of 98% aquous acetonitrile and trifluoroacetic acid (4:1), and left at rest for 1 hour to 2 hours at room temperature to remove the acetal group. The reaction solution was concentrated to a small amount, to which diethyl ether was added. The resulting precipitate was further washed with diethyl ether and dried to give trifluoroacetic acid salt of various 23-ester derivatives in the form of a colorless solid.

The yield and analytical values of trifluoroacetic acid salt of the respective 23-ester derivatives obtained are shown below.

MKT-2101: yield 275 mg (the yield as its monotrifluoroacetic acid salt was 71% based on Compound (2)).

$^1$H-NMR (deuteriochloroform): δ 0.90 (3H, t, H-17), 0.99 (3H, d, H-18), 1.71 (3H, s, H-22), 3.73 (2H, s, NO$_2$—C$_6$H$_4$—CH$_2$), 4.28 (1H, d, H-1'), 4.82 (1H; m, H-15), 5.66 (1H, d, $J_{13,14}$=11 Hz, H-13), 6.31 (1H, d, $J_{10,11}$=15.5 Hz, H-10), 7.17 (1H, d, H-11), 9.68 (1H, s, H-20).

MKT-2102: yield 305 mg (the yield as its monotrifluoroacetic acid salt was 80% based on Compound (2)).

$^1$H-NMR (deuteriochloroform): δ 0.92 (3H, t, H-17), 1.00 (3H, d, H-18), 1.81 (3H, s, H-22), 3.94 (2H, ABq, S—CH$_2$—CO), 4.28 (1H, d, H-1'), 4.88 (1H, m, H-15), 5.66 (1H, d, $J_{13,14}$=10.5 Hz, H-13), 6.34 (1H, d, $J_{10,11}$=15.5 Hz, H-10), 7.03 (1H, t, aromatic), 7.14 (1H, d, H-11), 8.54 (2H, d, aromatic), 9.69 (1H, s, H-20).

MKT-2103: yield 283 mg (the yield as its monotrifluoroacetic acid salt was 76% based on Compound (2)).

$^1$H-NMR (deuteriochloroform): δ 0.93 (3H, t, H-17), 0.99 (3H, d, H-18), 1.81 (3H, s, H-22), 4.28 (1H, d, H-1'), 4.86 (1H, m, H-15), 5.72 (1H, d, $J_{13,14}$=10.5 Hz, H-13), 6.34 (1H, d, $J_{10,11}$=15.5 Hz, H-10), 9.67 (1H, s, H-20).

MKT-2104: yield 265 mg (the yield as its monotrifluoroacetic acid salt was 70% based on Compound (2)).

$^1$H-NMR (deuteriochloroform): δ 0.95 (3H, t, H-17), 1.00 (3H, d, H-18), 1.83 (3H, s, H-22), 4.28 (1H, d, H-1'), 4.88 (1H, m, H-15), 5.79 (1H, d, $J_{13,14}$=10.5 Hz, H-13), 6.35 (1H, d, $J_{10,11}$=15.5 Hz, H-10), 9.67 (1H, s, H-20).

MKT-2105: yield 324 mg (the yield as its monotrifluoroacetic acid salt was 83% based on Compound (2)).

$^1$H-NMR (deuteriochloroform): δ 0.92 (3H, t, H-17), 1.00 (3H, d, H-18), 1.80 (3H, s, H-22), 4.65 (2H, s, O—CH$_2$—CO), 4.87 (1H, m, H-15), 5.68 (1H, d, $J_{13,14}$=10.5 Hz, H-13), 6.35 (1H, d, $J_{10,11}$=15.5 Hz, H-10), 6.89 (2H, d) & 6.99 (1H, t) (aromatic), 9.68 (1H, s, H-20).

MKT-2106: yield 308 mg (the yield as its monotrifluoroacetic acid salt was 84% based on Compound (2)).

$^1$H-NMR (deuteriochloroform): δ 0.92 (3H, t, H-17), 1.00 (3H, d, H-18), 1.85 (3H, s, H-22), 4.95 (1H, m, H-15), 5.85 (1H, d, $J_{13,14}$=10.5 Hz, H-13), 6.30&7:42 (each 1H, d, CO—CH=CH—), 6.36 (1H, d, $J_{10,11}$=15.5 Hz, H-10), 7.31 (1H, d, H-11), 9.67 (1H, s, H-20).

MKT-2107: yield 314 mg (the yield as its ditrifluoroacetic acid salt was 75% based on Compound (2)).

$^1$H-NMR (deuteriochloroform): δ 1.79 (3H, s, H-22), 4.78 (1H, m, H-15), 5.54 (1H, d, $J_{13,14}$=10 Hz, H-13), 6.33 (1H, d, $J_{10,11}$=15 Hz, H-10), 7.13 (1H, d, H-11), 7.62 (2H, d, aromatic), 8.11 (1H, t) & 8.78 (1H, d) (aromatic), 9.69 (1H, s, H-20).

MKT-2108: yield 306 mg (the yield as its ditrifluoroacetic acid salt was 73% based on Compound (2)).

$^1$H-NMR (deuteriochloroform): δ 0.93 (3H, d, H-17), 0.99 (3H, d, H-18), 1.79 (3H, s, H-22), 4.80 (1H, m, H-15), 5.60 (1H, d, $J_{13,14}$=10.5 Hz, H-13), 6.35 (1H, d, $J_{10,11}$=15.5 Hz, H-10), 7.12 (1H, d, H-11), 7.77 (1H, dd, aromatic), 8.21 (1H, d, aromatic), 8.73 (1H, d, aromatic), 8.78 (1H, d, aromatic), 9.69 (1H, s, H-20).

MKT-2109: yield 279 mg (the yield as its monotrifluoroacetic acid salt was 72% based on Compound (2)).

$^1$H-NMR (deuteriochloroform): δ 0.90 (3H, t, H-17), 1.00 (3H, d, H-18), 1.72 (3H, s, H-22), 2.45 (3H, s, SMe), 3.56 (2H, s, COCH$_2$), 4.28 (1H, d, H-1'), 4.83 (1H, m, H-15), 5.69 (1H, d, $J_{13,14}$=10.5 Hz, H-13), 6.33 (1H, d, $J_{10,11}$=15.5 Hz, H-10), 9.68 (1H, s, H-20).

MKT-2110: yield 273 mg (the yield as its monotrifluoroacetic acid salt was 77% based on Compound (2)).

$^1$H-NMR (deuteriochloroform). δ1.84 (3H, s, H-22), 4.28 (1H, d, H-1'), 4.93 (1H, m, H-15), 5.76 (1H, d), 5.83 (1H, $J_{13,14}$=10.5 Hz, H-13), 6.35 (1H, d, $J_{10,11}$=15.5 Hz, H-10), 7.30 (1H, d, H-11), 9.67 (1H, s, H-20).

MKT-2111: yield 277 mg (the yield as its monotrifluoroacetic acid salt was 73% based on Compound (2)).

$^1$H-NMR (deuteriochloroform). δ1.81 (3H, s, H-22), 4.28 (1H, d, H-1'), 6.35 (1H, d, $J_{10,11}$=15.5 Hz, H-10), 9.68 (1H, s, H-20).

MKT-2112: yield 303 mg (the yield as its monotrifluoroacetic acid salt was 78% based on Compound (2)).

$^1$H-NMR (deuteriochloroform): δ 1.82 (3H, s, H-22), 4.28 (1H, d, H-1'), 6.35 (1H, d, $J_{10,11}$=15.5 Hz, H-10), 9.68 (1H, s, H-20).

MKT-2113: yield 252 mg (the yield as its monotrifluoroacetic acid salt was 81% based on Compound (2)).

$^1$H-NMR (deuteriochloroform): δ1.81 (3H, s, H-22), 4.28 (1H, d, H-1'), 6.35 (1H, d, $J_{10,11}$=15.5 Hz, H-10), 9.67 (1H, s, H-20).

Reference Example 2

Production of 3,23,4'-Trideoxy-23-iodomycaminosyltylonolide Dimethylacetal 15.5 g of a compound described in Carbohydrate Research 274 (1995) 269-278 (Compound (1) in the following reaction formula) was dissolved in 225 mL of pyridine, to which 9.28 g of triphenylphosphine and 6.50 g of iodine were added and allowed to react under nitrogen atmosphere at room temperature for 2 hours. The reaction solution was concentrated and the syrup obtained was extracted with chloroform. The organic layer was washed with 10% aqueous sodium thiosulfate solution, 5% aqueous sodium hydrogen carbonate solution, and water, successively, dried with anhydrous sodium sulfate, and concentrated. The residue obtained was purified by silica gel column chromatography (developed with chloroform:methanol:28% aqueous ammonia=10:1:0.1) to give 16.1 g of 3,23,4'-trideoxy-23-iodomycaminosyltylonolide dimethylacetal (Compound (3) in the following reaction formula) as a pale yellow solid. The yield was 88%. Reaction formula is shown below.

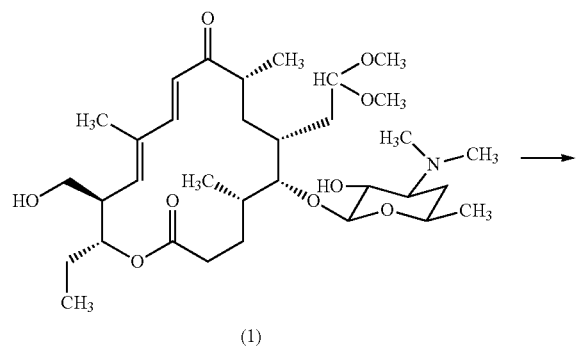

(1)

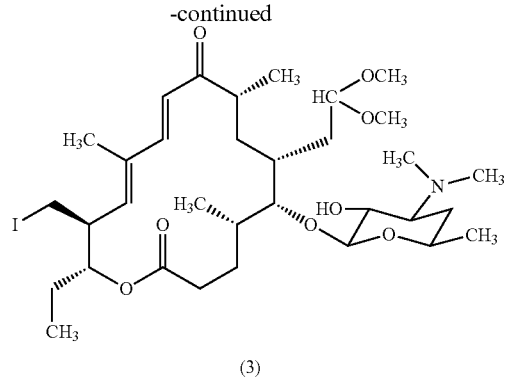

(3)

The analytical values of Compound (3) obtained is shown below.

$^1$H-NMR (deuteriochloroform): δ 0.94 (3H, t, H-17), 1.06 (3H, d, H-18), 1.20 (3H, d, H-21), 1.25 (3H, d, H-6'), 1.82 (3H, s, H-22), 2.27 (6H, s, Me$_2$N), 3.06 (1H, t, H-23a), 3.22 & 3.31 (each 3H, s, MeO-20), 4.26 (1H; d, $J_{1',2'}$=7 Hz, H-1'), 4.56 (1H, dd, H-20), 4.77 (1H, m, H-15), 5.65 (1H, d, $J_{13,14}$=10.5 Hz, H-13), 6.37 (1H, d, $J_{10,11}$=15.5 Hz, H-10), 7.29 (1H, d, H-11).

Example 3

Production of 23-Amine Derivatives 300 mg of Compound (3) prepared in Reference Example 2 was dissolved in 6 mL of acetonitrile, to the resulting solution, various secondary amines or THF solutions of secondary amines (4 molar to 10 molar equivalents for Compound (3)) were added and heated for 1 hour to 100 hours at 80° C. The reaction solution was concentrated and the syrup obtained was extracted with chloroform. The organic layer was washed with 5% aqueous potassium hydrogen sulfate solution, 5% aqueous sodium hydrogen carbonate solution, and water, successively, dried with anhydrous sodium sulfate, and concentrated. Next, the syrup obtained was dissolved in 5 mL of acetonitrile, to which 3 mL to 8 mL of 0.3 M hydrochloric acid was added and left at rest for 1 hour to 2 hours at room temperature to remove the acetal group. The reaction solution was concentrated to a small amount, which was neutralized by adding 5% aqueous sodium hydrogen carbonate solution. The resulting precipitate was extracted with chloroform.

The organic layer was washed with water, dried with anhydrous sodium sulfate, and concentrated. The residue obtained was purified by silica gel column chromatography (developed with chloroform:methanol:28% aqueous ammonia=10:1: 0.1) to give various 23-amine derivatives as a colorless solid as shown below. Reaction formula is shown below.

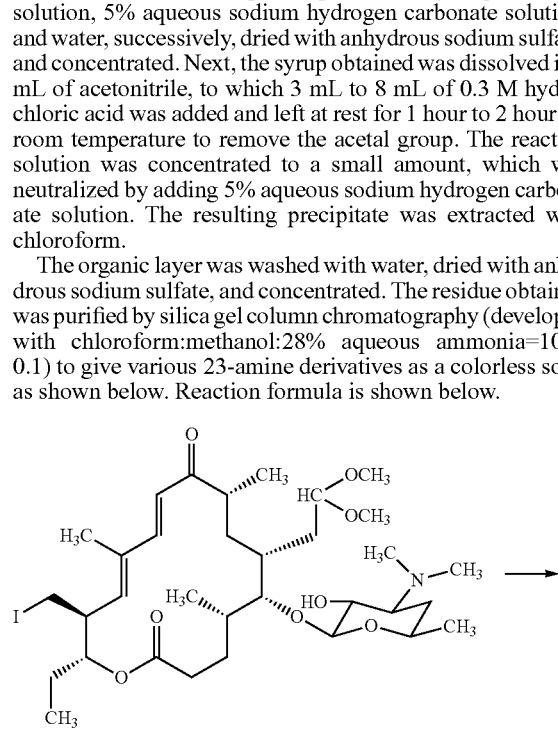

(3)

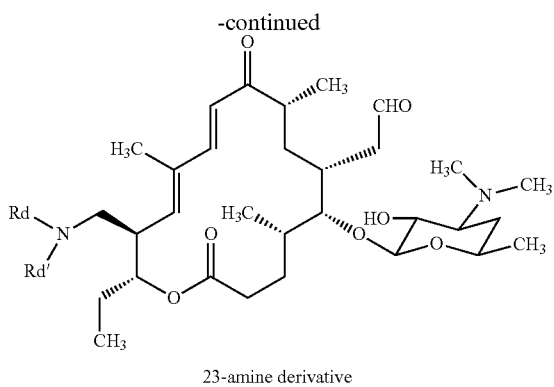

23-amine derivative

The yield and analytical values of the respective 23-amine derivatives obtained are shown below.

MKT-3002: yield 181 mg (65%).
$^1$H-NMR (deuteriochloroform): δ 0.90 (3H, t, H-17), 1.04 (3H, d, H-18), 1.83 (3H, s, H-22), 2.16 (3H, s, MeN-23), 2.26 (6H, s, Me$_2$N), 3.19 (1H, dd, J$_{2',3'}$=10 Hz, H-2'), 3.32&3.57 (each 1H, d, PhCH$_2$), 4.19 (1H, d, J$_{1',2'}$=7 Hz, H-1'), 4.66 (1H, m, H-15), 5.73 (1H, d, J$_{13,14}$=10.5 Hz, H-13), 6.32 (1H, d, J$_{10,11}$=15.5 Hz, H-10), 7.35 (1H, d, H-11), 9.70 (1H, s, H-20).

MKT-3101: yield 205 mg (83%).
$^1$H-NMR (deuteriochloroform): δ 0.93 (3H, t, H-17), 1.05 (3H, d, H-18), 1.84 (3H, s, H-22), 2.18 (6H, s, Me$_2$N-23), 2.26 (6H, s, Me$_2$N-3'), 3.18 (1H, dd, J$_{2',3'}$=10 Hz, H-2'), 4.19 (1H, d, J$_{1',2'}$=7.5 Hz, H-1'), 4.70 (1H, m, H-15), 5.74 (1H, d, J$_{13,14}$=10.5 Hz, H-13), 6.29 (1H, d, J$_{10,11}$=15.5 Hz, H-10), 7.34 (1H, d, H-11), 9.70 (1H, s, H-20).

MKT-3102: yield 131 mg (48%).
$^1$H-NMR (deuteriochloroform): δ 0.97 (3H, t, H-17), 1.03 (3H, d, H-18), 1.62 (3H, s, H-22), 2.26 (6H, s, Me$_2$N), 2.87 (3H, s, MeN-23), 3.25 (1H, dd, H-23a), 3.67 (1H, dd, H-23b), 4.18 (1H, d, J$_{1',2'}$=7.5 Hz, H-1'), 4.81 (1H, m, H-15), 5.77 (1H, d, J$_{13,14}$=10.5 Hz, H-13), 6.27 (1H, d, J$_{10,11}$=15.5 Hz, H-10), 9.70 (1H, s, H-20).

MKT-6101: yield 195 mg (74%).
$^1$H-NMR (deuteriochloroform): δ 0.92 (3H, t, H-17), 1.04 (3H, d, H-18), 1.82 (3H, s, H-22), 2.26 (6H, s, Me$_2$N), 4.19 (1H, d, H-1'), 4.69 (1H, m, H-15), 5.75 (1H, d, J$_{13,14}$=10.5 Hz, H-13), 6.31 (1H, d, J$_{10,11}$=15.5 Hz, H-10), 7.32 (1H, d, H-11), 9.70 (1H, s, H-20).

MKT-6102: yield 188 mg (70%).
$^1$H-NMR (deuteriochloroform): δ 0.91 (3H, t, H-17), 1.04 (3H, d, H-18), 1.82 (3H, s, H-22), 2.26 (6H, s, Me$_2$N), 4.19 (1H, d, H-1'), 4.68 (1H, m, H-15), 6.30 (1H, d, J$_{10,11}$=15.5 Hz, H-10), 7.33 (1H, d, H-11), 9.70 (1H, s, H-20).

MKT-6103: yield 211 mg (70%).
$^1$H-NMR (deuteriochloroform): δ 0.91 (3H, t, H-17), 1.04 (3H, d, H-18), 1.80 (3H, s, H-22), 2.26 (6H, s, Me$_2$N), 4.19 (1H, d, H-1'), 4.69 (1H, m, H-15), 5.75 (1H, d, J$_{13,14}$=10 Hz, H-13), 6.30 (1H, d, J$_{10,11}$=15.5 Hz, H-10), 7.11 (2H, d, aromatic), 7.32 (1H, d, H-11), 9.70 (1H, s, H-20).

MKT-6104: yield 210 mg (68%).
$^1$H-NMR (deuteriochloroform): δ 0.92 (3H, t, H-17), 1.05 (3H, d, H-18), 1.81 (3H, s, H-22), 2.24 (3H, s, CH$_2$NMe), 2.27 (6H, s, Me$_2$N), 3.85&3.86 (each 3H, s, OMe), 4.19 (1H, d, H-1'), 4.71 (1H, m, H-15), 5.76 (1H, d, J$_{13,14}$=10 Hz, H-13), 6.30 (1H, d, J$_{10,11}$=15.5 Hz, H-10), 7.33 (1H, d, H-11), 9.70 (1H, s, H-20).

MKT-6105: yield 131 mg (51%).
$^1$H-NMR (deuteriochloroform): δ 0.94 (3H, t, H-17), 1.05 (3H, d, H-18), 1.84 (3H, s, H-22), 2.26 (6H, s, Me$_2$N), 2.32 (3H, s, CH$_2$NMe), 3.47 (2H, ABq, CH$_2$NMe), 4.19 (1H, d, H-1'), 4.73 (1H, m, H-15), 5.70 (1H, d, J$_{13,14}$=10 Hz, H-13), 6.32 (1H, d, J$_{10,11}$=15.5 Hz, H-10), 7.30 (1H, d, H-11), 9.70 (1H, s, H-20).

MKT-6106: yield 200 mg (72%).
$^1$H-NMR (deuteriochloroform): δ 0.93 (3H, t, H-17), 1.04 (3H, d, H-18), 1.83 (3H, s, H-22), 2.25 (3H, s, CH$_2$NMe), 2.26 (6H, s, Me$_2$N), 3.32&3.35 (each 3H, s, OMe), 4.19 (1H, d, H-1'), 4.39 (1H, t, CH(OMe)$_2$), 4.69 (1H, m, H-15), 5.74 (1H, d, J$_{13,14}$=10 Hz, H-13), 6.30 (1H, d, J$_{10,11}$=15.5 Hz, H-10), 7.32 (1H, d, H-11), 9.70 (1H, s, H-20).

MKT-6107: yield 157 mg (58%).
$^1$H-NMR (deuteriochloroform): δ 0.93 (3H, t, H-17), 1.04 (3H, d, H-18), 1.83 (3H, s, H-22), 2.19 (3H, s, CH$_2$N(Me)CH$_2$), 2.22 (6H, s, CH$_2$NMe$_2$), 2.26 (6H, s, Me$_2$N-3'), 4.19 (1H, d, H-1'), 4.69 (1H, m, H-15), 5.74 (1H, d, J$_{13,14}$=10.5 Hz, H-13), 6.30 (1H, d, J$_{10,11}$=15.5 Hz, H-10), 7.32 (1H, d, H-11), 9.70 (1H, s, H-20).

MKT-6108: yield 258 mg (87%).
$^1$H-NMR (deuteriochloroform): δ 0.93 (3H, t, H-17), 1.05 (3H, d, H-18), 1.83 (3H, s, H-22), 2.26 (6H, s, Me$_2$N), 4.19 (1H, d, H-1'), 4.73 (1H, m, H-15), 5.77 (1H, d, J$_{13,14}$=10.5 Hz, H-13), 6.32 (1H, d, J$_{10,11}$=15.5 Hz, H-10), 6.60 (2H, m, aromatic), 7.32 (1H, d, H-11), 7.45 (1H, m, aromatic), 8.17 (1H, m, aromatic), 9.70 (1H, s, H-20).

MKT-6109: yield 203 mg (74%).
$^1$H-NMR (deuteriochloroform): δ 0.93 (3H, t, H-17), 1.04 (3H, d, H-18), 1.83 (3H, s, H-22), 2.20 (3H, s, CH$_2$N(Me)), 2.26 (6H, s, Me$_2$N), 4.19 (1H, d, H-1'), 4.68 (1H, m, H-15), 5.73 (1H, d, J$_{13,14}$=10 Hz, H-13), 6.29 (1H, d, J$_{10,11}$=15.5 Hz, H-10), 7.32 (1H, d, H-11), 9.70 (1H, s, H-20).

MKT-6110: yield 209 mg (76%).
$^1$H-NMR (deuteriochloroform): δ 0.80 (6H, slightly br s, CH-Mex2), 0.92 (3H, t, H-17), 1.04 (3H, d, H-18), 1.82 (3H, s, H-22), 2.26 (6H, s, Me$_2$N), 4.19 (1H, d, H-1'), 4.69 (1H, m, H-15), 5.75 (1H, d, J$_{13,14}$=10 Hz, H-13), 6.30 (1H, d, J$_{10,11}$=15.5 Hz, H-10), 7.32 (1H, d, H-11), 9.70 (1H, s, H-20).

MKT-6111: yield 189 mg (72%).
$^1$H-NMR (deuteriochloroform): δ 0.93 (3H, t, H-17), 1.04 (3H, d, H-18), 1.82 (3H, s, H-22), 2.26 (6H, s, Me$_2$N), 4.19 (1H, d, H-1'), 4.71 (1H, m, H-15), 5.59&5.70 (each 1H, d, CH=CH), 5.78 (1H, d, J$_{13,14}$=10.5 Hz, H-13), 6.30 (1H, d, J$_{10,11}$=15.5 Hz, H-19), 7.32 (1H, d, H-11), 9.70 (1H, s, H-20).

MKT-6112: yield 224 mg (79%).
$^1$H-NMR (deuteriochloroform): δ 0.91 (3H, t, H-17), 1.04 (3H, d, H-18), 1.81 (3H, s, H-22), 2.24 (3H, s, CH$_2$N(Me)), 2.26 (6H, s, Me$_2$N), 4.19 (1H, d, H-1'), 4.70 (1H, m, H-15), 5.73 (1H, d, J$_{13,14}$=10 Hz, H-13), 6.30 (1H, d, J$_{10,11}$=15.5 Hz, H-10), 9.70 (1H, s, H-20).

MKT-6113: yield 722 mg (79%).
$^1$H-NMR (deuteriochloroform): δ 0.92 (3H, t, H-17), 1.04 (3H, d, H-18), 1.81 (3H, s, H-22), 2.26 (6H, s, Me$_2$N), 3.67 (2H, t, CH$_2$CH$_2$OH), 4.19 (1H, d, H-1'), 4.70 (1H, m, H-15), 5.75 (1H, d, J$_{13,14}$=10 Hz, H-13), 6.30 (1H, d, J$_{10,11}$=15.5 Hz, H-10), 7.32 (1H, d, H-11), 9.70 (1H, s, H-20).

MKT-6114: yield 185 mg (67%).
$^3$H-NMR (deuteriodimethylsulfoxide): δ 1.82 (3H, s, H-22), 2.20 (6H, s, Me$_2$N), 4.09 (1H, d, H-1'), 4.34 (1H, t, CH$_2$OH), 4.60 (1H, m, H-15), 5.48 (1H, dd, J$_{13,14}$=10.5 Hz, H-13), 6.48 (1H, d, J$_{10,11}$=15.5 Hz, H-10), 7.09 (1H, dd, H-11), 9.62 (1H, s, H-20).

MKT-6115: yield 145 mg (57%).
$^1$H-NMR (deuteriochloroform): δ 0.99 (3H, t, H-17), 1.04 (3H, d, H-18), 1.69 (3H, s, H-22), 2.26 (6H, s, Me$_2$N), 4.18 (1H, d, H-1'), 4.83 (1H, m, H-15), 5.64 (1H, d, J$_{13,14}$=10.5 Hz, H-13), 6.31 (1H, d, $J_{10,11}$=15.5 Hz, H-10), 6.84 (1H, t), 7.00 (1H, t), 7.20 (1H, d, H-11), 7.41 (1H, t), 9.70 (1H, s, H-20).

Example 4

Production of 23-Thioether Derivatives 300 mg of Compound (3) prepared in Reference Example 2 was dissolved in 6 mL of acetonitrile, to which various thioalcohols (1.2 molar to 1.5 molar equivalents for Compound (3)) and 16 mg of sodium hydride were added and allowed to react for 1 hour to 4 hours at room temperature while stirring. Next, 5 mL of 0.3 M hydrochloric acid was added to the reaction solution and left at rest for 2 hours at room temperature to remove the acetal group. The reaction solution was concentrated to a small amount, which was neutralized by adding 5% aqueous sodium hydrogen carbonate solution. The resulting precipitate was extracted with chloroform. The organic layer was washed with water, dried with anhydrous sodium sulfate, and concentrated. The residue obtained was purified by silica gel column chromatography (developed with chloroform:methanol:28% aqueous ammonia=10:1:0.1) to give various 23-thioether derivatives as a colorless solid as shown below. Reaction formula is shown below.

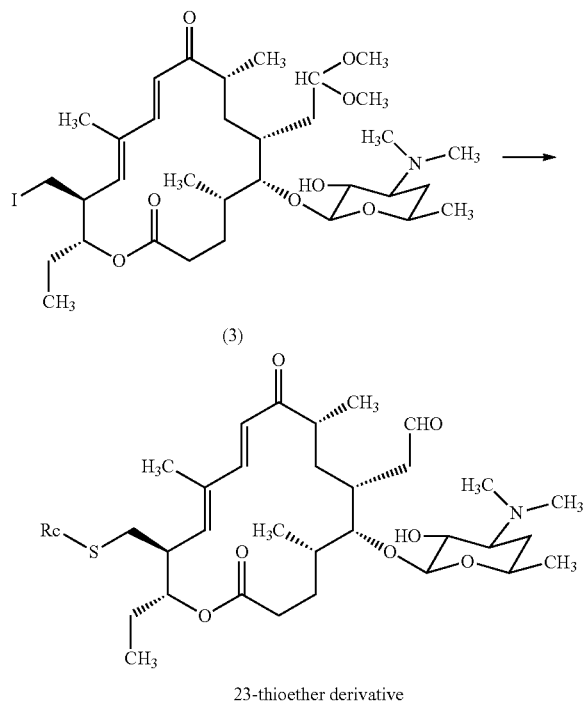

The yield and analytical values of the respective 23-thioether derivatives obtained are shown below.

MKT-3003: yield 211 mg (77%).
$^1$H-NMR (deuteriochloroform): δ 0.97 (3H, t, H-17), 1.04 (3H, d, H-18), 1.73 (3H, s, H-22), 2.26 (6H, s, Me$_2$N), 3.18 (1H, dd, $J_{2',3'}$=10.5 Hz, H-2'), 3.60 (1H, dd, H-23b), 4.18 (1H, d, $J_{1',2'}$=7.5 Hz, H-1'), 4.87 (1H, m, H-15), 5.73 (1H, d, $J_{13,14}$=10 Hz, H-13), 6.30 (1H, d, $J_{10,11}$=15.5 Hz, H-10), 6.93 (1H, ddd, aromatic), 7.13 (1H, dd, aromatic), 7.26 (1H, d, H-11), 7.45 (1H, ddd, aromatic), 8.42 (1H, ddd, aromatic), 9.70 (1H, s, H-20).

MKT-3801: yield 232 mg (81%).
$^1$H-NMR (deuteriochloroform): δ 0.86 (3H, t, H-17), 1.03 (3H, d, H-18), 1.72 (3H, s, H-22), 2.26 (6H, s, Me$_2$N), 2.75 (1H, dd, H-23a), 3.03 (1H, dd, H-23b), 3.18 (1H, dd, $J_{2',3'}$=10 Hz, H-2'), 3.80 (3H, s, MeO), 4.18 (1H, d, $J_{1',2'}$=7.5 Hz, H-1'), 4.78 (1H, m, H-15), 5.68 (1H, d, $J_{13,14}$=10 Hz, H-13), 6.32 (1H, d, $J_{10,11}$=15.5 Hz, H-10), 6.83&7.31 (each 2H, d, aromatic), 7.28 (1H, d, H-11), 9.70 (1H, s, H-20).

MKT-3802: yield 263 mg (96%).
$^1$H-NMR (deuteriochloroform): δ 0.99 (3H, t, H-17), 1.04 (3H, d, H-18), 1.76 (3H, s, H-22), 2.26 (6H, s, Me$_2$N), 3.18 (1H, dd, $J_{2',3'}$=10 Hz, H-2'), 3.50 (1H, br d, H-23b), 4.18 (1H, d, $J_{1',2'}$=7.5 Hz, H-1'), 4.88 (1H, m, H-15), 5.73 (1H, d, $J_{13,14}$=10 Hz, H-13), 6.31 (1H, d, $J_{10,11}$=15.5 Hz, H-10), 6.97 (1H, t, aromatic), 7.25 (1H, d, H-11), 8.51 (2H, d, aromatic), 9.70 (1H, s, H-20).

MKT-5801: yield 191 mg (70%).
$^1$H-NMR (deuteriochloroform): δ 0.97 (3H, t, H-17), 1.04 (3H, d, H-18), 1.75 (3H, s, H-22), 2.26 (6H, s, Me$_2$N), 4.18 (1H, d, H-1'), 4.87 (1H, m, H-15), 5.69 (1H, d, $J_{13,14}$=10 Hz, H-13), 6.35 (1H, d, $J_{10,11}$=15.5 Hz, H-10), 7.08&8.41 (each 2H, d, aromatic), 9.70 (1H, s, H-20).

MKT-5802: yield 254 mg (90%).
$^1$H-NMR (deuteriochloroform): δ 0.97 (3H, t, H-17), 1.04 (3H, d, H-18), 1.75 (3H, s, H-22), 2.26 (6H, s, Me$_2$N), 2.72 (3H, s, N=C(Me)-S), 4.18 (1H, d, H-1'), 4.83 (1H, m, H-15), 5.67 (1H, d, $J_{13,14}$=10.5 Hz, H-13), 6.33 (1H, d, $J_{10,11}$=15.5 Hz, H-10), 7.27 (1H, d, H-11), 9.70 (1H, s, H-20).

MKT-5803: yield 243 mg (84%).
$^1$H-NMR (deuteriochloroform). δ 1.77 (3H, s, H-22), 2.26 (6H, s, Me$_2$N), 4.18 (1H, d, H-1'), 4.89 (1H, m, H-15), 5.70 (1H, d, $J_{13,14}$=10.5 Hz, H-13), 6.35 (1H, d, $J_{10,11}$=15.5 Hz, H-10), 9.70 (1H, s, H-20).

MKT-5804: yield 241 mg (86%).
$^1$H-NMR (deuteriochloroform): δ 0.99 (3H, t, H-17), 1.04 (3H, d, H-18), 1.75 (3H, s, H-22), 2.26 (6H, s, Me$_2$N), 2.45 (3H, s, N=C(Me)-C), 4.18 (1H, d, H-1'), 4.87 (1H, m, H-15), 5.73 (1H, d, $J_{13,14}$=10 Hz, H-13), 6.30 (1H, d, $J_{10,11}$=15.5 Hz, H-10), 6.83&8.34 (each 1H, d, aromatic), 9.70 (1H, s, H-20).

MKT-5805: yield 273 mg (92%).
$^1$H-NMR (deuteriochloroform): δ 0.89 (3H, t, H-17), 1.03 (3H, d, H-18), 1.70 (3H, s, H-22), 2.17 (3H, s, Ac), 2.26 (6H, s, Me$_2$N), 4.18 (1H, d, H-1'), 4.78 (1H, m, H-15), 5.62 (1H, d, $J_{13,14}$=10 Hz, H-13), 6.30 (1H, d, $J_{10,11}$=15.5 Hz, H-10), 7.22 (1H, d, H-11), 9.70 (1H, s, H-20).

MKT-5806: yield 261 mg (93%).
$^1$H-NMR (deuteriochloroform): δ 0.88 (3H, t, H-17), 1.03 (3H, d, H-18), 1.71 (3H, s, H-22), 2.26 (6H, s, Me$_2$N), 4.18 (1H, d, H-1'), 4.80 (1H, m, H-15), 5.70 (1H, d, $J_{13,14}$=10 Hz, H-13), 6.33 (1H, d, $J_{10,11}$=15.5 Hz, H-10), 9.70 (1H, s, H-20).

MKT-5807: yield 238 mg (87%).
$^1$H-NMR (deuteriochloroform): δ 0.90 (3H, t, H-17), 1.03 (3H, d, H-18), 1.70 (3H, s, H-22), 2.26 (6H, s, Me$_2$N), 4.18 (1H, d, H-1'), 4.82 (1H, m, H-15), 5.71 (1H, d, $J_{13,14}$=10 Hz, H-13), 6.32 (1H, d, $J_{10,11}$=15.5 Hz, H-10), 9.70 (1H, s, H-20).

MKT-5808: yield 235 mg (85%).
$^1$H-NMR (deuteriochloroform): δ 0.95 (3H, t, H-17), 1.04 (3H, d, H-18), 1.74 (3H, s, H-22), 2.26 (6H, s, Me$_2$N), 4.18 (1H, d, H-1'), 4.84 (1H, m, H-15), 5.68 (1H, d, $J_{13,14}$=9 Hz, H-13), 6.32 (1H, d, $J_{10,11}$=15.5 Hz, H-10), 7.21&7.67 (each 1H, d, aromatic), 7.26 (1H, d, H-11), 9.70 (1H, s, H-20).

MKT-5809: yield 229 mg (82%).
$^1$H-NMR (deuteriochloroform): δ 0.86 (3H, t, H-17), 1.03 (3H, d, H-18), 1.79 (3H, s, H-22), 2.26 (6H, s, Me$_2$N), 3.68 (2H, s, PhCH$_2$), 4.18 (1H, d, H-1'), 4.70 (1H, m, H-15), 5.64 (1H, d, $J_{13,14}$=10.5 Hz, H-13), 6.32 (1H, d, $J_{10,11}$=15.5 Hz, H-10), 9.70 (1H, s, H-20).

MKT-5810: yield 236 mg (85%).

$^1$H-NMR (deuteriochloroform). δ 0.95 (3H, t, H-17), 1.04 (3H, d, H-18), 1.80 (3H, s, H-22), 2.26 (6H, s, Me$_2$N), 4.80 (1H, m, H-15), 5.66 (1H, d, $J_{13,14}$=10 Hz, H-13), 6.34 (1H, d, $J_{10,11}$=15.5 Hz, H-10), 7.28 (1H, d, H-11), 9.70 (1H, s, H-20).

MKT-5811: yield 245 mg (89%).

$^1$H-NMR (deuteriochloroform): δ 0.90 (3H, t, H-17), 1.03 (3H, d, H-18), 1.72 (3H, s, H-22), 2.26 (6H, s, Me$_2$N), 3.53 (3H, s, NMe), 4.18 (1H, d, H-1'), 4.77 (1H, m, H-15), 5.67 (1H, d, $J_{13,14}$=9.5 Hz, H-13), 6.31 (1H, d, $J_{10,11}$=15.5 Hz, H-10), 6.89 (1H, d), 7.06 (1H, d), 7.26 (1H, d, H-11), 9.70 (1H, s, H-20).

MKT-5812: yield 248 mg (90%).

$^1$H-NMR (deuteriochloroform): δ 0.98 (3H, t, H-17), 1.04 (3H, d, H-18), 1.73 (3H, s, H-22), 2.26 (6H, s, Me$_2$N), 3.87 (3H, s, NMe), 4.18 (1H, d, H-1'), 4.83 (1H, m, H-15), 5.67 (1H, d, $J_{13,14}$=10.5 Hz, H-13), 6.35 (1H, d, $J_{10,11}$=15.5 Hz, H-10), 7.27 (1H, d, H-11), 9.70 (1H, s, H-20).

MKT-5813: yield 234 mg (85%).

$^1$H-NMR (deuteriochloroform): δ 0.91 (3H, t, H-17), 1.04 (3H, d, H-18), 1.81 (3H, s, H-22), 2.26 (6H, s, Me$_2$N), 3.68 (2H, s, SCH$_2$), 4.18 (1H, d, H-1'), 4.74 (1H, m, H-15), 5.65 (1H, d, $J_{13,14}$=10.5 Hz, H-13), 6.18 (1H, d), 7.30 (1H, d, H-11), 7.34 (1H, d), 9.70 (1H, s, H-20).

MKT-5814: yield 227 mg (82%).

$^1$H-NMR (deuteriochloroform): δ 0.94 (3H, t, H-17), 1.04 (3H, d, H-18), 1.75 (3H, s, H-22), 2.26 (6H, s, Me$_2$N), 3.53 (3H, s, NMe), 4.18 (1H, d, H-1'), 4.81 (1H, m, H-15), 5.70 (1H, d, $J_{13,14}$=10.5 Hz, H-13), 6.34 (1H, d, $J_{10,11}$=15.5 Hz, H-10), 7.28 (1H, d, H-11), 8.10 (1H, s, N=CH—N), 9.70 (1H, s, H-20).

Example 5

Production of 23-Ether Derivatives [1]

(i) 500 mg of a compound described in Carbohydrate Research 274 (1995) 269-278 (Compound (1) in the following reaction formula) was dissolved in 10 mL of dichloromethane, to which 320 mg of tetrabutylammonium iodide, 3 mL of 50% aqueous sodium hydroxide solution, and various organic bromides (2 molar equivalents for Compound (1)) were added and stirred at room temperature. After 30 minutes, organic bromides (2 molar equivalents for Compound (1)) were further added and allowed to react for another 30 minutes with stirring. Next, the reaction solution, separated into two layers, was diluted with chloroform. The organic layer was washed with dilute hydrochloric acid and water, successively, dried with anhydrous sodium sulfate, and concentrated. The syrup obtained was purified by silica gel column chromatography (developed with chloroform:methanol:28% aqueous ammonia=20:1:0.1) to give dimethylacetals of 23-ether derivatives as a colorless solid.

The yield of the derivative where Rb is CH$_2$=CHCH$_2$— was 176 mg (33%), and the yield of the derivative where Rb is PhCH$_2$— was 86 mg (15%).

(ii) The total amount of each of dimethylacetals of 23-ether derivatives prepared above (i) was dissolved in 2 mL to 2.5 mL of acetonitrile. To this solution, 1 mL to 1.7 mL of 0.3 M hydrochloric acid was added and left at rest for 2 hours at room temperature to remove the acetal group. The reaction solution was concentrated to a small amount, which was neutralized by adding 5% aqueous sodium hydrogen carbonate solution. Then, the resulting precipitate was to extracted with chloroform. The organic layer was washed with water, dried with anhydrous sodium sulfate, and concentrated. The residue obtained was purified by silica gel column chromatography (developed with chloroform:methanol=10:1) to give various 23-ether derivatives as a colorless solid as shown below. Reaction formula is is shown below.

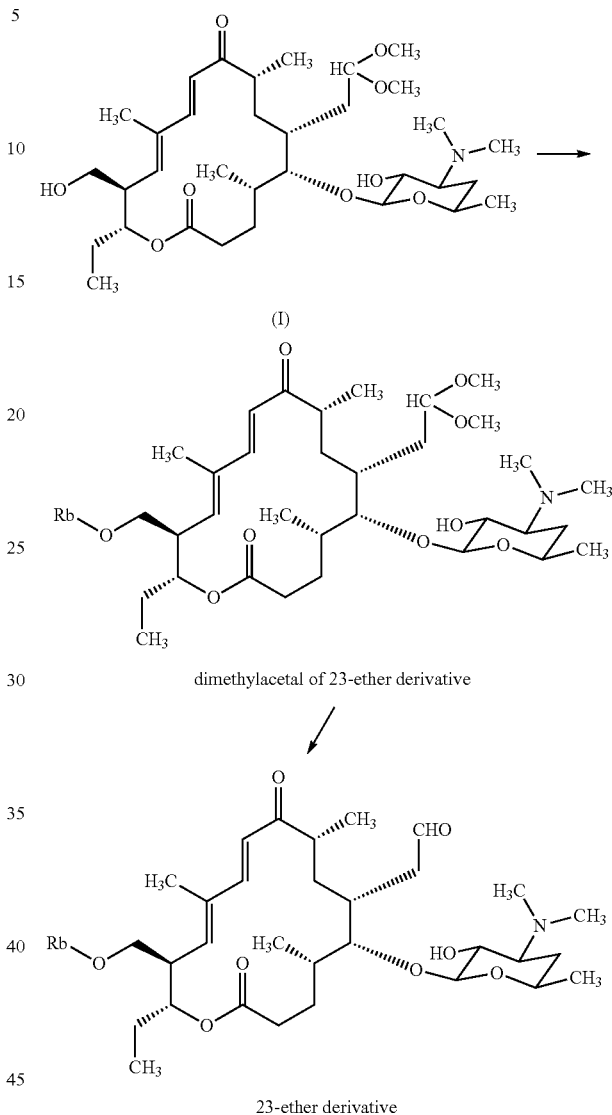

dimethylacetal of 23-ether derivative 23-ether derivative

The yield and analytical values of the respective 23-ether derivatives obtained are shown below.

MKT-3701: yield 155 mg (31%, based on Compound (1)).

$^1$H-NMR (deuteriochloroform): δ 0.93 (3H, t, H-17), 1.04 (3H, d, H-18), 1.83 (3H, s, H-22), 2.26 (6H, s, Me$_2$N), 3.18 (1H, dd, $J_{2',3'}$=10 Hz, H-2'), 3.49 (2H, d, H-23), 3.95 (2H, m), 4.18 (1H, d, $J_{1',2'}$=7.5 Hz, H-1'), 4.89 (1H, m, H-15), 5.18 (1H, slightly br d), 5.25 (1H, slightly br d), 5.84 (1H, d, $J_{13,14}$=10.5 Hz, H-13), 5.86 (1H, m), 6.33 (1H, d, $J_{10,11}$=15.5 Hz, H-10), 7.31 (1H, d, H-11), 9.70 (1H, s, H-20).

MKT-3702: yield 79 mg (15%, based on Compound (1)).

$^1$H-NMR (deuteriochloroform): δ 0.91 (3H, t, H-17), 1.04 (3H, d, H-18), 1.82 (3H, s, H-22), 2.26 (6H, s, Me$_2$N), 3.18 (1H, dd, $J_{2',3'}$=10 Hz, H-2'), 3.51 (2H, d, H-23), 4.19 (1H, d, $J_{1',2'}$=7.5 Hz, H-1'), 4.50 (2H, ABq, PhCH$_2$O), 4.90 (1H, m, H-15), 5.87 (1H, d, $J_{13,14}$=10.5 Hz, H-13), 6.33 is (1H, d, $J_{10,11}$=15.5 Hz, H-10), 9.70 (1H, s, H-20).

Example 6-1

Production of 23-Ether Derivatives [2]

500 mg of Compound (1) in the reaction formula of Example 5 was dissolved in 7.5 mL of toluene. To this solution, triphenylphosphine (1.2 molar to 1.5 molar equivalents for Compound (1)), toluene solution of azodicarboxylic acid diethyl ester (1.2 molar to 1.5 molar equivalents for Compound (1)), and various aromatic alcohols (1 molar to 1.2 molar equivalents for Compound (1)) were added under cooling with ice and allowed to react for 1 hour to 2 hours at a temperature ranging from ice-cold temperature to room temperature. Addition of a small amount of methanol to the reaction solution followed by concentration gave a residue, which was extracted with ethyl acetate. The extract solution was washed with aqueous sodium hydrogen carbonate solution and water, successively, dried with anhydrous sodium sulfate, and concentrated. The thus obtained solid was dissolved in 6 mL to 8 mL of acetonitrile. To this solution, 3 mL to 4 mL of 0.3 M hydrochloric acid was added and left at rest for 1 hour to 2 hours at room temperature to remove the acetal group. The reaction solution was concentrated to a small amount, which was neutralized by adding aqueous sodium hydrogen carbonate solution. Then, the resulting precipitate was extracted with chloroform. The organic layer was washed with water, dried with anhydrous sodium sulfate, and concentrated. The residue obtained was purified by silica gel column chromatography (developed with chloroform:methanol:28% aqueous ammonia=10:1:0.1) to give various 23-ether derivatives as a colorless solid.

The yield and analytical values of the respective 23-ether derivatives obtained are shown below.

MKT-5701: yield 184 mg (35%, based on Compound (1)).
$^1$H-NMR (deuteriochloroform): δ 0.96 (3H, t, H-17), 1.05 (3H, d, H-18), 1.84 (3H, s, H-22), 2.27 (6H, s, Me$_2$N), 4.19 (1H, d, H-1'), 5.05 (1H, m, H-15), 5.95 (1H, d, $J_{13,14}$=10.5 Hz, H-13), 6.34 (1H, d, $J_{10,11}$=15.5 Hz, H-10), 9.70 (1H, s, H-20).

MKT-5704: yield 403 mg (72%, based on Compound (1)).
$^1$H-NMR (deuteriochloroform): δ0.95 (3H, t, H-17), 1.05 (3H, d, H-18), 1.86 (3H, s, H-22), 2.26 (6H, s, Me$_2$N), 2.93 (6H, s, Me$_2$N—C$_6$H$_4$—O—), 4.19 (1H, d, H-1'), 5.08 (1H, m, H-15), 5.97 (1H, d, $J_{13,14}$=10.5 Hz, H-13), 7.13 (1H, t, aromatic), 7.32 (1H, d, $J_{10,11}$=15.5 Hz, H-11), 9.70 (1H, s, H-20).

MKT-5705: yield 420 mg (80%, based on Compound (1)).
$^1$H-NMR (deuteriochloroform). δ 0.96 (3H, t, H-17), 1.05 (3H, d, H-18), 1.85 (3H, s, H-22), 2.27 (6H, s, Me$_2$N), 4.19 (1H, d, H-1'), 9.70 (1H, s, H-20).

Example 6-2

Production of 23-Ether Derivatives [3]

400 mg of Compound (2) prepared in Reference Example 1 was dissolved in 8 mL of dichloromethane, to which 0.32 mL of N,N-diisopropylethylamine and 0.17 mL of benzyl chloromethyl ether were added and allowed to react overnight at room temperature. The reaction solution was diluted with chloroform. The organic layer is was washed with 5% aqueous sodium hydrogen carbonate solution and water, successively, dried with anhydrous sodium sulfate, and concentrated. The residue obtained was dissolved in 10 mL of methanol and left at rest overnight at room temperature to eliminate the acetyl group. Next, this reaction solution was concentrated and the residue obtained was dissolved in 10 mL of acetonitrile, to which 8 mL of 0.3 M hydrochloric acid was added and left at rest for 2 hours at room temperature to remove the acetal group. The reaction solution was concentrated to a small amount, neutralized by adding 5% aqueous sodium hydrogen carbonate solution, and then the resulting precipitate was extracted with chloroform. The organic layer was washed with water, dried with anhydrous sodium sulfate, and concentrated. The residue obtained was purified by silica gel column chromatography (developed with chloroform: methanol=20:1) to give 270 mg of MKT-3703, a 23-ether derivative, as a colorless solid. The yield was 64%. Reaction formula is shown below.

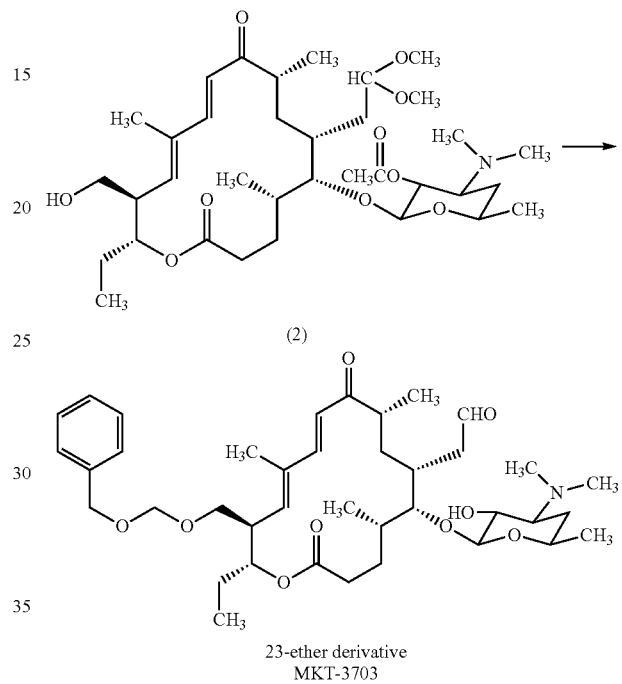

23-ether derivative
MKT-3703

The yield and analytical values of the obtained MKT-3703, a 23-ether derivative, as a colorless solid are shown below.

MKT-3703: yield 270 mg (64%).
$^1$H-NMR (deuteriochloroform). δ 0.93 (3H, t, H-17), 1.05 (3H, d, H-18), 1.83 (3H, s, H-22), 2.26 (6H, s, Me$_2$N), 3.19 (1H, dd, $J_{2',3'}$=10 Hz, H-2'), 3.65 (2H, m, H-23), 4.19 (1H, d, $J_{1',2'}$=7.5 Hz, H-1'), 4.58 (2H, ABq, CH$_2$), 4.74 (2H, s, CH$_2$), 4.93 (1H, m, H-15), 5.88 (1H, d, $J_{13,14}$=10.5 Hz, H-13), 6.34 (1H, d, $J_{10,11}$=15.5 Hz, H-10), 9.70 (1H, s, H-20).

Example 7-1

Production of 23-Halogen Derivatives [1]

200 mg of Compound (3) prepared in Reference Example 2 was dissolved in 3 mL of acetonitrile, to which 4 mL of 0.1 M hydrochloric acid was added and left at rest for 2 hours at room temperature to remove the acetal group. The reaction solution was concentrated to a small amount, which was neutralized by adding 5% aqueous sodium hydrogen carbonate solution. Then, the resulting precipitate was extracted with chloroform. The organic layer was washed with water, dried with anhydrous sodium sulfate, and concentrated. The residue obtained was purified by silica gel column chromatography (developed with chloroform:methanol=15:1) to give 160 mg of MKT-3001, a 23-halogen derivative, as a colorless solid. The yield was 85%. Reaction formula is shown below.

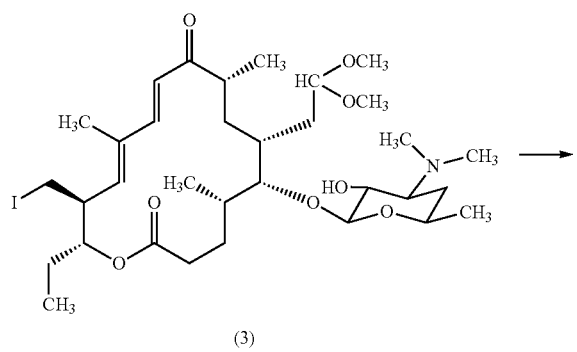

(3)

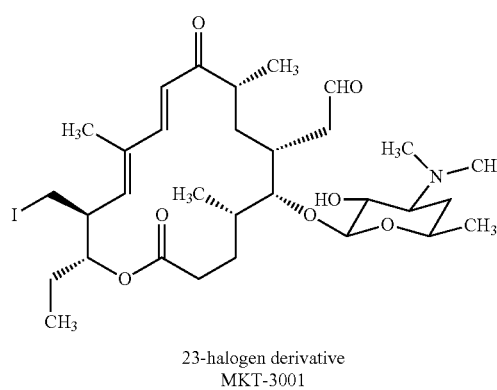

23-halogen derivative
MKT-3001

The analytical values of MKT-3001 are shown below.
$^1$H-NMR (deuteriochloroform): δ 0.95 (3H, t, H-17), 1.04 (3H, d, H-18), 1.84 (3H, s, H-22), 2.26 (6H, s, Me$_2$N), 3.07 (1H, t, H-23a), 3.19 (1H, dd, J$_{2',3'}$=10 Hz, H-2'), 3.26 (1H, dd, H-23b), 4.18 (1H, d, J$_{1',2'}$=7.5 Hz, H-1'), 4.79 (1H, m, H-15), 5.69 (1H, d, J$_{13,14}$=10.5 Hz, H-13), 6.37 (1H, d, J$_{10,11}$=15.5 Hz, H-10), 7.32 (1H, d, H-11), 9.70 (1H, s, H-20).

Example 7-2

Production of 23-Halogen Derivatives [21]

500 mg of Compound (1) in the following reaction formula was dissolved in 10 mL of pyridine, to which 272 mg of 2-nitrobenzenesulfonyl chloride was added and allowed to react for 7 hours at room temperature. Excess reagent was destroyed by the addition of a small amount of water to the reaction solution. Then, the reaction solution was concentrated and the syrup obtained was extracted with chloroform, and the organic layer was washed with aqueous sodium hydrogen carbonate solution and water, successively, dried with anhydrous sodium sulfate, and concentrated. The thus-obtained protected form of 23-chloro derivative was dissolved in 10 mL of acetonitrile. To this solution, 5 mL of 0.3 M hydrochloric acid was added and left at rest for 2 hours at room temperature to to remove the acetal group. The reaction solution was neutralized by the addition of aqueous sodium hydrogen carbonate solution and then extracted with chloroform. The organic layer was washed with water, dried with anhydrous sodium sulfate, and concentrated. The residue obtained was purified by silica gel column chromatography is (developed with chloroform:methanol=10:1) to give 310 mg of MKT-3007 as a colorless solid. The yield was 65%.

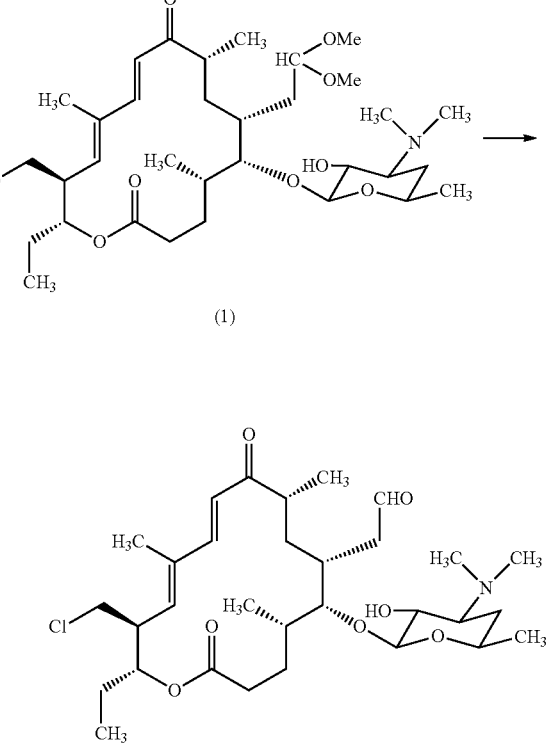

The analytical values of MKT-3007 are shown below.
$^1$H-NMR (deuteriochloroform): δ 0.96 (3H, t, H-17), 1.05 (3H, d, H-18), 1.84 (3H, s, H-22), 2.26 (6H, s, Me$_2$N), 4.19 (1H, d, H-1'), 4.94 (1H, m, H-15), 5.84 (1H, d, J$_{13,14}$=10 Hz, H-13), 6.36 (1H, d, J$_{10,11}$=15.5 Hz, H-10), 7.32 (1H, d, H-11), 9.70 (1H, s, H-20).

Reference Example 3

Production of 23-Azido-3,23,4'-trideoxymycamino-syltylonolide Dimethylacetal 3.52 g of Compound (3) prepared in Reference Example 2 was dissolved in 50 mL of N,N-dimethylformamide, to which 1.02 g of sodium azide was added and heated with stirring for 2 hours at 100° C. Concentration of the reaction solution followed by azeotropic distillation with xylene gave a residue, which was extracted with chloroform. The extract solution was washed with water, dried with anhydrous sodium sulfate, and concentrated to give 3.02 g of 23-azido-3,23,4'-trideoxyrnycaminosyltylonolide dimethylacetal (4) as a pale yellow solid. The yield was 97%. Reaction formula is shown below.

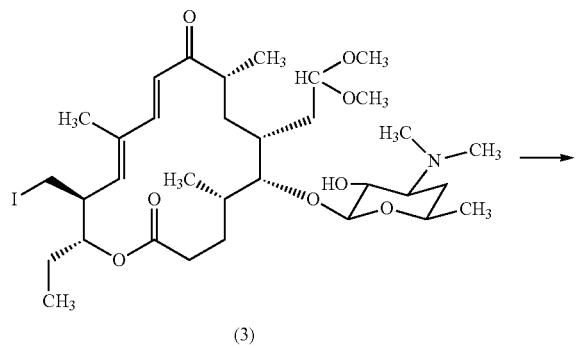

(3)

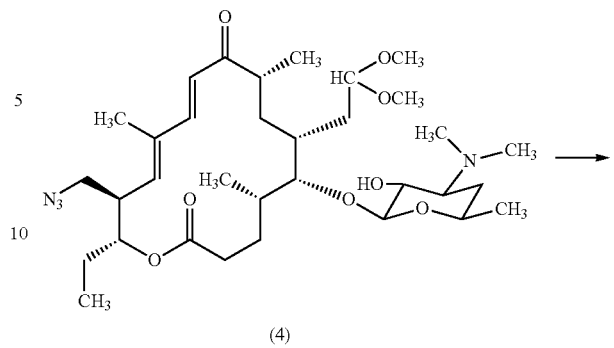

(4)

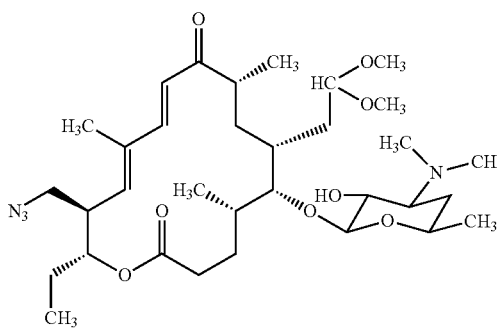

(4)

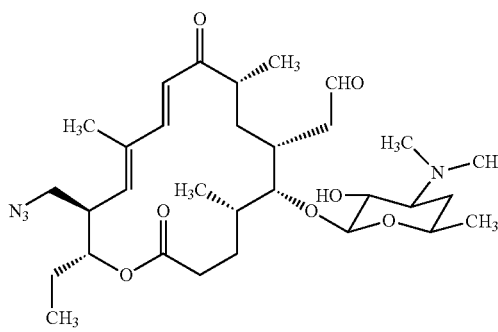

23-azido derivative
MKT-3004

The analytical values of Compound (4) obtained are shown below.

$^1$H-NMR (deuteriochloroform). δ 0.94 (3H, t, H-17), 1.06 (3H, d, H-18), 1.19 (3H, d, H-21), 1.25 (3H, d, H-6'), 1.84 (3H, s, H-22), 2.27 (6H, s, Me$_2$N), 3.22&3.31 (each 3H, s, MeO-20), 3.36 (1H, dd, H-23a), 3.46 (1H, dd, H-23b), 4.26 (1H, d, J$_{1',2'}$=7 Hz, H-1'), 4.56 (1H, dd, H-20), 4.82 (1H, m, H-15), 5.73 (1H, d, J$_{13,14}$=10.5 Hz, H-13), 6.35 (1H, d, J$_{10,11}$=15.5 Hz, H-10), 7.27 (1H, d, H-11).

IR (KBr disk): 2110 cm$^{-1}$ (N$_3$)

Example 8

Production of 23-Azido Derivative 273 mg of Compound (4) prepared in Reference Example 3 was dissolved in 6.8 mL of acetonitrile, to which 2.8 mL of 0.3 M hydrochloric acid was added and left at rest for 2 hours at room temperature to remove the acetal group. The reaction solution was concentrated to a small amount, which was neutralized by adding 5% aqueous sodium hydrogen carbonate solution. Then, the resulting precipitate was extracted with chloroform. The extract solution was washed with water, dried with anhydrous sodium sulfate, and concentrated. The residue obtained was purified by silica gel column chromatography (developed with chloroform:methanol=10:1) to give 183 mg of MKT-3004, a 23-azido derivative, as a colorless solid. The yield was 72%. Reaction formula is shown below.

The analytical values of MKT-3004 are shown below.

$^1$H-NMR (deuteriochloroform). δ 0.95 (3H, t, H-17), 1.05 (3H, d, H-18), 1.85 (3H, s, H-22), 2.26 (6H, s, Me$_2$N), 3.18 (1H, dd, J$_{2',3'}$=10 Hz, H-2'), 4.18 (1H, d, J$_{1',2'}$=7 Hz, H-1'), 4.83 (1H, m, H-15), 5.74 (1H, d, J$_{13,14}$=10.5 Hz, H-13), 6.36 (1H, d, J$_{10,11}$=15.5 Hz, H-10), 7.30 (1H, d, H-11), 9.70 (1H, s, H-20).

IR (KBr disk): 2110 cm$^{-1}$ (N$_3$)

Reference Example 4

Production of 23-Amino-3,23,4'-trideoxyrnycaminosyltylonolide Dimethylacetal 2.95 g of Compound (4) prepared in Reference Example 3 was dissolved in 40 mL of pyridine, to which 1.34 g of triphenylphosphine was added, left at rest for 1 hour at room temperature, then 10 mL of concentrated aqueous ammonia was further added, and left at rest for 3 hours at room temperature. The reaction solution was concentrated and the syrup obtained was dissolved in toluene. The organic layer was washed with water, dried with anhydrous sodium sulfate, and concentrated to give 3.66 g of crude Compound (5) as a pale yellow solid. 1.31 g of this crude Compound (5) was purified by silica gel column chromatography (developed with chloroform:methanol:28% aqueous ammonia=10:1: 0.1) to give 567 mg of 23-amino-3,23,4'-trideoxymycaminosyltylonolide dimethylacetal (5) as a colorless solid. The yield was 56%. Reaction formula is shown below.

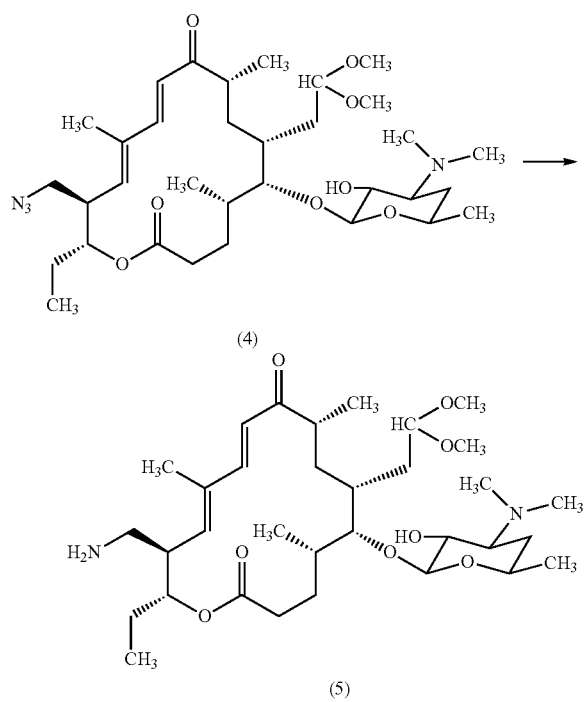

(4)

(5)

The analytical values of Compound (5) obtained are shown below.
$^1$H-NMR (deuteriochloroform): δ 0.93 (3H, t, H-17), 1.06 (3H, d, H-18), 1.20 (3H, d, H-21), 1.25 (3H, d, H-6'), 1.85 (3H, s, H-22), 2.27 (6H, s, Me$_2$N), 2.87 (1H, dd, H-23b), 3.22 & 3.31 (each 3H, s, MeO-20), 4.26 (1H, d, $J_{1',2'}$=7 Hz, H-1'), 4.56 (1H, dd, H-20), 4.75 (1H, m, H-15), 5.68 (1H, d, $J_{13,14}$=10 Hz, H-13), 6.35 (1H, d, $J_{10,11}$=15.5 Hz, H-10), 7.28 (1H, d, H-11).

Example 9

Production of 23-Amino Derivative 110 mg of Compound (5) prepared in Reference Example 4 was dissolved in 2.5 mL of a mixed solution of acetonitrile and water (acetonitrile:water=49:1). To this solution, 0.13 mL of trifluoroacetic acid was added and allowed to react for 30 minutes at room temperature. The reaction solution was concentrated to a small amount, to which diethyl ether was added. The resulting precipitate was collected, further washed with diethyl ether, and dried to give 132 mg of MKT-3005, a 23-amino derivative, as a colorless solid. The yield as its ditrifluoroacetic acid salt was 92%. Reaction formula is shown below.

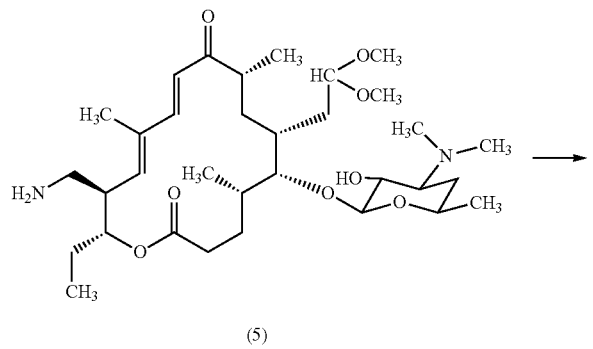

(5)

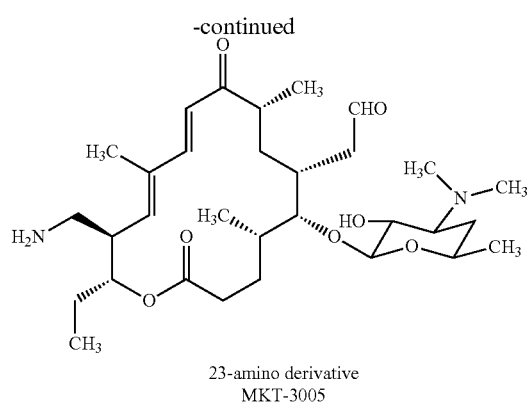

23-amino derivative
MKT-3005

The analytical values of MKT-3005 are shown below.
$^1$H-NMR (deuteriodimethylsulfoxide): δ 0.87 (3H, t, H-17), 0.96 (3H, d, H-18), 1.85 (3H, s, H-22), 2.67 (3H, d), 2.74 (3H, d), 4.19 (1H, d, $J_{1',2'}$=6.5 Hz, H-1'), 4.71 (1H, m, H-15), 5.65 (1H, d, $J_{13,14}$=10 Hz, H-13), 6.58 (1H, d, $J_{10,11}$=15.5 Hz, H-10), 7.10 (1H, d, H-11), 9.64 (1H, s, H-20).

Example 10

Production of 23-Amide Derivatives [1]

400 mg of the crude Compound (5) prepared in Reference Example 4 was dissolved in 8 mL of methanol, to which 4 mL of water, 170 mg of sodium bicarbonate, and various carboxylic acid chlorides (1.5 molar to 2.5 molar equivalents for Compound (5)) were added and stirred for 1 hour at room temperature. 10 mL of 5% aqueous sodium hydrogen carbonate solution was added to the pale yellow reaction suspension and then extracted with chloroform. The extract solution was washed with water, dried with anhydrous sodium sulfate, and concentrated. The residue obtained was dissolved in 10 mL of acetonitrile, to which 3 mL of 0.3 M of hydrochloric acid was added and left at rest for 2 hours to 3 hours at room temperature to remove the acetal group. The reaction solution was concentrated to a small amount, which was neutralized by adding 5% aqueous sodium hydrogen carbonate solution. The resulting precipitate was extracted with chloroform. The organic layer was washed with water, dried with anhydrous sodium sulfate, and concentrated. The residue obtained was purified by silica gel column chromatography (developed with chloroform:methanol=15:1) to give various 23-amide derivatives as a colorless solid. Reaction formula is shown below.

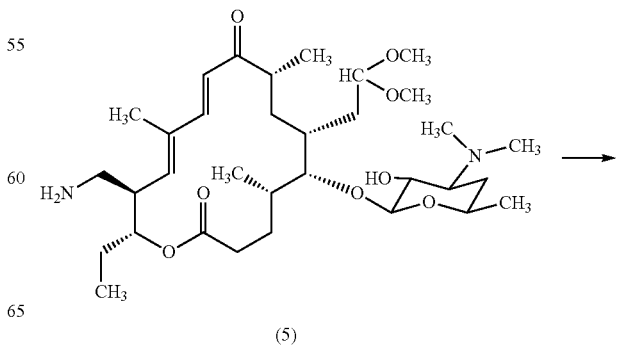

(5)

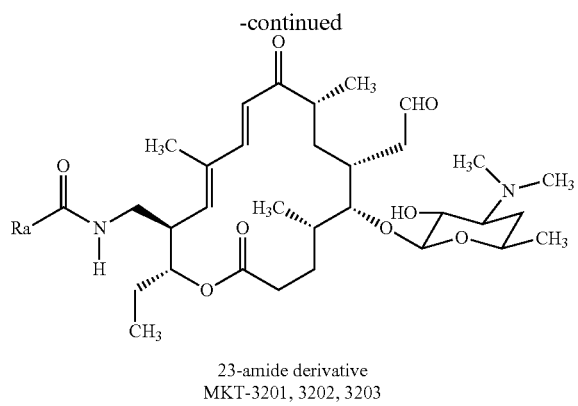

23-amide derivative
MKT-3201, 3202, 3203

The yields and analytical values of the 23-amide derivatives obtained are shown below.

MKT-3201: yield 225 mg (73%, based on Compound (4)).
$^1$H-NMR (deuteriochloroform): δ 0.95 (3H, t, H-17), 1.04 (3H, d, H-18), 1.82 (3H, s, H-22), 1.95 (3H, s, CH$_3$CO), 2.26 (6H, s, Me$_2$N), 3.18 (1H, dd, $J_{2',3'}$=10 Hz, H-2'), 3.69 (1H, ddd, H-23b), 4.19 (1H, d, $J_{1',2'}$=7.5 Hz, H-1'), 4.74 (1H, m, H-15), 5.48 (1H, br t, NH), 5.66 (1H, d, $J_{13,14}$=10 Hz, H-13), 6.34 (1H, d, $J_{10,11}$=15.5 Hz, H-10), 7.27 (1H, d, H-11), 9.70 (1H, s, H-20).

MKT-3202: yield 238 mg (70%, based on Compound (4)).
$^1$H-NMR (deuteriochloroform): δ 0.99 (3H, t, H-17), 1.05 (3H, d, H-18), 1.75 (3H, s, H-22), 2.26 (6H, s, Me$_2$N), 3.18 (1H, dd, $J_{2',3'}$=10 Hz, H-2'), 3.92 (1H, ddd, H-23b), 4.19 (1H, d, Hz, H-1'), 4.82 (1H, m, H-15), 5.75 (1H, d, $J_{13,14}$=10.5 Hz, H-13), 6.19 (1H, br t, NH), 6.36 (1H, d, $J_{10,11}$=15.5 Hz, H-10), 7.29 (1H, d, H-11), 7.42 (2H, t, aromatic), 7.49 (1H, t, aromatic), 7.69 (2H, d, aromatic), 9.70 (1H, s, H-20).

MKT-3203: yield 246 mg (71%, based on Compound (4)).
$^1$H-NMR (deuteriochloroform): δ 0.92 (3H, t, H-17), 1.03 (3H, d, H-18), 1.68 (3H, s, H-22), 2.26 (6H, s, Me$_2$N), 3.18 (1H, dd, $J_{2',3'}$=10 Hz, H-2'), 3.52 (2H, s, PhCH$_2$), 3.62 (1H, ddd, H-23b), 4.18 (1H, d, $J_{1',2'}$=7.5 Hz, H-1'), 4.70 (1H, m, H-15), 5.36 (1H, br t, NH), 5.47 (1H, d, $J_{13,14}$=10.5 Hz, H-13), 6.32 (1H, d, $J_{10,11}$=15.5 Hz, H-10), 7.16 (1H, d, H-11), 9.70 (1H, s, 11-20).

Example 11

Production of 23-Amide Derivatives [2]

400 mg of the crude Compound (5) prepared in Reference Example 4 was dissolved in 8 mL of tetrahydrofuran, to which 30 μL of triethylamine, 130 mg of N,N-bis(2-oxo-3-oxazolidinyl)phosphinic chloride, and various organic carboxylic acids (1.5 molar to 2 molar equivalents for Compound (5)) were added and stirred for 1 hour to 2 hours at room temperature. The reaction solution was concentrated and the residue obtained was dissolved in chloroform. The organic layer was washed with 5% aqueous sodium hydrogen carbonate solution and water, successively, dried with anhydrous sodium sulfate, and concentrated. The residue obtained was dissolved in 10 mL of acetonitrile. To this solution, 6 mL of 0.3 M hydrochloric acid was added and left at rest for 2 hours to 3 hours at room temperature to remove the acetal group. The reaction solution was concentrated to a small amount, which was neutralized by adding 5% aqueous sodium hydrogen carbonate solution. Then, the resulting precipitate was extracted with chloroform. The organic layer was washed with water, dried with anhydrous sodium sulfate, and concentrated. The residue obtained was purified by silica gel column chromatography (developed with chloroform:methanol=10:1) to give various 23-amide derivatives as a colorless solid. Reaction formula is shown below.

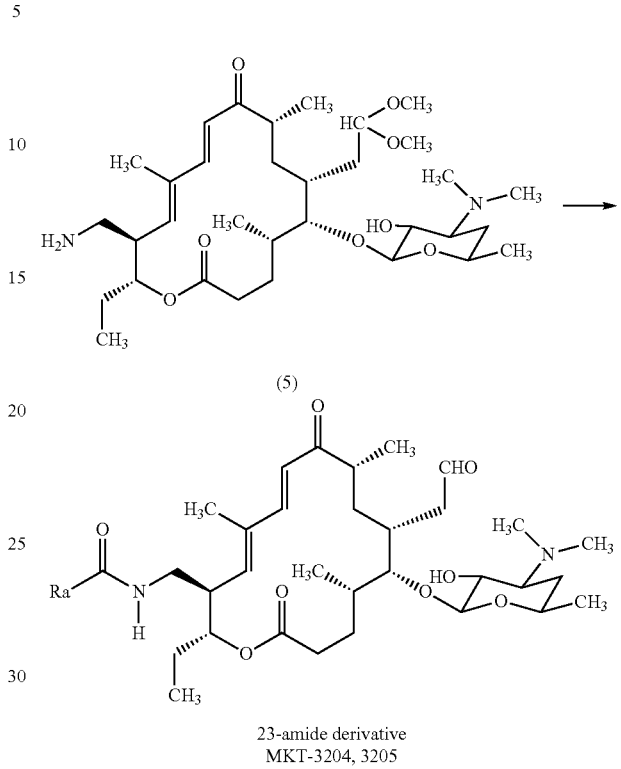

23-amide derivative
MKT-3204, 3205

The yields and analytical values of the 23-amide derivatives obtained are shown below.

MKT-3204: yield 231 mg (68%, based on Compound (4)).
$^1$H-NMR (deuteriochloroform). δ 0.99 (3H, t, H-17), 1.04 (3H, d, H-18), 1.81 (3H, s, H-22), 2.26 (6H, s, Me$_2$N), 3.18 (1H, dd, H-2'), 3.32 (1H, ddd, H-23a), 3.85 (1H, ddd, H-23b), 4.18 (1H, d, $J_{1',2'}$=7.5 Hz, H-1'), 4.86 (1H, m, H-15), 5.79 (1H, d, $J_{13,14}$=10.5 Hz, H-13), 6.35 (1H, d, $J_{10,11}$=15.5 Hz, H-10), 7.31 (1H, d, H-11), 7.40, 7.83, 8.10 (1H, br t, NH), 8.16, 8.53, 9.70 (1H, s, H-20).

MKT-3205: yield 230 mg (65%, based on Compound (4)).
$^1$H-NMR (deuteriochloroform): δ 0.99 (3H, t, H-17), 1.05 (3H, d, H-18), 1.83 (3H, s, H-22), 2.26 (6H, s, Me$_2$N), 3.18 (1H, dd, H-2'), 3.84 (1H, ddd, H-23b), 4.19 (1H, d, $J_{1',2'}$=7.5 Hz, H-1'), 4.79 (1H, m, H-15), 5.71 (1H, d, $J_{13,14}$=10.5 Hz, H-13), 5.77 (1H, br t, NH), 6.40 (1H, d, $J_{10,11}$=15.5 Hz, H-10), 6.42 (1H, d, olefin), 7.28 (1H, d, H-11), 7.61 (1H, d, olefin), 9.70 (1H, s, H-20).

MKT-3211: yield 300 mg (63%, based on Compound (4)).
$^1$H-NMR (deuteriochloroform): δ 1.03 (3H, d, H-18), 2.26 (3H, s, Me$_2$N), 4.18 (1H, d, H-1'), 9.70 (1H, s, H-20).

MKT-3212: yield 314 mg (67%, based on Compound (4)).
$^1$H-NMR (deuteriochloroform): δ 1.04 (3H, d, H-18), 2.26 (3H, s, Me$_2$N), 4.18 (1H, d, H-1'), 9.70 (1H, s, H-20).

MKT-3213: yield 334 mg (70%, based on Compound (4)).
$^1$H-NMR (deuteriochloroform): δ 1.04 (3H, d, H-18), 2.26 (3H, s, Me$_2$N), 4.19 (1H, d, H-1'), 9.70 (1H, s, H-20).

MKT-3214: yield 317 mg (69%, based on Compound (4)).
$^1$H-NMR (deuteriochloroform): δ 1.04 (3H, d, H-18), 2.26 (3H, s, Me$_2$N), 4.18 (1H, d, H-1'), 9.70 (1H, s, H-20).

MKT-3215: yield 291 mg (61%, based on Compound (4)).

$^1$H-NMR (deuteriochloroform): δ 1.03 (3H, d, H-18), 2.26 (3H, s, Me$_2$N), 4.18 (1H, d, H-1'), 9.71 (1H, s, H-20).

MKT-3216: yield 260 mg (58%, based on Compound (4)).
$^1$H-NMR (deuteriochloroform): δ 1.04 (3H, d, H-18), 2.26 (3H, s, Me$_2$N), 4.18 (1H, d, H-1'), 9.70 (1H, s, H-20).

Example 12

Production of 23-Amide Derivatives [3]

354 mg of the crude Compound (5) prepared in Reference Example 4 was dissolved in 6 mL of methanol, to which 11 μL of triethylamine and 123 mg of N-carbobenzoxyoxysuccinimide were added and allowed to react for 1 hour at room temperature. The reaction solution was concentrated and the residue obtained was dissolved in chloroform. The organic layer was washed with 5% aqueous sodium hydrogen sulfate solution, 5% aqueous sodium hydrogen carbonate solution and water, successively, dried with anhydrous sodium sulfate, and concentrated. Then, the residue obtained was dissolved in 9 mL of acetonitrile, to which 3 mL of 0.3 M hydrochloric acid was added and left at rest for 2 hours at room temperature to remove the acetal group. The reaction solution was concentrated to a small amount and then neutralized by adding 5% aqueous sodium hydrogen carbonate solution, and the resulting precipitate was extracted with chloroform. The organic layer was washed with water, dried with anhydrous sodium sulfate, and concentrated. The residue obtained was purified by silica gel column chromatography (developed with chloroform:methanol=10:1) to give 204 mg of MKT-3301, a 23-amide derivative, as a colorless solid. The yield based on Compound (4) was 65%. Reaction formula is shown below.

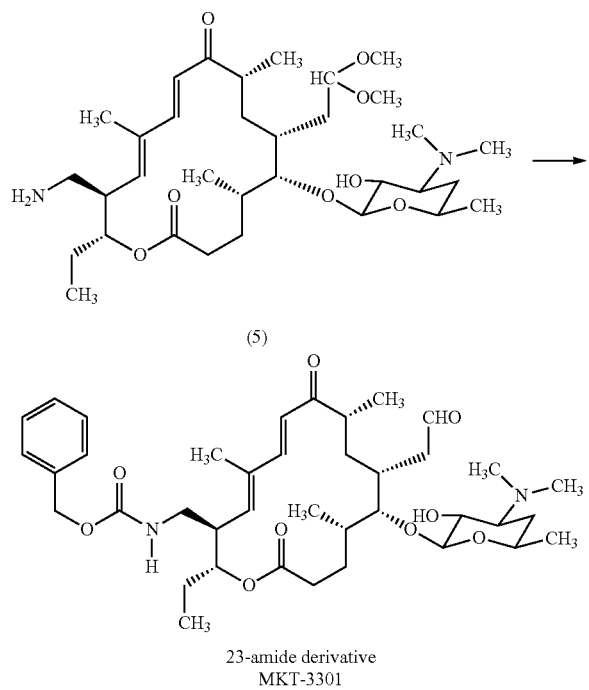

23-amide derivative
MKT-3301

The analytical values of MKT-3301 obtained are shown below.
$^1$H-NMR (deuteriochloroform): δ 0.95 (3H, t, H-17), 1.04 (3H, d, H-18), 1.79 (3H, s, H-22), 2.26 (6H, s, Me$_2$N), 3.06 (1H, ddd, H-23a), 3.18 (1H, dd, J$_{2',3'}$=10 Hz, H-2'), 3.54 (1H, m, H-23b), 4.18 (1H, d, J$_{1,2}$=7.5 Hz, H-1'), 4.75 (1H, broad, NH), 4.76 (1H, br t, H-15), 5.08 (2H, s, PhCH$_2$), 5.64 (1H, d, J$_{13,14}$=10.5 Hz, H-13), 6.34 (1H, d, J$_{10,11}$=15.5 Hz, H-10), 7.25 (1H, d, H-11), 9.70 (1H, s, H-20).

Example 13

Production of 23-Urea Derivatives 400 mg of the crude Compound (5) prepared in Reference Example 4 was dissolved in 8 mL of ethyl acetate, to which 0.1 mL of triethylamine and 0.1 mL of benzyl isocyanate were added and allowed to react for 1 hour at room temperature. Then, 0.2 mL of concentrated aqueous ammonia was added to the solution and concentrated. Next, the thus-obtained residue was dissolved in 10 mL of acetonitrile, and to this solution, 3 mL of 0.3 M hydrochloric acid was added and left at rest for 3 hours at room temperature to remove the acetal group. The reaction solution was concentrated to a small amount, which was neutralized by adding 5% aqueous sodium hydrogen carbonate solution. The resulting precipitate was extracted with chloroform. The organic layer was washed with water, dried with anhydrous sodium sulfate, and concentrated. The residue obtained was purified by silica gel column chromatography (developed with chloroform:methanol=10:1) to give 202 mg of MKT-3401, a 23-urea derivative, as a colorless solid. The yield based on Compound (4) was 57%. Reaction formula is shown below.

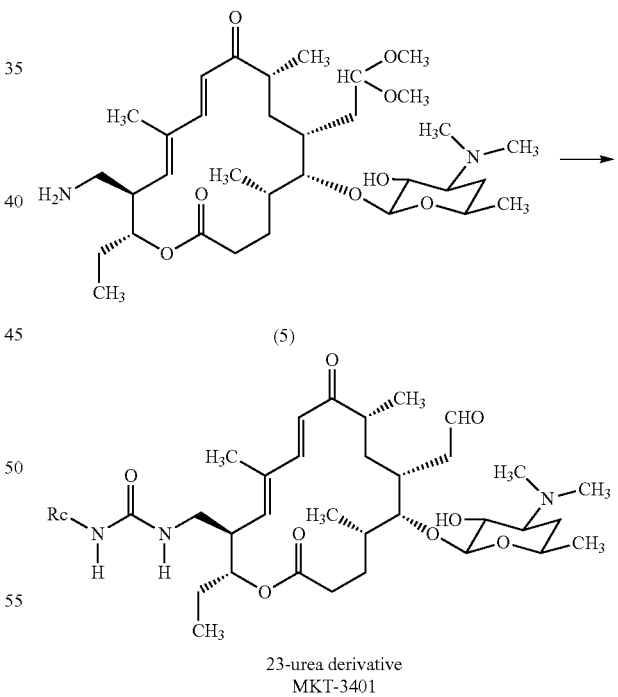

23-urea derivative
MKT-3401

The analytical values of MKT-3401 obtained are shown below.
$^1$H-NMR (deuteriochloroform): δ 0.93 (3H, t, H-17), 1.03 (3H, d, H-18), 1.78 (3H, s, H-22), 2.26 (6H, s, Me$_2$N), 3.06 (1H, ddd, H-23a), 3.18 (1H, dd, J$_{2',3'}$=10 Hz, H-2'), 3.56 (1H, ddd, H-23b), 4.18 (1H, d, J$_{1',2'}$=7.5 Hz, H-1'), 4.36 (2H, d, PhCH$_2$), 4.59 (1H, br t, NH), 4.76 (1H, m, H-15), 4.87 (1H, t, PhCH$_2$NH), 5.61 (1H, d, J$_{13,14}$=10.5 Hz, H-13), 6.33 (1H, d, J$_{10,11}$=15.5 Hz, H-10), 7.22 (1H, d, H-11), 9.69 (1H, s, H-20).

Example 14

Production of 23-Thiourea Derivatives 410 mg of the crude Compound (5) prepared in Reference Example 4 was dissolved in 8 mL of acetonitrile, to which 60 μL of triethylamine and 70 μL of benzyl isothiocyanate were added and allowed to react for 1 hour at room temperature. Then, 0.2 mL of concentrated aqueous ammonia was added to the solution and concentrated. Next, the residue obtained was dissolved in 10 mL of acetonitrile, and to this solution, 3 mL of 0.3 M hydrochloric acid was added and left at rest for 2 hours at room temperature to remove the acetal group. The reaction solution was concentrated to a small amount, which was neutralized by adding 5% aqueous sodium hydrogen carbonate solution. The resulting precipitate was extracted with chloroform. The organic layer was washed with water, dried with anhydrous sodium sulfate, and concentrated. The residue obtained was purified by silica gel column chromatography (developed with chloroform:methanol=10:1) to give 179 mg of MKT-3501, a 23-thiourea derivative, as a colorless solid. The yield based on Compound (4) was 48%. Reaction formula is shown below.

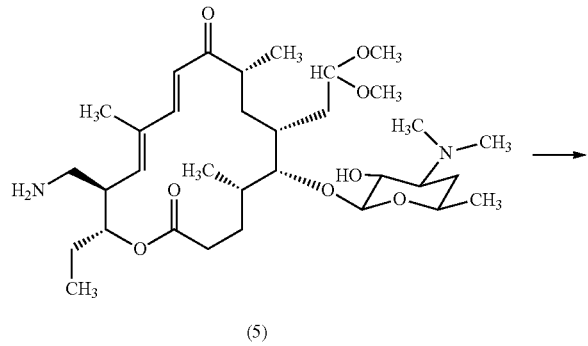

(5)

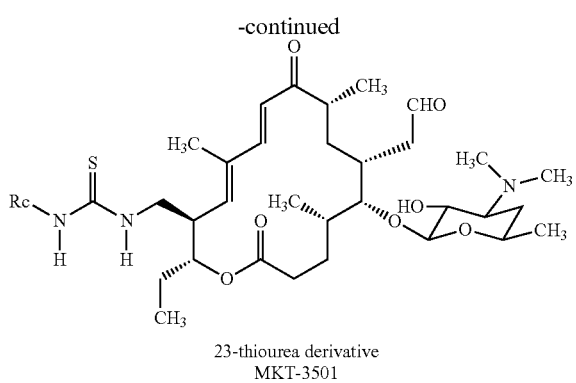

23-thiourea derivative
MKT-3501

The analytical values of MKT-3501 obtained are shown below.

$^1$H-NMR (deuteriochloroform): δ 1.75 (3H, s, H-22), 2.26 (6H, s, Me$_2$N), 4.18 (1H, d, H-1'), 4.50 (2H, br s, PhCH$_2$), 5.46 (1H, d, J$_{13,14}$=10 Hz, H-13), 5.74 (1H, br s, NH), 6.33 (1H, d, J$_{10,11}$=15.5 Hz, H-10), 6.34 (1H, br s, PhCH$_2$NH), 7.12 (1H, d, H-11), 9.69 (1H, s, H-20).

Experimental Example 1

Antimicrobial Activity Test (1)

The effect of the anti-PRSP agent of the present invention can be confirmed by the following experiments.

Using *Streptococcus pneumoniae* that include clinical isolates of PRSP, the antimicrobial activity of each of the prepared anti-PRSP agents was measured in accordance with the "determination method of minimum inhibitory concentration of drug against bacteria" of Japanese Society of Chemotherapy (for re-revised version, see Chemotherapy 29; 76, 1981). The results (MIC) are shown in the following Tables 1 to 23.

For comparison, the antimicrobial activity of 3,4'-dideoxy-mycaminosyltylonolide (DDMT), a compound represented by the formula (I) where R is a hydroxy group, is also shown.

11 test strains of *Streptococcus pneumoniae* including IMC B-0919 are all clinical isolates, of which 2 strains, IMC B-0921 and IMC B-1229, are classified into penicillin susceptible *Streptococcus pneumoniae* (PSSP) and the remaining 9 strains are classified into penicillin-resistant *Streptococcus pneumoniae* (PRSP) (according to NCCLS standards).

TABLE 1

| Test Microorganism | | Reference | Present Invention | | | | MIC (μg/mL) |
| --- | --- | --- | --- | --- | --- | --- | --- |
| *Streptococcus pneumoniae* | | DDMT | MKT-1001 | MKT-1002 | MKT-1003 | MKT-1004 | MKT-1005 |
| PRSP | IMC B-0919 | 0.39 | 0.1 | 0.05 | 0.2 | 0.2 | 1.56 |
|  | IMC B-0920 | 0.2 | 0.1 | 0.05 | 0.2 | 0.2 | 0.78 |
|  | IMC B-0922 | 0.2 | 0.1 | 0.1 | 0.2 | 0.2 | 1.56 |
|  | IMC B-1231 | >50 | 50 | 50 | 12.5 | 12.5 | 50 |
|  | IMC B-1232 | 0.39 | 0.1 | 0.1 | 0.2 | 0.2 | 1.56 |
|  | IMC B-1233 | 0.39 | 0.1 | 0.1 | 0.2 | 0.2 | 1.56 |
|  | IMC B-1234 | 0.2 | 0.1 | 0.1 | 0.2 | 0.2 | 1.56 |
|  | IMC B-1235 | >50 | 50 | 6.25 | 50 | 25 | 50 |
|  | IMC B-1236 | >50 | 25 | 6.25 | 25 | 25 | 25 |
| PSSP | IMC B-0921 | 0.1 | 0.1 | 0.1 | 0.2 | 0.2 | 1.56 |
|  | IMC B-1229 | 0.1 | 0.1 | 0.05 | 0.2 | 0.1 | 1.56 |

TABLE 2

| Test Microorganism | | Reference | Present Invention | | | | MIC (µg/mL) |
|---|---|---|---|---|---|---|---|
| Streptococcus pneumoniae | | DDMT | MKT-1006 | MKT-1007 | MKT-1008 | MKT-1009 | MKT-1010 |
| PRSP | IMC B-0919 | 0.39 | 0.2 | 1.56 | 0.78 | 0.2 | 0.39 |
| | IMC B-0920 | 0.2 | 0.2 | 1.56 | 0.78 | 0.2 | 0.39 |
| | IMC B-0922 | 0.39 | 0.2 | 1.56 | 0.78 | 0.2 | 0.39 |
| | IMC B-1231 | 12.5 | 0.78 | 3.13 | 1.56 | 0.39 | >50 |
| | IMC B-1232 | 0.2 | 0.2 | 0.78 | 0.39 | 0.1 | 0.2 |
| | IMC B-1233 | 0.2 | 0.2 | 0.78 | 0.39 | 0.1 | 0.39 |
| | IMC B-1234 | 0.2 | 0.2 | 0.78 | 0.78 | 0.2 | 0.39 |
| | IMC B-1235 | 50 | 6.25 | 50 | 50 | 6.25 | 50 |
| | IMC B-1236 | 50 | 6.25 | 25 | 25 | 3.13 | 50 |
| PSSP | IMC B-0921 | 0.2 | 0.2 | 1.56 | 0.78 | 0.2 | 0.2 |
| | IMC B-1229 | 0.1 | 0.2 | 1.56 | 0.78 | 0.2 | 0.39 |

TABLE 3

| Test Microorganism | | Reference | Present Invention | | | | MIC (µg/mL) |
|---|---|---|---|---|---|---|---|
| Streptococcus pneumoniae | | DDMT | MKT-1011 | MKT-1012 | MKT-1013 | MKT-1014 | MKT-1015 |
| PRSP | IMC B-0919 | 0.39 | 0.1 | 0.39 | 0.39 | 0.78 | 1.56 |
| | IMC B-0920 | 0.39 | 0.1 | 0.39 | 0.39 | 0.78 | 0.78 |
| | IMC B-0922 | 0.2 | 0.2 | 0.39 | 0.39 | 0.39 | 0.78 |
| | IMC B-1231 | 50 | 50 | 50 | 25 | 25 | 25 |
| | IMC B-1232 | 0.39 | 0.1 | 0.78 | 0.78 | 0.78 | 1.56 |
| | IMC B-1233 | 0.2 | 0.1 | 0.39 | 0.39 | 0.78 | 1.56 |
| | IMC B-1234 | 0.2 | 0.1 | 0.78 | 0.39 | 0.78 | 1.56 |
| | IMC B-1235 | >50 | 6.25 | >50 | 50 | 50 | 50 |
| | IMC B-1236 | >50 | 1.56 | >50 | 50 | 50 | 50 |
| PSSP | IMC B-0921 | 0.2 | 0.1 | 0.39 | 0.39 | 0.39 | 0.78 |
| | IMC B-1229 | 0.2 | 0.2 | 0.39 | 0.39 | 0.39 | 0.78 |

TABLE 4

| Test Microorganism | | Reference | Present Invention | | | | | MIC (µg/mL) |
|---|---|---|---|---|---|---|---|---|
| Streptococcus pneumoniae | | DDMT | MKT-2002 | MKT-2003 | MKT-2004 | MKT-2005 | MKT-2006 | MKT-2007 |
| PRSP | IMC B-0919 | 0.2 | 0.1 | 0.2 | 0.2 | 0.2 | 0.2 | 0.1 |
| | IMC B-0920 | 0.39 | 0.05 | 0.2 | 0.78 | 0.2 | 0.78 | 0.39 |
| | IMC B-0922 | 0.2 | 0.1 | 0.2 | 0.39 | 0.1 | 0.2 | 0.0.5 |
| | IMC B-1231 | 25 | 0.39 | >50 | 12.5 | 0.78 | 0.78 | 0.78 |
| | IMC B-1232 | 0.2 | 0.05 | 0.05 | 0.39 | 0.05 | <0.025 | 0.05 |
| | IMC B-1233 | 0.1 | 0.05 | 0.2 | 0.39 | <0.025 | <0.025 | <0.025 |
| | IMC B-1234 | 0.1 | 0.1 | 0.05 | 0.78 | 0.1 | <0.025 | <0.025 |
| | IMC B-1235 | 25 | 25 | 12.5 | 25 | 1.56 | 1.56 | 3.13 |
| | IMC B-1236 | 50 | 12.5 | 12.5 | 25 | 3.13 | 1.56 | 3.13 |
| PSSP | IMC B-0921 | 0.1 | 0.1 | <0.025 | 0.39 | 0.05 | 0.1 | 0.05 |
| | IMC B-1229 | 0.1 | 0.1 | 0.2 | 0.39 | 0.1 | 0.1 | 0.05 |

TABLE 5

| Test Microorganism | | Reference | Present Invention | | | | MIC (µg/mL) |
|---|---|---|---|---|---|---|---|
| Streptococcus pneumoniae | | DDMT | MKT-3001 | MKT-3002 | MKT-3003 | MKT-3004 | |
| PRSP | IMC B-0919 | 0.39 | 0.39 | 0.1 | <0.025 | 0.2 | |
| | IMC B-0920 | 0.39 | 0.2 | 0.2 | <0.025 | 0.1 | |
| | IMC B-0922 | 0.3.9 | 0.2 | 0.1 | <0.025 | 0.1 | |
| | IMC B-1231 | >50 | >50 | 50 | 50 | 25 | |
| | IMC B-1232 | 0.1 | 0.1 | <0.025 | <0.025 | 0.2 | |
| | IMC B-1233 | 0.2 | 0.2 | 0.1 | <0.025 | 0.2 | |
| | IMC B-1234 | 0.2 | 0.2 | <0.1 | <0.025 | 0.2 | |
| | IMC B-1235 | 25 | 50 | 3.13 | 1.56 | 50 | |
| | IMC B-1236 | 50 | 25 | 3.13 | 1.56 | 50 | |

TABLE 5-continued

| Test Microorganism | | Reference | MIC (µg/mL) Present Invention | | | |
|---|---|---|---|---|---|---|
| Streptococcus pneumoniae | | DDMT | MKT-3001 | MKT-3002 | MKT-3003 | MKT-3004 |
| PSSP | IMC B-0921 | 0.2 | 0.2 | 0.1 | <0.025 | 0.1 |
| | IMC B-1229 | 0.2 | 0.39 | 0.1 | 0.1 | 0.1 |

TABLE 6

| Test Microorganism | | Reference | MIC (µg/mL) Present Invention | | | | |
|---|---|---|---|---|---|---|---|
| Streptococcus pneumoniae | | DDMT | MKT-3201 | MKT-3202 | MKT-3203 | MKT-3204 | MKT-3205 |
| PRSP | IMC B-0919 | 0.39 | 0.78 | 0.2 | 0.2 | 0.2 | 0.78 |
| | IMC B-0920 | 0.39 | 0.78 | 0.2 | 0.2 | 0.1 | 0.78 |
| | IMC B-0922 | 0.2 | 0.39 | <0.025 | <0.025 | 0.2 | 0.78 |
| | IMC B-1231 | 25 | 1.56 | 0.05 | 0.78 | 12.5 | 50 |
| | IMC B-1232 | 0.2 | 0.39 | 0.1 | <0.025 | 0.2 | 0.78 |
| | IMC B-1233 | 0.2 | 0.39 | <0.025 | <0.025 | 0.2 | 0.78 |
| | IMC B-1234 | 0.2 | 0.39 | <0.025 | <0.025 | 0.1 | 0.39 |
| | IMC B-1235 | 50 | 12.5 | 0.1 | 6.25 | 50 | >50 |
| | IMC B-1236 | 50 | 50 | 6.25 | 6.25 | 50 | >50 |
| PSSP | IMC B-0921 | 0.2 | 0.2 | <0.025 | <0.025 | 0.1 | 0.2 |
| | IMC B-1229 | 0.2 | 0.2 | <0.025 | <0.025 | 0.1 | 0.2 |

TABLE 7

| Test Microorganism | | Reference | MIC (µg/mL) Present Invention | | | | |
|---|---|---|---|---|---|---|---|
| Streptococcus pneumoniae | | DDMT | MKT-3101 | MKT-3102 | MKT-3301 | MKT-3401 | MKT-3501 |
| PRSP | IMC B-0919 | 0.39 | 0.78 | 0.1 | <0.025 | 0.2 | 0.39 |
| | IMC B-0920 | 0.39 | 0.78 | 0.2 | <0.025 | 0.2 | 0.2 |
| | IMC B-0922 | 0.2 | 0.39 | 0.2 | <0.025 | 0.39 | 0.39 |
| | IMC B-1231 | 25 | 12.5 | 0.2 | 3.13 | 6.25 | 6.25 |
| | IMC B-1232 | 0.2 | 0.2 | 0.1 | <0.025 | 0.2 | 0.39 |
| | IMC B-1233 | 0.2 | 0.2 | 0.1 | <0.025 | 0.2 | 0.39 |
| | IMC B-1234 | 0.2 | 0.2 | 0.1 | <0.025 | 0.2 | 0.2 |
| | IMC B-1235 | 50 | 25 | 6.25 | 6.25 | 50 | 50 |
| | IMC B-1236 | 50 | 50 | 6.25 | 12.5 | 25 | 25 |
| PSSP | IMC B-0921 | 0.2 | 0.2 | 0.1 | <0.025 | 0.1 | 0.2 |
| | IMC B-1229 | 0.2 | 0.2 | 0.2 | <0.025 | 0.1 | 0.2 |

TABLE 8

| Test Microorganism | | Reference | MIC (µg/mL) Present Invention | | | |
|---|---|---|---|---|---|---|
| Streptococcus pneumoniae | | DDMT | MKT-3701 | MKT-3702 | MKT-3703 | MKT-3005 |
| PRSP | IMC B-0919 | 0.2 | 0.1 | 0.05 | <0.025 | 0.78 |
| | IMC B-0920 | 0.39 | 0.2 | 0.1 | 0.025 | 1.56 |
| | IMC B-0922 | 0.2 | 0.1 | 0.1 | <0.025 | 0.39 |
| | IMC B-1231 | 25 | 3.13 | 0.78 | 6.25 | 50 |
| | IMC B-1232 | 0.2 | 0.05 | 0.1 | <0.025 | 0.2 |
| | IMC B-1233 | 0.1 | 0.05 | <0.025 | <0.025 | 0.05 |
| | IMC B-1234 | 0.1 | 0.1 | 0.1 | <0.025 | 0.2 |
| | IMC B-1235 | 25 | 12.5 | 0.78 | 6.25 | 100 |
| | IMC B-1236 | 50 | 12.5 | 0.78 | 12.5 | 100 |
| PSSP | IMC B-0921 | 0.1 | 0.05 | 0.1 | <0.025 | 0.1 |
| | IMC B-1229 | 0.1 | 0.05 | 0.1 | 0.1 | 0.2 |

TABLE 9

| Test Microorganism | | Reference | Present Invention | | | | MIC (µg/mL) |
|---|---|---|---|---|---|---|---|
| Streptococcus pneumoniae | | DDMT | MKT-2008 | MKT-2009 | MKT-2010 | MKT-3801 | MKT-3802 |
| PRSP | IMC B-0919 | 0.1 | 0.05 | 0.39 | 0.05 | 0.05 | <0.025 |
| | IMC B-0920 | 0.2 | 0.05 | 0.39 | 0.1 | 0.05 | <0.025 |
| | IMC B-0922 | 0.1 | 0.1 | 0.39 | 0.1 | 0.05 | 0.05 |
| | IMC B-1231 | 6.25 | 3.13 | 25 | 3.13 | 6.25 | 0.39 |
| | IMC B-1232 | 0.2 | 0.1 | 0.39 | 0.2 | 0.1 | <0.025 |
| | IMC B-1233 | 0.2 | 0.1 | 0.39 | 0.1 | 0.05 | <0.025 |
| | IMC B-1234 | 0.2 | 0.1 | 0.39 | 0.1 | 0.05 | 0.025 |
| | IMC B-1235 | 50 | 50 | 50 | 12.5 | 50 | 12.5 |
| | IMC B-1236 | 25 | 25 | 50 | 12.5 | 50 | 12.5 |
| PSSP | IMC B-0921 | 0.1 | 0.1 | 0.39 | 0.1 | 0.05 | 0.05 |
| | IMC B-1229 | 0.2 | 0.1 | 0.39 | 0.1 | 0.1 | 0.05 |

TABLE 10

| Test Microorganism | | Reference | Present Invention | | MIC (µg/mL) |
|---|---|---|---|---|---|
| Streptococcus pneumoniae | | DDMT | MKT-1016 | MKT-1017 | |
| PRSP | IMC B-0919 | 0.39 | 0.78 | 0.78 | |
| | IMC B-0920 | 0.39 | 0.78 | 0.78 | |
| | IMC B-0922 | 0.39 | 0.39 | 0.39 | |
| | IMC B-1231 | 50 | 12.5 | 12.5 | |
| | IMC B-1232 | 0.78 | 0.78 | 0.78 | |
| | IMC B-1233 | 0.39 | 0.78 | 0.78 | |
| | IMC B-1234 | 0.39 | 0.78 | 0.78 | |
| | IMC B-1235 | >50 | 50 | 50 | |
| | IMC B-1236 | >50 | 50 | 50 | |
| | IMC B-0921 | 0.78 | 0.78 | 0.39 | |
| PSSP | IMC B-1229 | 0.78 | 0.78 | 0.78 | |

TABLE 11

| Test Microorganism | | Reference | Present Invention | | | | MIC (µg/mL) |
|---|---|---|---|---|---|---|---|
| Streptococcus pneumoniae | | DDMT | MKT-2101 | MKT-2102 | MKT-2103 | MKT-2104 | MKT-2105 |
| PRSP | IMC B-0919 | 0.39 | 0.05 | 0.20 | 0.39 | 0.39 | 0.39 |
| | IMC B-0920 | 0.39 | 0.10 | 0.20 | 0.39 | 0.39 | 0.39 |
| | IMC B-0922 | 0.39 | 0.20 | 0.20 | 0.39 | 0.78 | 0.39 |
| | IMC B-1231 | >50 | 50 | 50 | 50 | 50 | 50 |
| | IMC B-1232 | 0.39 | 0.10 | 0.20 | 0.39 | 0.39 | 0.39 |
| | IMC B-1233 | 0.39 | 0.10 | 0.20 | 0.39 | 0.78 | 0.20 |
| | IMC B-1234 | 0.20 | 0.10 | 0.20 | 0.39 | 0.39 | 0.20 |
| | IMC B-1235 | >50 | 50 | 50 | 50 | 50 | 50 |
| | IMC B-1236 | >50 | 6.25 | 6.25 | 12.5 | 50 | 25 |
| PSSP | IMC B-0921 | 0.20 | 0.10 | 0.10 | 0.20 | 0.39 | 0.20 |
| | IMC B-1229 | 0.20 | 0.10 | 0.10 | 0.20 | 0.39 | 0.20 |

TABLE 12

| Test Microorganism | | Reference | Present Invention | | | | MIC (µg/mL) |
|---|---|---|---|---|---|---|---|
| Streptococcus pneumoniae | | DDMT | MKT-5801 | MKT-5802 | MKT-5803 | MKT-5804 | MKT-5805 |
| PRSP | IMC B-0919 | 0.39 | 0.20 | 0.20 | 0.39 | 0.20 | 0.39 |
| | IMC B-0920 | 0.39 | 0.10 | 0.20 | 0.20 | 0.10 | 0.39 |
| | IMC B-0922 | 0.39 | 0.20 | 0.20 | 0.39 | 0.10 | 0.39 |
| | IMC B-1231 | >50 | 25 | 50 | 50 | 6.25 | 12.5 |
| | IMC B-1232 | 0.39 | 0.10 | 0.20 | 0.20 | 0.20 | 0.39 |
| | IMC B-1233 | 0.39 | 0.10 | 0.10 | 0.20 | 0.10 | 0.39 |
| | IMC B-1234 | 0.20 | 0.20 | 0.20 | 0.39 | 0.10 | 0.39 |
| | IMC B-1235 | >50 | 0.39 | 50 | 50 | 25 | 50 |
| | IMC B-1236 | 50 | 12.5 | 25 | 25 | 6.25 | 50 |
| PSSP | IMC B-0921 | 0.20 | 0.10 | 0.20 | 0.39 | 0.10 | 0.39 |
| | IMC B-1229 | 0.20 | 0.20 | 0.39 | 0.78 | 0.10 | 0.39 |

TABLE 13

| Test Microorganism | | Reference | Present Invention | | | | MIC (μg/mL) |
|---|---|---|---|---|---|---|---|
| Streptococcus pneumoniae | | DDMT | MKT-5806 | MKT-5807 | MKT-5808 | MKT-5809 | MKT-5810 |
| PRSP | IMC B-0919 | 0.39 | 0.39 | 0.39 | 0.20 | 0.20 | 0.10 |
| | IMC B-0920 | 0.39 | 0.39 | 0.39 | 0.20 | 0.20 | 0.20 |
| | IMC B-0922 | 0.39 | 0.39 | 0.39 | 0.10 | 0.20 | 0.10 |
| | IMC B-1231 | >50 | 1.56 | 0.78 | 0.39 | 1.56 | 3.13 |
| | IMC B-1232 | 0.39 | 0.39 | 0.39 | 0.20 | 0.20 | 0.39 |
| | IMC B-1233 | 0.39 | 0.39 | 0.39 | 0.20 | 0.20 | 0.05 |
| | IMC B-1234 | 0.20 | 0.39 | 0.39 | 0.10 | 0.20 | 0.10 |
| | IMC B-1235 | >50 | 50 | 50 | 50 | 50 | 50 |
| | IMC B-1236 | 50 | 12.5 | 6.25 | 6.25 | 3.13 | 50 |
| PSSP | IMC B-0921 | 0.20 | 0.39 | 0.39 | 0.10 | 0.20 | 0.10 |
| | IMC B-1229 | 0.20 | 0.39 | 0.39 | 0.20 | 0.20 | 0.20 |

TABLE 14

| Test Microorganism | | Reference | Present Invention | | | | MIC (μg/mL) |
|---|---|---|---|---|---|---|---|
| Streptococcus pneumoniae | | DDMT | MKT-5811 | MKT-5812 | MKT-5813 | MKT-5814 | |
| PRSP | IMC B-0919 | 0.39 | 0.20 | 0.20 | 0.20 | 0.20 | |
| | IMC B-0920 | 0.20 | 0.78 | 0.39 | 0.20 | 0.78 | |
| | IMC B-0922 | 0.39 | 0.39 | 0.39 | 0.10 | 0.20 | |
| | IMC B-1231 | >50 | 25 | 25 | 3.13 | 12.5 | |
| | IMC B-1232 | 0.39 | 0.78 | 0.39 | 0.20 | 0.20 | |
| | IMC B-1233 | 0.39 | 0.20 | 0.39 | 0.20 | 0.20 | |
| | IMC B-1234 | 0.20 | 0.20 | 0.39 | 0.20 | 0.20 | |
| | IMC B-1235 | 50 | 50 | 50 | 25 | 50 | |
| | IMC B-1236 | 50 | 50 | 50 | 25 | 50 | |
| PSSP | IMC B-0921 | 0.20 | 0.39 | 0.39 | 0.10 | 0.20 | |
| | IMC B-1229 | 0.20 | 0.20 | 0.39 | 0.20 | 0.20 | |

TABLE 15

| Test Microorganism | | Reference | Present Invention | | | MIC (μg/mL) |
|---|---|---|---|---|---|---|
| Streptococcus pneumoniae | | DDMT | MKT-5701 | MKT-5704 | MKT-5705 | |
| PRSP | IMC B-0919 | 0.39 | 0.10 | 0.39 | 0.10 | |
| | IMC B-0920 | 0.39 | 0.20 | 0.39 | 0.20 | |
| | IMC B-0922 | 0.39 | 0.20 | 0.39 | 0.20 | |
| | IMC B-1231 | 50 | 0.78 | 6.25 | 12.5 | |
| | IMC B-1232 | 0.39 | 0.10 | 0.39 | 0.10 | |
| | IMC B-1233 | 0.39 | 0.20 | 0.39 | 0.20 | |
| | IMC B-1234 | 0.20 | 0.20 | 0.39 | 0.20 | |
| | IMC B-1235 | >50 | 50 | 12.5 | 25 | |
| | IMC B-1236 | >50 | 50 | 6.25 | 12.5 | |
| PSSP | IMC B-0921 | 0.20 | 0.10 | 0.39 | 0.10 | |
| | IMC B-1229 | 0.20 | 0.10 | 0.39 | 0.20 | |

TABLE 16

| Test Microorganism | | Reference | Present Invention | | | | MIC (μg/mL) |
|---|---|---|---|---|---|---|---|
| Streptococcus pneumoniae | | DDMT | MKT-6101 | MKT-6102 | MKT-6103 | MKT-6104 | MKT-6105 |
| PRSP | IMC B-0919 | 0.39 | 0.20 | 0.20 | 0.39 | 1.56 | 0.39 |
| | IMC B-0920 | 0.20 | 0.10 | 0.10 | 0.10 | 0.78 | 0.20 |
| | IMC B-0922 | 0.39 | 0.20 | 0.20 | 0.39 | 0.78 | 0.20 |
| | IMC B-1231 | >50 | 25 | 25 | 25 | 50 | 50 |
| | IMC B-1232 | 0.20 | 0.20 | 0.20 | 0.39 | 1.56 | 0.20 |
| | IMC B-1233 | 0.39 | 0.20 | 0.20 | 0.39 | 1.56 | 0.39 |
| | IMC B-1234 | 0.20 | 0.20 | 0.20 | 0.39 | 1.56 | 0.39 |

TABLE 16-continued

| Test Microorganism | | Reference | Present Invention | | | | MIC (μg/mL) |
|---|---|---|---|---|---|---|---|
| Streptococcus pneumoniae | | DDMT | MKT-6101 | MKT-6102 | MKT-6103 | MKT-6104 | MKT-6105 |
| | IMC B-1235 | >50 | 50 | 50 | 25 | 25 | 25 |
| | IMC B-1236 | >50 | 50 | 50 | 25 | 25 | 25 |
| PSSP | IMC B-0921 | 0.20 | 0.20 | 0.10 | 0.10 | 0.78 | 0.20 |
| | IMC B-1229 | 0.20 | 0.20 | 0.10 | 0.39 | 1.56 | 0.39 |

TABLE 17

| Test Microorganism | | Reference | Present Invention | | | | MIC (μg/mL) |
|---|---|---|---|---|---|---|---|
| Streptococcus pneumoniae | | DDMT | MKT-6106 | MKT-6107 | MKT-6108 | MKT-6109 | MKT-6110 |
| PRSP | IMC B-0919 | 0.39 | 0.39 | 0.78 | 0.20 | 0.20 | 0.20 |
| | IMC B-0920 | 0.39 | 0.20 | 1.56 | 0.20 | 0.20 | 0.20 |
| | IMC B-0922 | 0.39 | 0.20 | 0.78 | 0.20 | 0.39 | 0.39 |
| | IMC B-1231 | >50 | 50 | 25 | 6.25 | 50 | 50 |
| | IMC B-1232 | 0.20 | 0.10 | 1.56 | 0.39 | 0.39 | 0.39 |
| | IMC B-1233 | 0.39 | 0.39 | 3.13 | 0.39 | 0.39 | 0.39 |
| | IMC B-1234 | 0.20 | 0.39 | 0.78 | 0.39 | 0.39 | 0.39 |
| | IMC B-1235 | >50 | 25 | 25 | 50 | 50 | 25 |
| | IMC B-1236 | >50 | 25 | 25 | 25 | 50 | 50 |
| PSSP | IMC B-0921 | 0.20 | 0.20 | 0.39 | 0.20 | 0.20 | 0.20 |
| | IMC B-1229 | 0.20 | 0.20 | 0.39 | 0.39 | 0.20 | 0.20 |

TABLE 18

| Test Microorganism | | Reference | Present Invention | | MIC (μg/mL) |
|---|---|---|---|---|---|
| Streptococcus pneumoniae | | DDMT | MKT-6111 | MKT-6112 | |
| PRSP | IMC B-0919 | 0.39 | 0.10 | 0.39 | |
| | IMC B-0920 | 0.39 | 0.20 | 0.39 | |
| | IMC B-0922 | 0.39 | 0.20 | 0.39 | |
| | IMC B-1231 | >50 | 25 | 50 | |
| | IMC B-1232 | 0.39 | 0.20 | 0.39 | |
| | IMC B-1233 | 0.39 | 0.20 | 0.39 | |
| | IMC B-1234 | 0.20 | 0.20 | 0.39 | |
| | IMO B-1235 | >50 | 50 | 50 | |
| | IMC B-1236 | 50 | 50 | 25 | |
| PSSP | IMC B-0921 | 0.20 | 0.10 | 0.20 | |
| | IMC B-1229 | 0.20 | 0.20 | 0.20 | |

TABLE 19

| Test Microorganism Streptococcus Pneumoniae | | Reference | Present Invention | | MIC (μg/mL) |
|---|---|---|---|---|---|
| | | DDMT | MKT-2106 | MKT-2107 | MKT-2108 |
| PRSP | IMC B-0919 | 0.39 | 0.10 | 0.05 | 0.05 |
| | IMC B-0920 | 0.39 | 0.20 | 0.05 | 0.05 |
| | IMC B-0922 | 0.39 | 0.20 | 0.05 | 0.05 |
| | IMC B-1231 | >50 | 50 | 3.13 | 1.56 |
| | IMC B-1232 | 0.39 | 0.20 | 0.10 | 0.05 |
| | IMC B-1233 | 0.20 | 0.20 | 0.05 | 0.05 |
| | IMC B-1234 | 0.20 | 0.20 | 0.05 | 0.05 |
| | IMC B-1235 | >50 | 50 | 12.5 | 25 |
| | IMC B-1236 | >50 | 50 | 3.13 | 3.13 |
| PSSP | IMC B-0921 | 0.10 | 0.10 | 0.025 | 0.05 |
| | IMC B-1229 | 0.10 | 0.10 | 0.05 | 0.05 |

TABLE 20

| Test Microorganism | | Reference | Present Invention | | | | MIC (μg/mL) |
|---|---|---|---|---|---|---|---|
| Streptococcus pneumoniae | | DDMT | MKT-2109 | MKT-2110 | MKT-2111 | MKT-2112 | MKT-2113 |
| PRSP | IMC B-0919 | 0.39 | 0.05 | 0.05 | 0.20 | 0.39 | 0.10 |
| | IMC B-0920 | 0.39 | 0.10 | 0.20 | 0.20 | 0.39 | 0.10 |
| | IMC B-0922 | 0.20 | 0.10 | 0.10 | 0.20 | 0.2 | 0.10 |
| | IMC B-1231 | >50 | 25 | 25 | 50 | 50 | 25 |
| | IMC B-1232 | 0.78 | 0.10 | 0.20 | 0.39 | 0.39 | 0.20 |
| | IMC B-1233 | 0.39 | 0.10 | 0.10 | 0.39 | 0.78 | 0.10 |
| | IMC B-1234 | 0.39 | 0.10 | 0.10 | 0.39 | 0.39 | 0.10 |
| | IMC B-1235 | >50 | 50 | 50 | 50 | 50 | 50 |
| | IMC B-1236 | >50 | 6.25 | 12.5 | 50 | 50 | 12.5 |
| PSSP | IMC B-0921 | 0.20 | 0.10 | 0.10 | 0.20 | 0.20 | 0.10 |
| | IMC B-1229 | 0.39 | 0.10 | 0.20 | 0.39 | 0.39 | 0.20 |

TABLE 21

| Test Microorganism | | Reference | Present Invention | | | MIC (µg/mL) |
| --- | --- | --- | --- | --- | --- | --- |
| Streptococcus pneumoniae | | DDMT | MKT-6113 | MKT-6114 | MKT-6115 | MKT-3007 |
| PRSP | IMC B-0919 | 0.39 | 0.78 | 0.39 | 0.78 | 0.20 |
|  | IMC B-0920 | 0.39 | 1.56 | 0.78 | 1.56 | 0.20 |
|  | IMC B-0922 | 0.39 | 1.56 | 0.78 | 1.56 | 0.20 |
|  | IMC B-1231 | >50 | >50 | >50 | >50 | 25 |
|  | IMC B-1232 | 0.78 | 1.56 | 0.78 | 1.56 | 0.20 |
|  | IMC B-1233 | 0.39 | 0.78 | 0.39 | 0.39 | 0.20 |
|  | IMC B-1234 | 0.39 | 0.39 | 0.20 | 0.39 | 0.20 |
|  | IMC B-1235 | >50 | >50 | >50 | >50 | 50 |
|  | IMC B-1236 | >50 | >50 | >50 | >50 | 50 |
| PSSP | IMC B-0921 | 0.39 | 0.20 | 0.20 | 0.20 | 0.10 |
|  | IMC B-1229 | 0.39 | 0.39 | 0.20 | 0.20 | 0.20 |

TABLE 22

| Test Microorganism | | Reference | Present Invention | | | | | MIC (µg/mL) |
| --- | --- | --- | --- | --- | --- | --- | --- | --- |
| Streptococcus pneumoniae | | DDMT | MKT-3211 | MKT-3212 | MKT-3213 | MKT-3214 | MKT-3215 | MKT-3216 |
| PRSP | IMC B-0919 | 0.20 | 0.10 | 0.10 | 0.10 | 0.10 | 0.05 | 0.10 |
|  | IMC B-0920 | 0.39 | 0.39 | 0.20 | 0.20 | 0.20 | 0.10 | 0.10 |
|  | IMC B-0922 | 0.20 | 0.20 | 0.05 | 0.10 | 0.05 | 0.10 | 0.10 |
|  | IMC B-1231 | 50 | 3.13 | 1.56 | 6.25 | 12.5 | 3.13 | 6.25 |
|  | IMC B-1232 | 0.20 | 0.05 | 0.05 | 0.10 | 0.10 | 0.10 | 0.05 |
|  | IMC B-1233 | 0.10 | 0.05 | 0.05 | 0.10 | 0.10 | 0.05 | 0.05 |
|  | IMC B-1234 | 0.20 | 0.05 | 0.05 | 0.10 | 0.10 | 0.05 | 0.05 |
|  | IMC B-1235 | 50 | 3.13 | 6.25 | 12.5 | 6.25 | 6.25 | 12.5 |
|  | IMC B-1236 | >50 | 3.13 | 6.25 | 12.5 | 12.5 | 3.13 | 12.5 |
| PSSP | IMC B-0921 | 0.10 | 0.10 | 0.05 | 0.10 | 0.10 | 0.025 | 0.10 |
|  | IMC B-1229 | 0.10 | 0.10 | 0.05 | 0.10 | 0.10 | 0.05 | 0.10 |

For the compounds of the present invention, MKT-1011, MKT-2003, MKT-3002 and MKT-3003, the antimicrobial activity was measured in the same way as in Experimental Example 1. In addition, for comparison, antimicrobial activities of DDMT; tylosin, which are 16-membered macrolide antibiotics, and clarithromycin (CAM) are also shown in Table 23. The compounds of the present invention inhibited the growth of the above-mentioned clinical isolates at lower concentrations compared to the respective compounds listed for comparison. Especially, MKT-3003 inhibited the growth of PRSP at remarkably low concentrations.

TABLE 23

| Test Microorganism | | Reference | | | | | | MIC (µg/mL) |
| --- | --- | --- | --- | --- | --- | --- | --- | --- |
| Streptococcus pneumoniae | | DDMT | Tylosin | CAM | MKT-1011 | MKT-2003 | MKT-3002 | MKT-3003 |
| PRSP | IMC B-0919 | 0.39 | 0.39 | 0.2 | 0.1 | 0.2 | 0.1 | <0.025 |
|  | IMC B-0920 | 0.39 | 0.39 | 0.2 | 0.1 | 0.2 | 0.2 | <0.025 |
|  | IMC B-0922 | 0.39 | 0.39 | 0.2 | 0.2 | 0.2 | 0.1 | <0.025 |
|  | IMC B-1231 | >50 | 100 | 25 | 50 | >50 | 50 | 50 |
|  | IMC B-1232 | 0.1 | 0.39 | 0.39 | 0.1 | 0.05 | <0.025 | <0.025 |
|  | IMC B-1233 | 0.2 | 0.78 | 0.05 | 0.1 | 0.2 | 0.1 | <0.025 |
|  | IMC B-1234 | 0.2 | 0.39 | 0.05 | 0.1 | 0.05 | <0.1 | <0.025 |
|  | IMC B-1235 | 50 | >100 | >100 | 6.25 | 12.5 | 3.13 | 1.56 |
|  | IMC B-1236 | 50 | >100 | >100 | 1.56 | 12.5 | 3.13 | 1.56 |
| PSSP | IMC B-0921 | 0.2 | 0.39 | 0.1 | 0.1 | <0.025 | 0.1 | <0.025 |
|  | IMC B-1229 | 0.2 | 0.39 | 0.1 | 0.2 | 0.2 | 0.1 | 0.1 |

Example 15

Production of Capsules (1)

100 mg of MKT3002, 100 mg of lactose, and 1 mg of magnesium stearate (the amounts indicated are per capsule) are uniformly mixed, and the resulting mixture (about 200 mg per capsule) is filled into a size 3, hard-gelatin capsule.

Example 16

Production of Capsules (2)

100 mg of MKT3003, 100 mg of lactose, and 1 mg of magnesium stearate (the amounts indicated are per capsule) are uniformly mixed, and the resulting mixture (about 200 mg per capsule) is filled into a size 3, hard-gelatin capsule.

Example 17

Production of Tablet (1)

70 mg of MKT3002, 60 mg of lactose, 57 mg of cornstarch (the amounts indicated are per tablet) are well mixed. The mixture is granulated by mixing with a 10% starch paste solution. To the resulting granules, 60 mg of cornstarch and 3 mg of magnesium stearate (the amounts indicated are per tablet) are added, mixed well, and formed into tablets having a diameter of 8 mm and a weight of about 250 mg.

Example 18

Production of Tablet (2)

70 mg of MICT3003, 60 mg of lactose, 57 mg of cornstarch (the amounts indicated are per tablet) are well mixed. The mixture is granulated by mixing with a 10% starch paste solution. To the resulting granules, 60 mg of cornstarch and 3 mg of magnesium stearate (the amounts indicated are per tablet) are added, mixed well, and formed into tablets having a diameter of 8 mm and a weight of about 250 mg.

Example 19

Production of Suspension Syrup (1)

200 mg of MKT3002, 100 mg of sodium carboxymethyl-cellulose, 14 mg of methyl p-hydroxybenzoate, 6 mg of ethyl p-hydroxybenzoate, 40 mL of simple syrup, and 10 mL of purified water (the amounts indicated are per bottle) are well mixed to form a suspension. This suspension is poured in a dispensing bottle.

Example 20

Production of Suspension Syrup (2)

200 mg of MKT3003, 100 mg of sodium carboxymethyl-cellulose, 14 mg of methyl p-hydroxybenzoate, 6 mg of ethyl p-hydroxybenzoate, 40 mL of simple syrup, and 10 mL of purified water (the amounts indicated are per bottle) are well mixed to form a suspension. This suspension is poured in a dispensing bottle.

Example 21

Production of Ointment (1)

3 g of stearyl alcohol, 8 g of white beeswax and 84 g of white petrolatum are dissolved by heating in a water bath, while stirring, 3 g of cholesterol is added and stirred until complete dissolution to prepare an ointment base. Next, 2 g of MKT3002 is placed in a mortar, blended with the ointment base by adding little by little, and cooled naturally to prepare 100 g of ointment.

Example 22

Production of Ointment (2)

3 g of stearyl alcohol, 8 g of white beeswax and 84 g of white petrolatum are dissolved by heating in a water bath, while stirring, 3 g of cholesterol is added and stirred until complete dissolution to prepare an ointment base. Next, 2 g of MKT3003 is placed in a mortar, blended with the ointment base by adding little by little, and cooled naturally to prepare 100 g of ointment.

INDUSTRIAL APPLICABILITY

The anti-penicillin resistant pneumococci agent of the present invention exhibits antibacterial activity against PRSP clinical isolates at a low concentration, can be clearly distinguished structurally from antibiotics that have been used for the treatment for PRSP, and thus is useful as a novel anti-penicillin resistant pneumococci agent. The anti-penicillin resistant pneumococci agent of the present invention can be suitably used as a new therapeutic approach where health care is provided.

The invention claimed is:

1. A method for treatment of penicillin-resistant pneumococcal infection, which comprises administrating a pharmaceutically effective amount of a compound represented by the formula (I) or a pharmacologically acceptable salt thereof to a subject having penicillin-resistant pneumococcal infection:

formula (I)

wherein, in the formula (I), R represents any one of a halogen atom, an azido group, Ra-Wa-, Rb-Wb-, Rc-Wc-, and RdRd'N—; the Wa represents one of —CO—O— and —CO—NH—; the Ra represents any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, a 5- to 14-membered ring heteroaralkyl group, a $C_{1-12}$ alkoxy group, an unsaturated $C_{2-12}$ alkoxy group, a $C_{6-14}$ aryloxy group and a 5- to 14-membered ring heteroaryloxy group, which may each have a substituent; the Wb represents —O—; the Rb represents any one of a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, and a 5- to 14-membered ring heteroaralkyl group, which may each have a substituent; the Wc represents any one of —NH—CO—O—, —NH—CO—NH—, —NH—CS—NH—, and —S—; the Rc represents any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group and a 5- to 14-membered ring heteroaralkyl group, which may each have a substituent; and the Rd and the Rd' may be the same or different and represent any one of a hydrogen atom, and a $C_{1-12}$ alkyl group, an unsaturated $C_{2-12}$ alkyl group, a $C_{6-14}$ aryl group, a 5- to 14-membered ring heteroaryl group, a $C_{7-16}$ aralkyl group, a 5- to 14-membered ring heteroaralkyl group, and a 3- to 8-membered ring nonaromatic heterocyclic group which the Rd and the Rd' together form, each of which groups may have a substituent.

2. The method according to claim 1, wherein, in the formula (I), R represents any one of an azido group, Ra-Wa-, Rb-Wb-, Rb-Wc-, and RdRd'N—; the Wa represents one of —CO—O— and —CO—NH—; the Ra represents any one of a $C_{1-12}$ alkyl group, a $C_{6-14}$ aryl group, a 5- to 14-membered ring heteroaryl group, a $C_{7-16}$ aralkyl group, and a $C_{1-12}$ alkoxy group, which may each have a substituent; the Wb represents —O—; the Rb represents any one of a $C_{1-12}$ alkyl group, an unsaturated $C_{2-12}$ alkyl group, and a $C_{7-16}$ aralkyl group, which may each have a substituent; the Wc represents any one of —NH—CO—O—, —NH—CO—NH—, and —S—; the Rc represents any one of an unsaturated $C_{2-12}$ alkyl group, a 5- to 14-membered ring heteroaryl group, and a $C_{7-16}$ aralkyl group, which may each have a substituent; and the Rd and the Rd' may be the same or different and represent one of a $C_{1-12}$ alkyl group and a $C_{6-14}$ aryl group, which may each have a substituent.

3. The method according to claim 1, wherein, in the formula (I), R is one group selected from the groups represented by the following formulae:

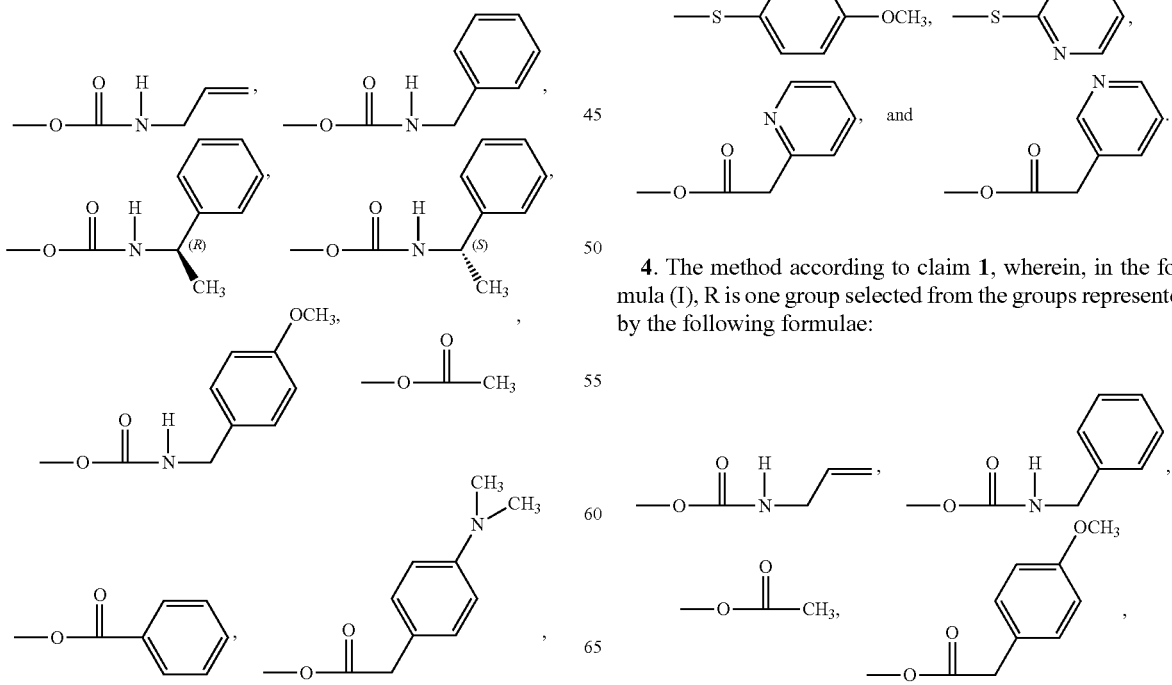

4. The method according to claim 1, wherein, in the formula (I), R is one group selected from the groups represented by the following formulae:

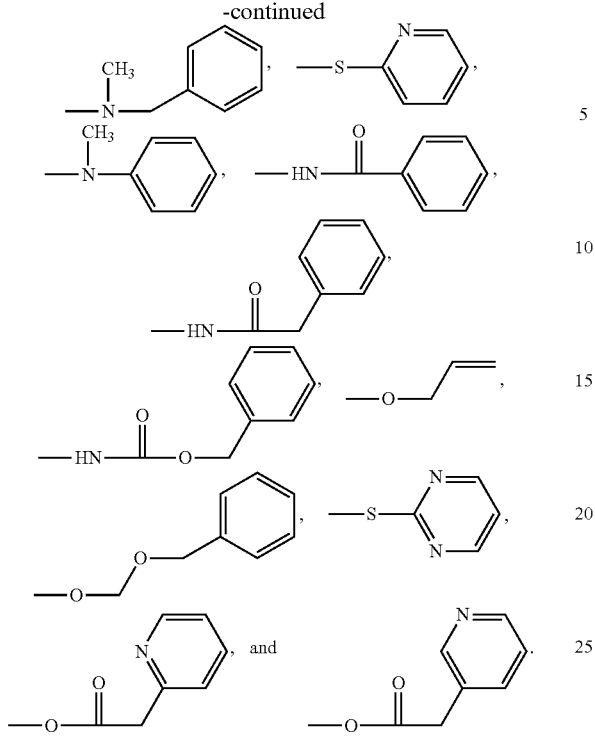

UNITED STATES PATENT AND TRADEMARK OFFICE
CERTIFICATE OF CORRECTION

| | |
|---|---|
| PATENT NO. | : 8,507,453 B2 |
| APPLICATION NO. | : 13/241967 |
| DATED | : August 13, 2013 |
| INVENTOR(S) | : Toshiaki Miyake |

Page 1 of 1

It is certified that error appears in the above-identified patent and that said Letters Patent is hereby corrected as shown below:

In the Claims:

Column 81, Line 27

Delete "substituent; the We represents" and replace it with -- substituent; the Wc represents --

Signed and Sealed this
Nineteenth Day of November, 2013

Teresa Stanek Rea
*Deputy Director of the United States Patent and Trademark Office*